United States Patent
Chen et al.

(10) Patent No.: US 10,370,363 B2
(45) Date of Patent: *Aug. 6, 2019

(54) INHIBITORS OF CXCR2

(71) Applicant: CHEMOCENTRYX, INC., Mountain View, CA (US)

(72) Inventors: Xi Chen, East Palo Alto, CA (US); Dean R. Dragoli, Los Altos, CA (US); Junfa Fan, Foster City, CA (US); Jaroslaw Kalisiak, Mountain View, CA (US); Manmohan Reddy Leleti, West San Jose, CA (US); Viengkham Malathong, Mountain View, CA (US); Jeffrey McMahon, San Francisco, CA (US); Hiroko Tanaka, Mountain View, CA (US); Ju Yang, Palo Alto, CA (US); Chao Yu, Sunnyvale, CA (US); Penglie Zhang, Foster City, CA (US); Venkat Mali, Cupertino, CA (US)

(73) Assignee: ChemoCentryx, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/722,785

(22) Filed: Oct. 2, 2017

(65) Prior Publication Data

US 2018/0170916 A1 Jun. 21, 2018

Related U.S. Application Data

(63) Continuation of application No. 15/353,949, filed on Nov. 17, 2016, now Pat. No. 9,809,581.

(60) Provisional application No. 62/257,529, filed on Nov. 19, 2015.

(51) Int. Cl.
| | |
|---|---|
| *A61K 45/06* | (2006.01) |
| *C07B 59/00* | (2006.01) |
| *A61K 31/422* | (2006.01) |
| *C07D 405/12* | (2006.01) |
| *C07D 405/14* | (2006.01) |
| *C07D 413/12* | (2006.01) |
| *A61K 31/4035* | (2006.01) |
| *A61K 31/4439* | (2006.01) |

(52) U.S. Cl.
CPC ........ *C07D 405/12* (2013.01); *A61K 31/4035* (2013.01); *A61K 31/422* (2013.01); *A61K 31/4439* (2013.01); *A61K 45/06* (2013.01); *C07B 59/002* (2013.01); *C07D 405/14* (2013.01); *C07D 413/12* (2013.01); *C07B 2200/05* (2013.01)

(58) Field of Classification Search
None
See application file for complete search history.

(56) References Cited

U.S. PATENT DOCUMENTS

| | | |
|---|---|---|
| 6,166,050 A | 12/2000 | Lombardo et al. |
| 9,809,581 B2 | 11/2017 | Chen et al. |
| 9,834,545 B2 | 12/2017 | Chen et al. |
| 2003/0204085 A1 | 10/2003 | Taveras et al. |
| 2004/0097547 A1 | 5/2004 | Taveras et al. |
| 2004/0106794 A1 | 6/2004 | Taveras et al. |
| 2004/0147559 A1 | 7/2004 | Taveras et al. |
| 2004/0209946 A1 | 10/2004 | Yin et al. |
| 2008/0261917 A1 | 10/2008 | Willems et al. |
| 2009/0306079 A1 | 12/2009 | Taveras et al. |
| 2010/0029670 A1 | 2/2010 | Baettig et al. |
| 2010/0267712 A1 | 10/2010 | Heemskerk et al. |
| 2011/0086842 A1 | 4/2011 | Stadtmueller et al. |
| 2011/0213029 A1 | 9/2011 | Taveras et al. |
| 2013/0231393 A1 | 9/2013 | Aubert |
| 2014/0296254 A1 | 10/2014 | Musicki et al. |
| 2014/0309208 A1 | 10/2014 | Musicki et al. |
| 2015/0087675 A1 | 3/2015 | Musicki et al. |

FOREIGN PATENT DOCUMENTS

| | | |
|---|---|---|
| WO | 01/64208 A1 | 9/2001 |
| WO | 01/92202 A1 | 12/2001 |
| WO | 02/057230 A1 | 7/2002 |
| WO | 02/067919 A1 | 9/2002 |
| WO | 02/076926 A1 | 10/2002 |
| WO | 02/083624 A1 | 10/2002 |
| WO | 03/080053 A1 | 10/2003 |
| WO | 2004/011418 A1 | 2/2004 |
| WO | 2005/075447 A1 | 8/2005 |

(Continued)

OTHER PUBLICATIONS

International Search Report and Written Opinion corresponding to PCT Application No. PCT/US2016/062417 dated Jan. 12, 2017, 12 pages.

International Search Report and Written Opinion corresponding to PCT Application No. PCT/US2016/062427 dated Feb. 21, 2017; 9 pages.

Aki, Cynthia et al., "Diaminocyclobutenediones as potent and orally available CXCR2 receptor antagonists: SAR in the phenolic amide region," *Bioorganic & Medicinal Chemistry Letters* (available online May 18, 2009); 19:4446-4449.

(Continued)

*Primary Examiner* — Brian J Davis
(74) *Attorney, Agent, or Firm* — Mintz Levin Cohn Ferris Glovsky and Popeo PC

(57) ABSTRACT

Compounds are provided as inhibitors of CXCR2, having the structure:

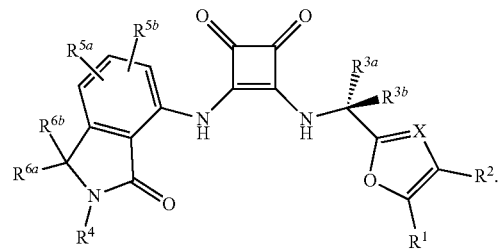

13 Claims, 10 Drawing Sheets

(56) References Cited

FOREIGN PATENT DOCUMENTS

| WO | 2006/021544 A1 | 3/2006 |
|---|---|---|
| WO | 2008/005570 A1 | 1/2008 |
| WO | 2008/109178 A1 | 9/2008 |
| WO | 2008/109179 A1 | 9/2008 |
| WO | 2008/148790 A1 | 12/2008 |
| WO | 2009/005801 A1 | 1/2009 |
| WO | 2009/005802 A1 | 1/2009 |
| WO | 2009/012375 A2 | 1/2009 |
| WO | 2009/073683 A2 | 6/2009 |
| WO | 2009/156421 A1 | 12/2009 |
| WO | 2010/045303 A2 | 4/2010 |
| WO | 2010/063802 A1 | 6/2010 |
| WO | 2010/091543 A1 | 8/2010 |
| WO | 2010/131145 A1 | 11/2010 |
| WO | 2010/131147 A1 | 11/2010 |
| WO | 2012/001076 A1 | 1/2012 |
| WO | 2012/080456 A1 | 6/2012 |
| WO | 2012/080457 A1 | 6/2012 |
| WO | 2013/030803 A1 | 3/2013 |
| WO | 2013/061002 A1 | 5/2013 |
| WO | 2013/061004 A1 | 5/2013 |
| WO | 2013/061005 A1 | 5/2013 |
| WO | 2013/174947 a1 | 11/2013 |
| WO | 2016/079049 A1 | 5/2016 |

OTHER PUBLICATIONS

Asadollahi, Tahereh et al., "QSAR Models for CXCR2 Receptor Antagonists Based on the Genetic Algorithm for Data Preprocessing Prior to Application of the PLS Linear Regression Method and Design of the New Compounds Using In Silico Virtual Screening," *Molecules* (Feb. 25, 2011); 16:1928-1955.

Barbosa, Maria Leticia de Castro et al., "Therapeutic approaches for tumor necrosis factor inhibition," *Brazilian Journal of Pharmaceutical Sciences* (Jul./Sep. 2011; accepted for pub May 25, 2011); 47:427-446.

Biju, Purakkattle et al., "3,4-Diamino-2,5-thiadiazole-1-oxides as potent CXCR2/CXCR1 antagonists," *Bioorganic & Medicinal Chemistry Letters* (2008; available online Oct. 30, 2007); 18:228-231.

Biju, Purakkattle et al., "Fluoroalkyl α side chain containing 3,4-diamino-cyclobutenediones as potent and orally bioavailable CXCR2-CXCR1 dual antagonists," *Bioorganic & Medicinal Chemistry Letters* (available online Jan. 15, 2009); 19:1431-1433.

Biju, Purakkattle et al., "3,4-Diamino-1,2,5-thiadiazole as potent and selective CXCR2 antagonists," *Bioorganic & Medicinal Chemistry Letters* (available online Jan. 15, 2009); 19:1434-1437.

Busch-Petersen, Jakob et al., "Phenol-containing antagonists of the CXCR2 receptor," *Expert Opin. Ther. Patents* (published online May 26, 2008); 18(6):629-637.

Chao, Jianhua et al., "C(4)-alkyl substituted furanyl cyclobutenediones as potent, orally bioavailable CXCR2 and CXCR1 receptor antagonists," *Bioorganic & Medicinal Chemistry Letters* (available online Apr. 10, 2007); 17:3778-3783.

Dwyer, Michael P. et al., "Discovery of 2-Hydrozy-N,N-dimethyl-3-{2-[[(R)-1-(5-methylfuran-2-yl)propyl]amino]-3,4-dioxo-cyclobut-1-enylamino}benzamide (SCH 527123): A Potent, Orally Bioavailable CXCR2/CXCR1 Receptor Antagonist," *J. Med. Chem.* (Aug. 9, 2006); 49(26):7603-7606.

Ebsworth, Karen et al., "Chemokine Receptor Inhibition as a Novel Therapeutic Approach for Psoriasis," *Poster No. 521* ChemoCentryx, Inc., Mountain View, CA (May 12, 2016); 2 pages.

Gunda, Shravan Kumar et al., "Structural investigations of CXCR2 receptor antagonists by CoMFA, CoMSIA and flexible docking studies," *Acta Pharm* (Jul. 17, 2012); 62:287-304.

Lai, Gaifa et al., "Synthesis and structure-activity relationships of new disubstiuted phenyl-containing 3,4-diamino-3-cyclobutene-1,2-diones as CXCR2 receptor antagonists," *Bioorganic & Medicinal Chemistry Letters* (available online Feb. 10, 2008); 18:1864-1868.

Liu, Shilan et al., "Design, synthesis, and evaluation of novel 3-amino-4-hydrazine-cyclobut-3-ene-1,2-diones as potent and selective CXCR2 chemokine receptor antagonists," *Bioorganic & Medicinal Chemistry Letters* (available online Aug. 7, 2009); 19:5741-5745.

McCleland, Brent W. et al., "Comparison of N,N'-diarylsquaramides and N,N'-diarylureas as antagonists of the CXCR2 chemokine receptor," *Bioorganic & Medicinal Chemistry Letters* (2007; available online Dec. 23, 2006); 17:1713-1717.

Merritt, J. Robert et al., "Synthesis and structure-activity relationships of 3,4-diaminocyclobut-3-ene-1,2-dione CXCR2 antagonists," *Bioorganic & Medicinal Chemistry Letters* (available online May 11, 2006); 16:4107-4110.

Nieuwenhuis, S. A. M. et al., "Structure of the $Y_D$ Tyrosine Radical in Photosystem II. Determination of the Orientation of the Phenoxyl Ring by Enantioselective Deuteration of the Methylene Group," *J. Am. Chem. Soc.* (Jan. 16, 1998); 120:829-830.

Wijtmans, Maikel et al., "Therapeutic targeting of chemokine receptors by small molecules," *Drug Discovery Today: Technologies* (2012; http://dx.doi.org/10.1016/j.ddtec.2012.03.004); 9(4):e229-e236.

Yu, Younong et al., "Synthesis and structure-activity relationships of heteroaryl substituted-3,4-diamino-3-cyclobut-3-ene-1,2-dione CXCR2/CXCR1 receptor antagonists," *Bioorganic & Medicinal Chemistry Letters* (available online Jan. 11, 2008); 18:1318-1322.

Zhang, Shuang et al., "Comparative Analysis of Pharmacophore Features and Quantitative Structure-Activity Relationships for CD38 Covalent and Non-covalent Inhibitors," *Chemical Biology & Drug Design* (Dec. 2015; first published Jul. 14, 2015); 86(6):1411-1424.

Zhou, Yi et al., "Design, Synthesis and Biological Evaluation of Noncovalent Inhibitors of Human CD38 NADase," *ChemMedChem* (Feb. 6, 2012); 7(2):223-228.

FIGURE 1A

| | | CXCR2 IC$_{50}$ (nM) |
|---|---|---|
| 1.001 | | +++ |
| 1.002 | | +++ |
| 1.003 | | + |
| 1.004 | | ++ |
| 1.005 | | + |
| 1.006 | | +++ |

FIGURE 1C
| 1.013 | 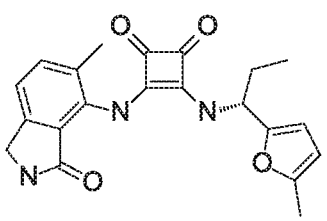 | +++ |
| --- | --- | --- |
| 1.014 | 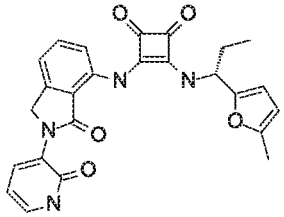 | +++ |
| 1.015 | 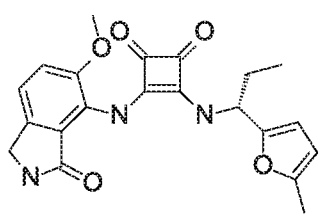 | ++ |
| 1.016 | 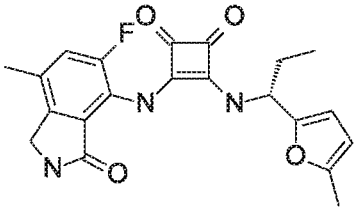 | +++ |
| 1.017 | 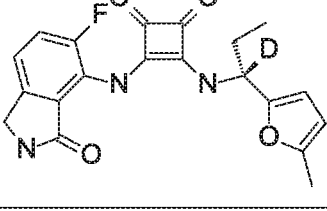 | +++ |
| 1.018 | 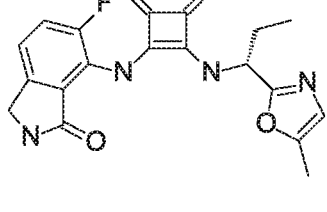 | ++ |

FIGURE 1D

| | | |
|---|---|---|
| 1.019 | | +++ |
| 1.020 | | ++ |
| 1.021 | | +++ |
| 1.022 | | +++ |
| 1.023 | | +++ |
| 1.024 | | +++ |

FIGURE 1E
| | | |
|---|---|---|
| 1.025 | 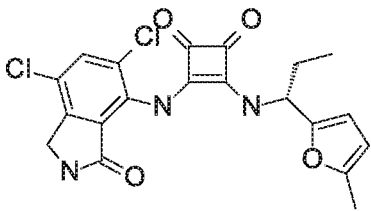 | +++ |
| 1.026 | 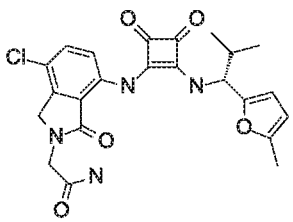 | +++ |
| 1.027 | 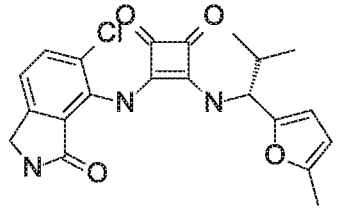 | +++ |
| 1.028 | 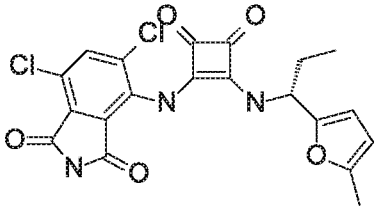 | +++ |
| 1.029 | 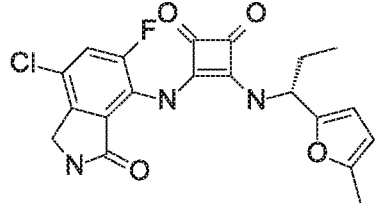 | +++ |
| 1.030 | 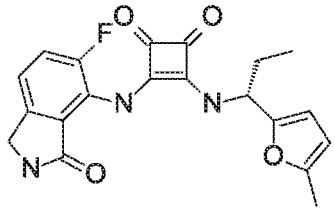 | +++ |

FIGURE 1F
| 1.031 | 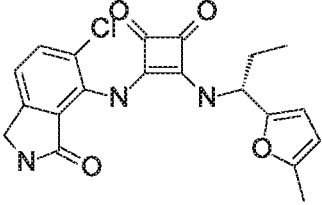 | +++ |
|---|---|---|
| 1.032 | 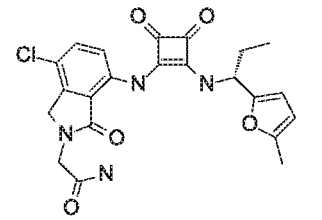 | +++ |
| 1.033 | 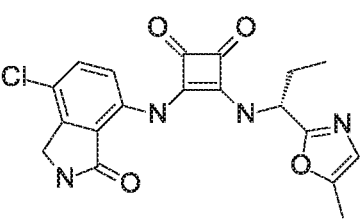 | +++ |
| 1.034 | 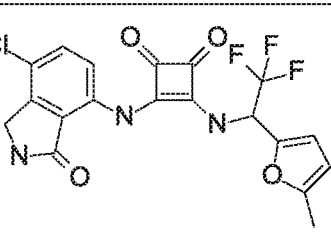 | +++ |
| 1.035 | 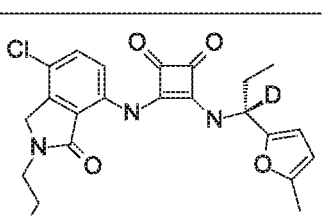 | +++ |
| 1.036 | 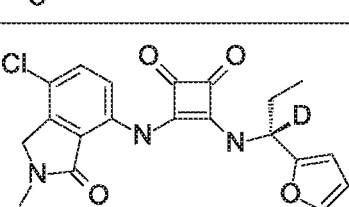 | +++ |

FIGURE 1G

| | | |
|---|---|---|
| 1.037 | *[structure]* | +++ |
| 1.038 | *[structure]* | +++ |
| 1.039 | *[structure]* | +++ |
| 1.040 | *[structure]* | +++ |
| 1.041 | *[structure]* | +++ |
| 1.042 | *[structure]* | ++ |

FIGURE 1H
| 1.043 | 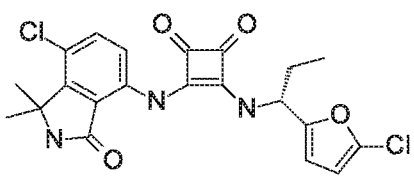 | +++ |
|---|---|---|
| 1.044 | 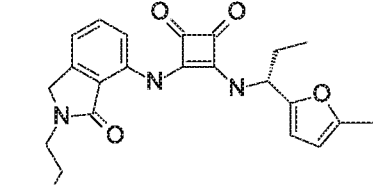 | ++ |
| 1.045 | 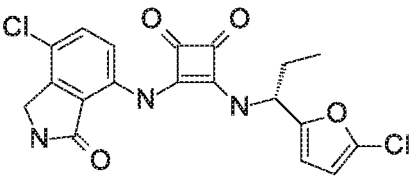 | +++ |
| 1.046 | 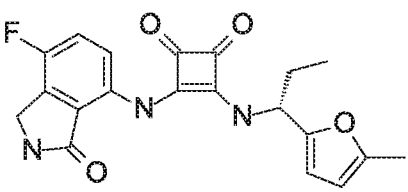 | +++ |
| 1.047 | 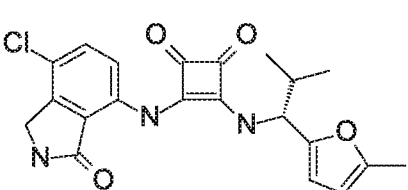 | +++ |
| 1.048 | 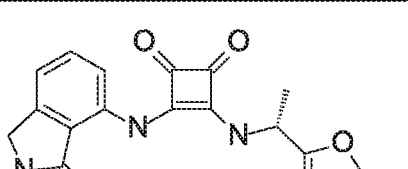 | ++ |

FIGURE 11

| | | |
|---|---|---|
| 1.049 | (structure: 7-chloro-isoindolin-1-one linked via N to squarate, linked via N to (S)-1-(5-methylfuran-2-yl)propyl) | +++ |
| 1.050 | (structure: isoindolin-1-one linked via N to squarate, linked via N to (S)-2-methyl-1-(5-methylfuran-2-yl)propyl) | +++ |
| 1.051 | (structure: isoindolin-1-one linked via N to squarate, linked via N to (S)-1-(5-methylfuran-2-yl)propyl) | +++ |

FIGURE 1J

| 1.052 | [structure] | +++ |
|---|---|---|
| 1.053 | [structure] | ++ |
| 1.054 | [structure] | +++ |
| 1.055 | [structure] | +++ |

INHIBITORS OF CXCR2

CROSS-REFERENCES TO RELATED APPLICATIONS

This application is a continuation of U.S. patent application Ser. No. 15/353,949 filed Nov. 17, 2016, which is an application claiming benefit under 35 U.S.C. § 119(e) of U.S. Provisional Application No. 62/257,529 filed Nov. 19, 2015, each of which is herein incorporated by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Chemokines are chemotactic cytokines that are released by a wide variety of cells, to attract cells such as leukocytes (including macrophages, T-cells, eosinophils, basophils, neutrophils and myeloid-derived suppressor cells) and endothelial cells to sites of inflammation and tumor growth. There are two main classes of chemokines, the CXC-chemokines and the CC-chemokines. The class depends on whether the first two cysteines are adjacent (CC-chemokines), or are separated by a single amino acid (CXC-chemokines). There are currently at least 17 known CXC-chemokines, which include but are not limited to CXCL1 (GROα), CXCL2 (GROβ), CXCL3 (GROγ), CXCL4 (PF4), CXCL5 (ENA-78), CXCL6 (GCP-2, CXCL7 (NAP-2), CXCL8 (IL-8, NAP-1), CXCL9 (MIG) and CXCL10 (IP-10). There are currently at least 28 known CC chemokines, which include but are not limited to CCL2 (MCP-1), CCL3 (MIP-1α), CCL4 (MIP-1β), CCL5 (RANTES), CCL7 (MCP-3), CCL8 (MCP-2), CCL-11 (eotaxin-1) and CCL20 (MIP-3 α). Individual members of the chemokine families are known to be bound by at least one chemokine receptor, with CXC-chemokines generally bound by members of the CXCR class of receptors, and CC-chemokines by members of the CCR class of receptors. For example, CXCL8/IL-8 is bound by the receptors CXCR1 and CXCR2.

Since CXC-chemokines often promote the accumulation and activation of neutrophils, these chemokines are implicated in a wide range of acute and chronic inflammatory disorders such as psoriasis, rheumatoid arthritis, radiation-induced fibrotic lung disease, autoimmune bullous dermatoses (AIBD), chronic obstructive pulmonary disease (COPD) and ozone-induced airway inflammation (see, Baggiolini et al., *FEBS Lett.* 307:97 (1992); Miller et al., *Crit. Rev. Immunol.* 12:17 (1992); Oppenheim et al., *Anmn. Rev. Immunol.* 9: 617 (1991); Seitz et al., *J. Clin. Invest.* 87: 463 (1991); Miller et al., *Ann. Rev. Respir. Dis.* 146:427 (1992); and Donnely et al., *Lancet* 341: 643 (1993), Fox & Haston, *Radiation Oncology,* 85:215 (2013), Hirose et al., *J. Genet. Syndr. Genet. Ther*. S3:005 (2013), Miller et al., *Eur. J. Drug Metab. Pharmacokinet.* 39:173 (2014), Lazaar et al., *Br. J. Clin. Pharmacol.,* 72:282 (2011)).

A subset of CXC chemokines, those which contain the ELR motif (ELR-CXC), have been implicated in the induction of tumor angiogenesis (new blood vessel growth). These include the CXCR2 ligand chemokines CXCL-1, CXCL2, CXCL3, CXCL5 and (Strieter et al. *JBC* 270: 27348-27357 (1995)) Some CXCR2 ligand ELR-CXC chemokines are exacerbating agents during ischemic stroke (Connell et al., *Neurosci. Lett.,* 15:30111 (2015). All of these chemokines are believed to exert their actions by binding to CXCR2. Thus, their angiogenic activity is due to their binding and activation of CXCR2 expressed on the surface of vascular endothelial cells (ECs) in surrounding vessels.

Many different types of tumors are known to produce ELR-CXC chemokines, and production of these chemokines correlates with a more aggressive phenotype (Inoue et al. *Clin Cancer Res* 6:2104-2119 (2000)) and poor prognosis (Yoneda et. al. *J Nat Cancer Inst* 90:447-454 (1998)). As ELR-CXC chemokines are potent chemotactic factors for EC chemotaxis, they probably induce chemotaxis of endothelial cells toward their site of production in the tumor. This may be a critical step in the induction of tumor angiogenesis. Inhibitors of CXCR2 will inhibit the angiogenic activity of the ELR-CXC chemokines and therefore block the tumor growth. This anti-tumor activity has been demonstrated for antibodies to CXCL8 (Arenberg et al. *J Clin Invest* 97:2792-2802 (1996)), ENA-78 (Arenberg et al. *J Clin Invest* 102:465-72 (1998)), and CXCL1 (Haghnegahdar et al. *J. Leukoc Biology* 67:53-62 (2000)).

Many tumor cells express CXCR2 and tumor cells may thereby stimulate their own growth by secreting ELR-CXC chemokines. Thus, in addition to with decreasing angiogenesis within tumors, CXCR2 inhibitors may directly inhibit the growth of tumor cells.

CXCR2 is often expressed by myeloid-derived suppressor cells (MDSC) within the microenvironment of tumors. MDSC are implicated in the suppression of tumor immune responses, and migration of MDSC in response to CXCR2 ligand chemokines is most likely responsible for attracting these cells into tumors. (see Marvel and Gabrilovich, *J. Clin. Invest.* 13:1 (2015) and Mackall et al., *Sci. Trans. Med.* 6:237 (2014). Thus, CXCR2 inhibitors may reverse suppressive processes and thereby allow immune cells to more effectively reject the tumor. In fact, blocking the activation of CXC-chemokine receptors has proven useful as a combination therapy with checkpoint inhibitors in suppressing tumor growth, suggesting that CXCR2 blockade may also enhance tumor rejection in combination with other anti-tumor therapies, including but not limited to vaccines or traditional cytotoxic chemotherapies (see Highfill et al., *Science Translational Medicine,* 6:237 (2014)).

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

BRIEF SUMMARY OF THE INVENTION

Provided herein, in one aspect, are compounds having formula (I),

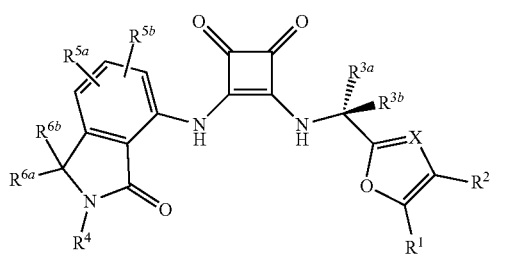

In formula (I) above, and herein, $R^1$ and $R^2$ are each members independently selected from the group consisting of H, halogen, CN, $C_{1-4}$ alkyl, $C_{1-4}$ alkoxy and $C_{1-4}$ haloalkyl; $R^{3a}$ is a member selected from the group consisting of methyl, ethyl, propyl, isopropyl, trifluoromethyl, $CH_2CF_3$ and $CF_2CF_3$; $R^{3b}$ is a member selected from the group consisting of H and D; $R^4$ is a member selected from the group consisting of H, $C_{1-8}$ alkyl, —Y and $C_{1-4}$alkylene-Y; wherein Y is aryl or heteroaryl, and each $R^4$ is optionally substituted with from one to four substituents selected from the group consisting of halogen, —CN, —$CO_2R^a$, —$CONR^aR^b$, —$C(O)R^a$, —$OC(O)NR^aR^b$, $NR^aC(O)R^b$, $NR^aC(O)_2R^c$, —$NR^aC(O)NR^aR^b$, —$NR^aR^b$, —$OR^a$, —$S(O)_2NR^aR^b$, —$NR^aS(O)_2R^b$, and —$R^c$, wherein each $R^a$ and $R^b$ is independently selected from hydrogen, $C_{1-4}$ alkyl, $C_{1-4}$ hydroxyalkyl and $C_{1-4}$ haloalkyl, $R^c$ is selected from $C_{1-4}$ alkyl, $C_{1-4}$ hydroxyalkyl and $C_{1-4}$ haloalkyl; $R^{5a}$ and $R^{5b}$ are each members independently selected from the group consisting of H, halogen, $C_{1-4}$ alkyl, $C_{1-4}$ alkoxy and CN; $R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O); X is CH or N; or any salts, solvates, hydrates, N-oxides, tautomers or rotamers thereof.

The compounds provided herein are useful for selectively binding to, and inhibiting the activity of CXCR2, and treating diseases that are dependent, at least in part, on CXCR2 activity. Accordingly, the present invention provides in further aspects, compositions containing one or more of the above-noted compounds in admixture with a pharmaceutically acceptable excipient.

In still another aspect, provided herein are methods for treating various diseases, discussed further herein, comprising administering to a subject in need to such treatment a therapeutically effective amount of a compound of the above formula for a period of time sufficient to treat the disease.

In yet another aspect, provided herein are methods of diagnosing disease in an individual. In these methods, the compounds provided herein are administered in labeled form to a subject, followed by diagnostic imaging to determine the presence or absence of CXCR2. In a related aspect, a method of diagnosing disease is carried out by contacting a tissue or blood sample with a labeled compound as provided herein and determining the presence, absence, or amount of CXCR2 in the sample.

In some embodiments, an amount of a chemotherapeutic agent or radiation is administered to the subject prior to, subsequent to or in combination with the compounds provided herein. In some embodiments, the amount is sub-therapeutic when the chemotherapeutic agent or radiation is administered alone.

BRIEF DESCRIPTION OF THE DRAWINGS

Figure 1A:
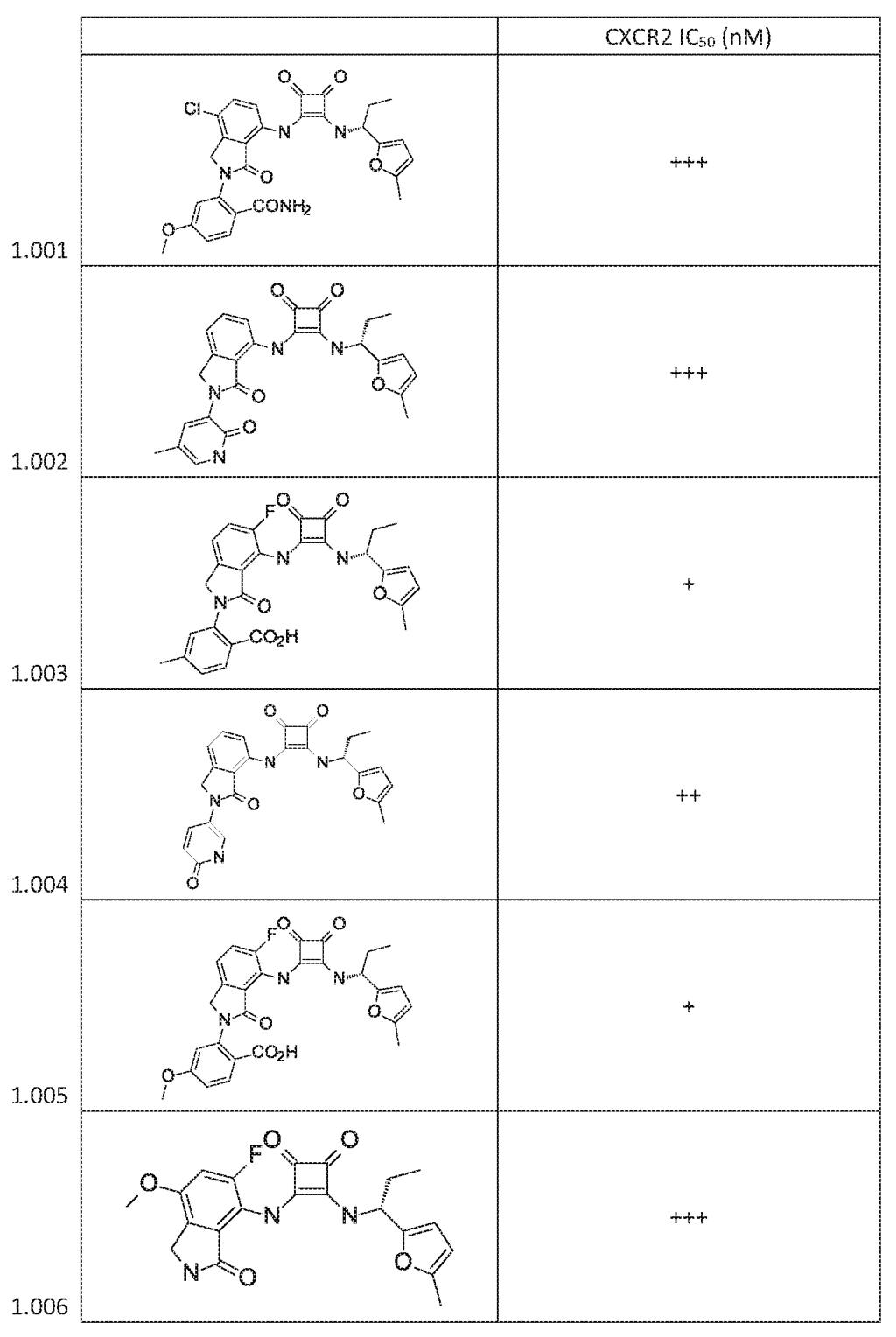

FIGS. 1A-1J provide structures and biological activity for compounds described herein.

DETAILED DESCRIPTION OF THE INVENTION

Figure 1B:
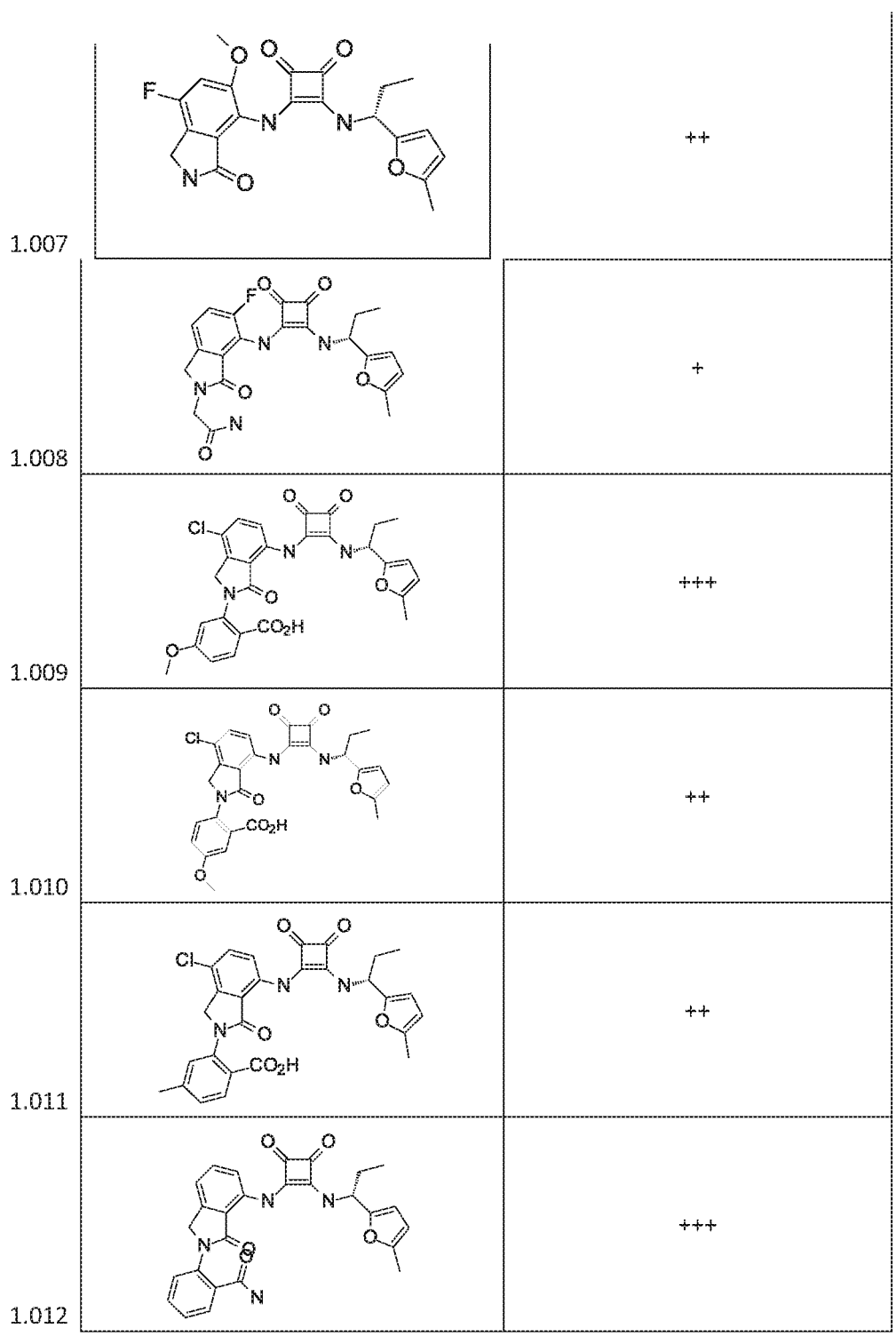

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

General

The present invention derives from the discovery that compounds of formula I act as potent and selective antagonists of the CXCR2 receptor. The compounds have in vivo anti-inflammatory activity and have superior pharmacokinetic properties. Accordingly, the compounds provided herein are useful in pharmaceutical compositions, methods for the treatment of CXCR2-mediated diseases, and as controls in assays for the identification of competitive CXCR2 antagonists.

Abbreviation And Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "cycloalkenyl" refers to a cycloalkyl group having at least one double bond between ring vertices. Examples of cycloalkenyl are cyclopentenyl and cyclohexenyl. The term "spirocycloalkyl" refers to a cycloalkyl group in which a single ring vertex is attached to two other non-hydrogen portions of the molecule. A spirocycloalkyl substituent is one in which two carbon atoms of an alkylene chain (typically the termini of the alkylene chain) are attached to the same carbon atom in the remainder of the molecule. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "⁓", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R"' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1}$-4 alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

When a variable (e. g., $R^1$ or $R^a$) occurs more than one time in any constituent, its definition on each occurrence is independent of its definition at every other occurrence. Additionally, combinations of substituents and/or variables are permissible only if such combinations result in stable compounds.

The term "pharmaceutically acceptable salts" is meant to include salts of the active compounds which are prepared with relatively nontoxic acids or bases, depending on the particular substituents found on the compounds described herein. When compounds provided herein contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds provided herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds provided herein contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds provided herein. Additionally, prodrugs can be converted to the compounds provided herein by chemical or biochemical methods in an ex vivo environment. For example, prodrugs can be slowly converted to the compounds provided herein when placed in a transdermal patch reservoir with a suitable enzyme or chemical reagent.

Certain compounds provided herein can exist in unsolvated forms as well as solvated forms, including hydrated forms. In general, the solvated forms are equivalent to unsolvated forms and are intended to be encompassed within the scope of the present invention. Certain compounds provided herein may exist in multiple crystalline or amorphous forms. In general, all physical forms are equivalent for the uses contemplated by the present invention and are intended to be within the scope of the present invention.

Certain compounds provided herein possess asymmetric carbon atoms (optical centers) or double bonds; the racemates, diastereomers, geometric isomers, regioisomers and individual isomers (e.g., separate enantiomers) are all intended to be encompassed within the scope of the present invention. In some embodiments, the compounds of the invention are present in an enantiomerically enriched form, wherein the amount of enantiomeric excess for a particular enantiomer is calculated by known methods. The preparation of enantiomerically enriched forms is also well known in the art and can be accomplished using, for example, chiral resolution via chromatography or via chiral salt formation. When a particular stereochemical depiction is shown herein, it is meant to refer to that form of the compound in the stereochemistry is as shown and is substantially free of the other isomer. 'Substantially free of' another isomer indicates at least an 80/20 ratio of the two isomers, more preferably 90/10, or 95/5 or more. In some embodiments, one of the isomers will be present in an amount of at least 99%. Additionally, different conformers are contemplated by the present invention, as well as distinct rotamers. Conformers are conformational isomers that can differ by rotations about one or more σ bonds. Rotamers are conformers that differ by rotation about only a single σ bond. Still further, the compounds provided herein may also contain unnatural proportions of atomic isotopes at one or more of the atoms that constitute such compounds. Accordingly, in some embodiments, the compounds of the invention are present in isotopically enriched form. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds provided herein, whether radioactive or not, are intended to be encompassed within the scope of the present invention. Certain compounds provided herein are shown in one tautomeric form (e.g., a pyridone form), which is understood by one of skill in the art to include the shown form as well as the other tautomeric form (e.g., a hydroxyl-pyridine).

"CXCR2" refers to CXC Chemokine Receptor 2, also known as CD128, IL8RB and IL8 receptor type B, whose gene is encoded on human chromosome 2q35 and is a known receptor for CXCL1, CXCL2, CXCL3, CXCL5, CXCL6, CXCL7 and CXCL8 (see Murphy, P. M., *Annu. Rev. Immumol.* 12:593 (1994) and Zlotnik & Yoshie, *Immunity*, 12:127 (2000)).

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of CXCR2, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of CXCR2 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a CXCR2 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an CXCR2 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CXCR2, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

Embodiments of the Invention

A. Compounds

Provided herein, in one aspect, are compounds having formula (I),

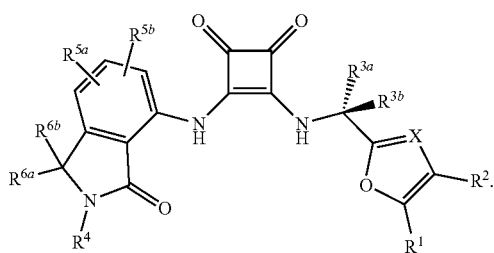

In formula (I) above, and herein, $R^1$ and $R^2$ are each members independently selected from the group consisting of H, halogen, CN, $C_{1-4}$ alkyl, $C_{1-4}$ alkoxy and $C_{1-4}$ haloalkyl; $R^{3a}$ is a member selected from the group consisting of methyl, ethyl, propyl, isopropyl, trifluoromethyl, $CH_2CF_3$ and $CF_2CF_3$; $R^{3b}$ is a member selected from the group consisting of H and D; $R^4$ is a member selected from the group consisting of H, $C_{1-8}$ alkyl, —Y and $C_{1-8}$ alkylene-Y; wherein Y is aryl or heteroaryl, and each $R^4$ is optionally substituted with from one to four substituents selected from the group consisting of halogen, —CN, —$CO_2R^a$, —$CONR^aR^b$, —$C(O)R^a$, —$OC(O)NR^aR^b$, $NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$, and —$R^c$, wherein each $R^a$ and $R^b$ is independently selected from hydrogen, $C_{1-4}$ alkyl, $C_{1-4}$ hydroxyalkyl and $C_{1-4}$ haloalkyl, $R^c$ is selected from $C_{1-4}$ alkyl, $C_{1-4}$ hydroxyalkyl and $C_{1-4}$ haloalkyl; $R^{5a}$ and $R^{5b}$ are each members independently selected from the group consisting of H, halogen, $C_{1-4}$ alkyl, $C_{1-4}$ alkoxy and CN; $R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O); X is CH or N; or any salts, solvates, hydrates, N-oxides, tautomers or rotamers thereof.

Selected embodiments are those in which (1) $R^1$ is selected from H, Cl and $CH_3$; or (2) $R^2$ is H; or (3) $R^{3a}$ is ethyl or isopropyl; or (4a) $R^{3b}$ is H; or (4b) $R^{3b}$ is D; or (5) X is CH; or (6) each of $R^{5a}$ and $R^{5b}$ are independently selected from H, Cl and F; or (7) each of $R^{6a}$ and $R^{6b}$ are independently selected from H and $C_{1-4}$ alkyl; or (8) $R^4$ is $C_{1-8}$ alkyl, optionally substituted with -halogen, —CN, —$CO_2R^a$, —$CONR^aR^b$, —$C(O)R^a$, —$OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, and —$NR^aS(O)_2R^b$. Combinations of two or more, three or more, four or more, or five or more of embodiments (1) through (8) are also contemplated as further selected embodiments.

In further selected embodiments, compounds are provided having formula (Ia):

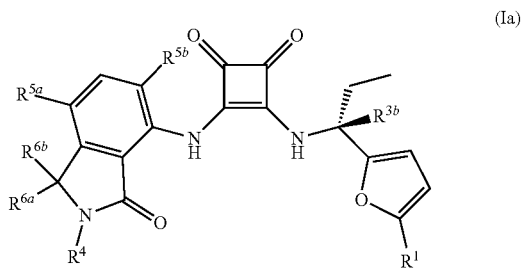

wherein $R^1$ is selected from the group consisting of Cl and $CH_3$; $R^{3b}$ is selected from the group consisting of H and D; $R^4$ is a member selected from the group consisting of H and $C_{1-8}$ alkyl, wherein the $C_{1-8}$alkyl is optionally substituted with —$CONR^aR^b$, —$OC(O)NR^aR^b$, —$NR^aC(O)R^b$, —$NR^aC(O)_2R^c$, —$NR^aR^b$, or —$OR^a$, wherein each $R^a$ and $R^b$ is independently selected from hydrogen, $C_{1-4}$ alkyl, $C_{1-4}$ hydroxyalkyl and $C_{1-4}$ haloalkyl, and $R^c$ is selected from $C_{1-4}$ alkyl, $C_{1-4}$ hydroxyalkyl and $C_{1-4}$ haloalkyl; $R^{5a}$ and $R^{5b}$ are each members independently selected from the group consisting of H, F, Cl and $CH_3$; $R^{6a}$ and $R^{6b}$ are each members independently selected from the group consisting of H, $C_{1-4}$ alkyl, $C_{1-4}$ hydroxyalkyl and $C_{1-4}$ haloalkyl; or optionally $R^{6a}$ and $R^{6b}$ are taken together to form oxo (=O); or any salts, solvates, hydrates, N-oxides or rotamers thereof.

Within formula (Ia), further selected embodiments are those in which $R^{3b}$ is H; $R^4$ is H or CH; $R^{5a}$ is H, F or Cl; $R^{5b}$ is H, F, Cl; $R^{6a}$ and $R^{6b}$ are independently selected from the group consisting of H and $CH_3$, or are taken together to form oxo (=O).

Within formula (Ia), still other selected embodiments are those in which $R^{3b}$ is D; $R^4$ is H or $CH_3$; $R^{5a}$ is H, F or Cl; $R^{5b}$ is H, F, Cl; $R^{6a}$ and $R^{6b}$ are independently selected from the group consisting of H and $CH_3$, or are taken together to form oxo (=O).

In other selected embodiments, compounds are provided having formula (Ib):

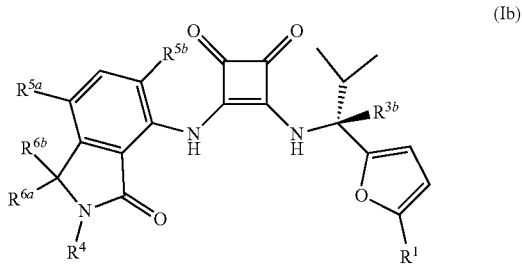

wherein R¹ is selected from the group consisting of Cl and CH₃; R³ᵇ is selected from the group consisting of H and D; R⁴ is a member selected from the group consisting of H and C₁₋₈ alkyl, wherein the C₁₋₈ alkyl is optionally substituted with —CONRᵃRᵇ, —OC(O)NRᵃRᵇ, —NRᵃC(O)Rᵇ, —NRᵃC(O)₂Rᶜ, —NRᵃRᵇ, or —ORᵃ, wherein each Rᵃ and Rᵇ is independently selected from hydrogen, C₁₋₄ alkyl, C₁₋₄ hydroxyalkyl and C₁₋₄ haloalkyl, and Rᶜ is selected from C₁₋₄ alkyl, C₁₋₄ hydroxyalkyl and C₁₋₄ haloalkyl; R⁵ᵃ and R⁵ᵇ are each members independently selected from the group consisting of H, F, Cl and CH₃; R⁶ᵃ and R⁶ᵇ are each members independently selected from the group consisting of H, C₁₋₄ alkyl, C₁₋₄ hydroxyalkyl and C₁₋₄ haloalkyl; or optionally R⁶ᵃ and R⁶ᵇ are taken together to form oxo (=O); or any salts, solvates, hydrates, N-oxides or rotamers thereof.

Within formula (Ib), further selected embodiments are those in which R³ᵇ is H; R⁴ is H or CH₃; R⁵ᵃ is H, F or Cl; R" is H, F, Cl; R⁶ᵃ and R⁶ᵇ are independently selected from the group consisting of H and CH₃, or are taken together to form oxo (=O).

Within formula (Ib), still other selected embodiments are those in which R³ᵇ is D; R⁴ is H or CH₃; R⁵ᵃ is H, F or Cl; R⁵ᵇ is H, F. Cl; R⁶ᵃ and R⁶ᵇ are independently selected from the group consisting of H and CH₃, or are taken together to form oxo (=O).

In another selected group of embodiments, the compound is selected from those provided in the Examples below, or in Table 1.

In each of the selected embodiments, the noted compounds may be present in a pharmaceutically acceptable salt or hydrate form.

In some embodiments, a compound or a pharmaceutically acceptable salt thereof is provided selected from the group consisting of:

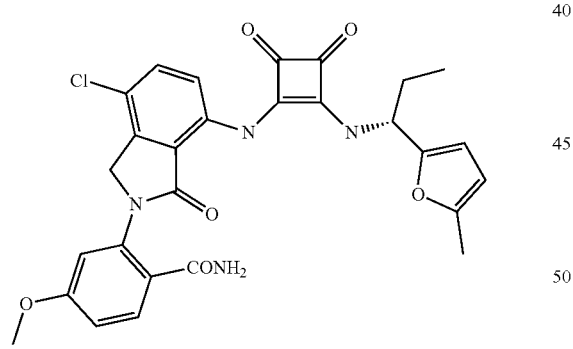

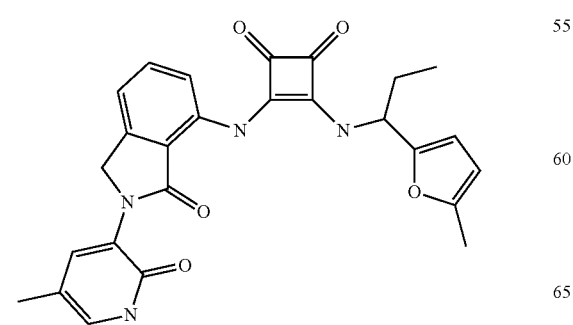

-continued

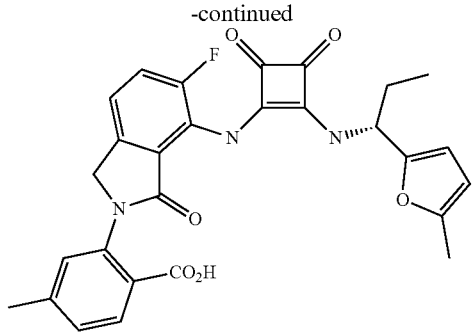

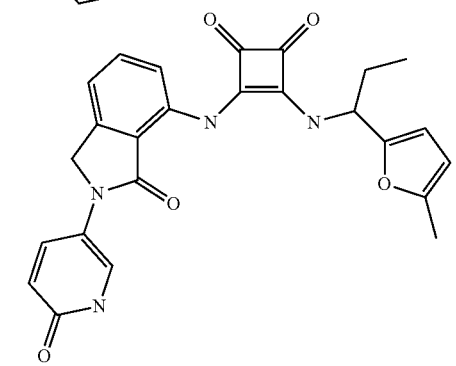

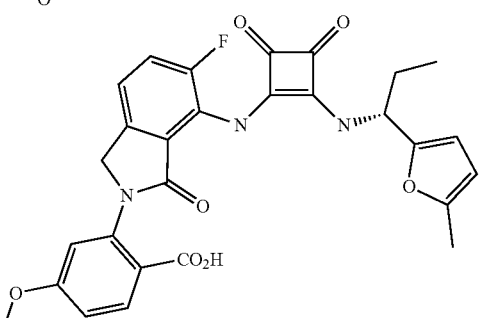

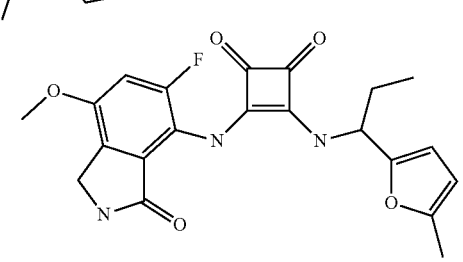

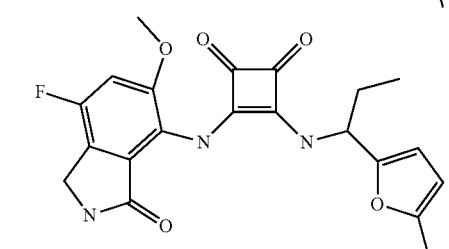

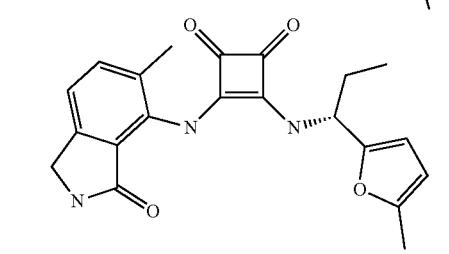

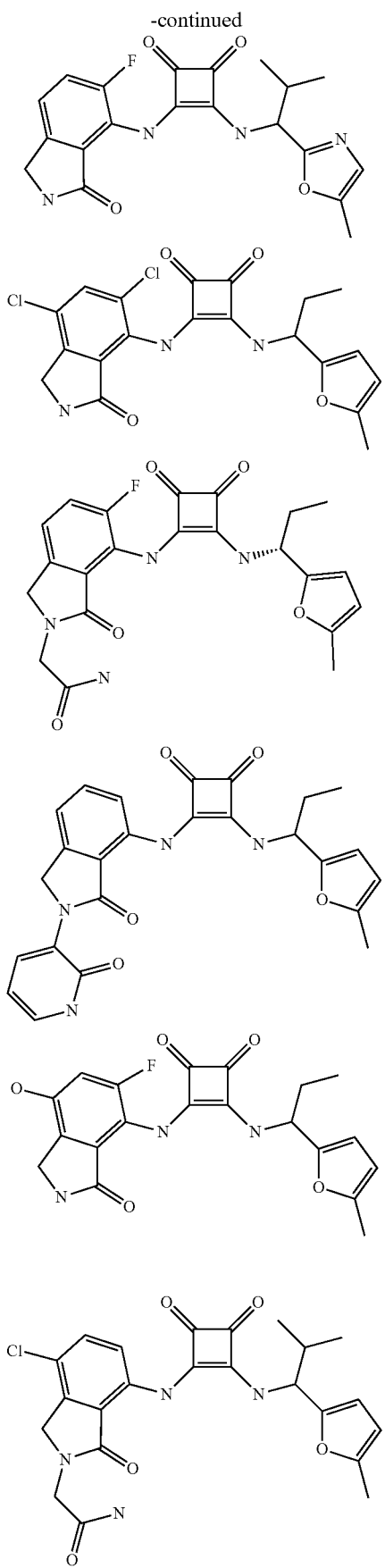
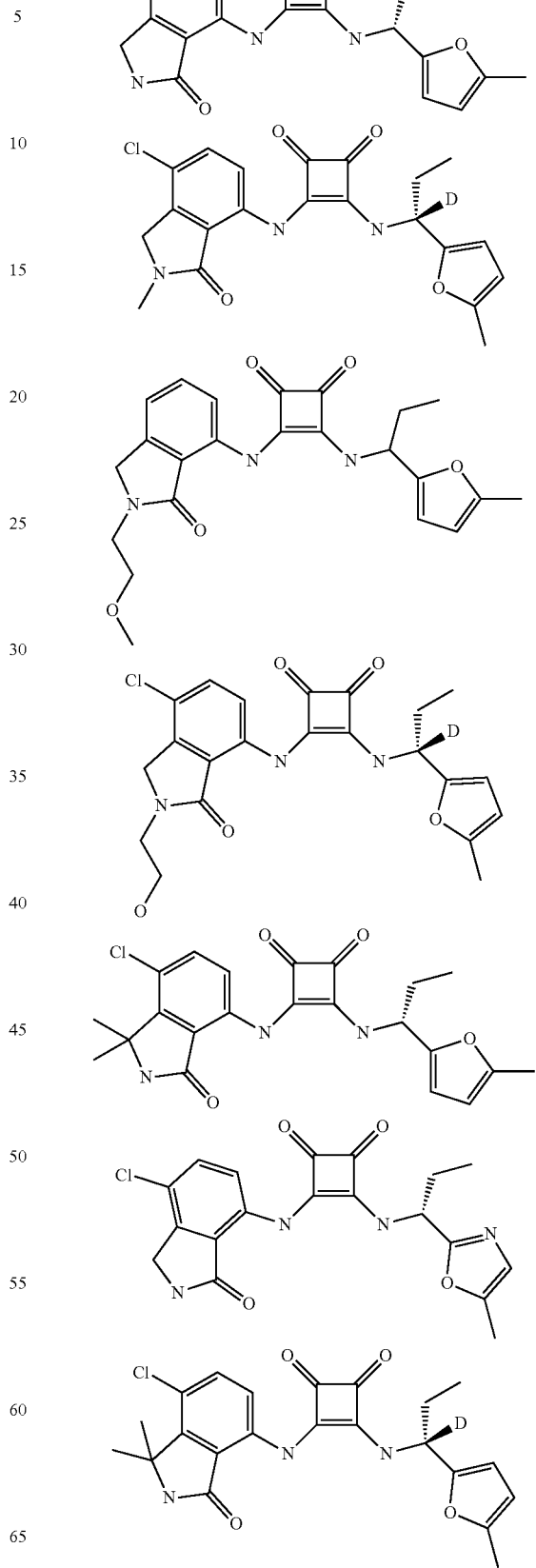

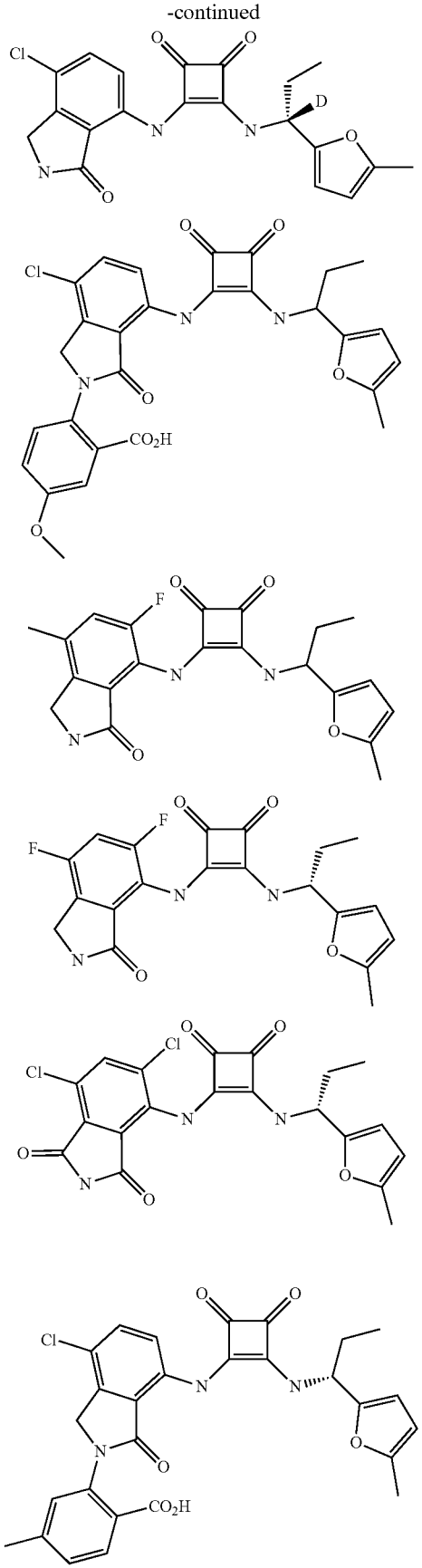

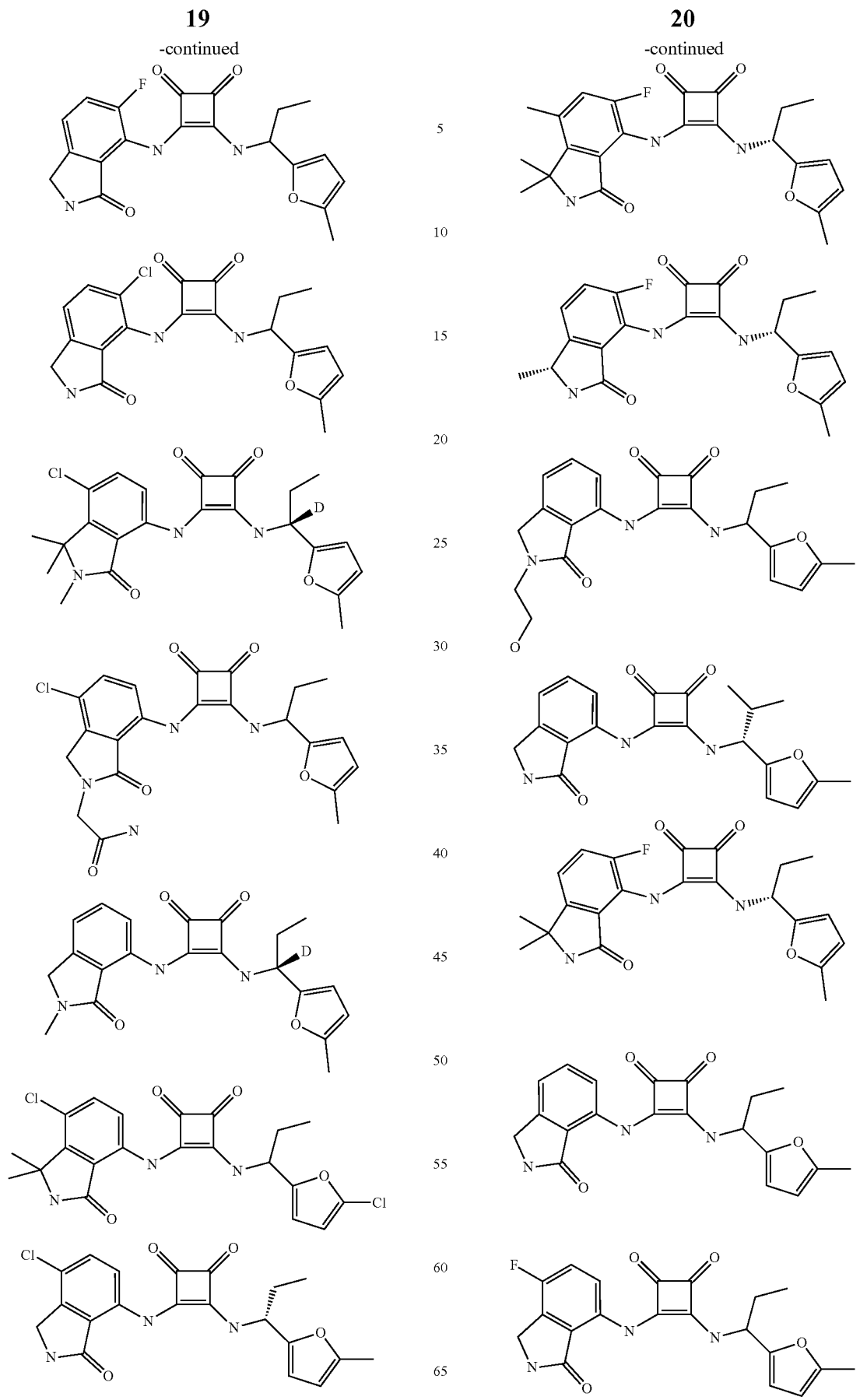

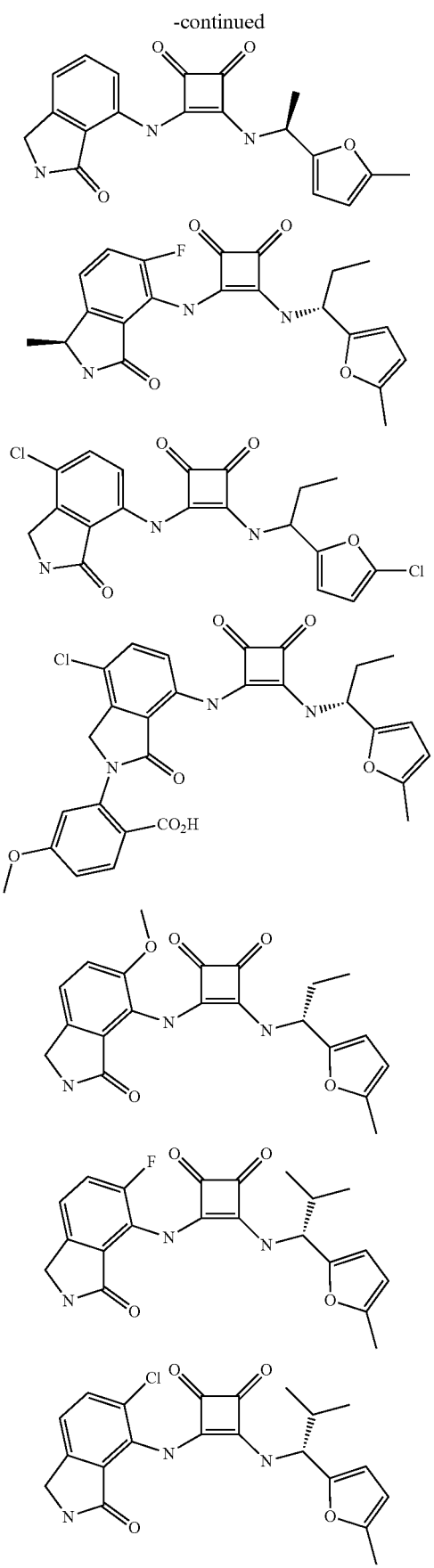
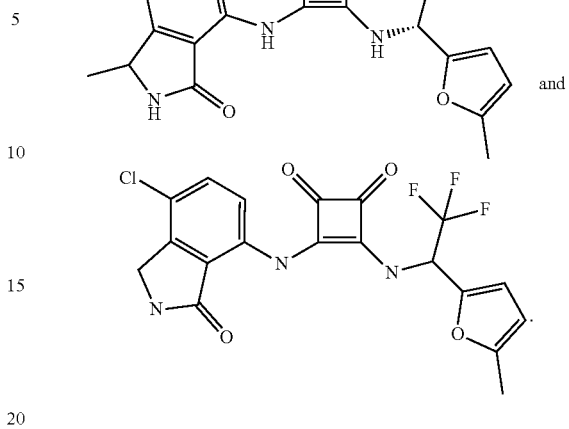

Still further, for those compounds shown above without stereochemistry, the present invention is also directed to chiral forms of each of the compounds, as well as enantiomerically enriched forms of the noted compounds. Enantiomerically enriched forms can be prepared using chiral chromatography according to well-known methods practiced in the art or, for example, by chiral resolution with a chiral salt form. In some embodiments, the enantiomeric excess for an enantiomerically enriched form is at least 10%, 20%°, 30%, 400%, 50%, 60% or more. In still other embodiments, an enantiomerically enriched form is provided that is at least 70%, 80%, 90%, 95%, or more.

Preparation of Compounds

Certain compounds of the invention can be prepared following methodology as described in the Examples section of this document. In addition the syntheses of certain intermediate compounds that are useful in the preparation of compounds of the invention are also described.

B. Compositions

In addition to the compounds provided above, compositions for modulating CXCR2 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds provided herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds provided herein are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

A pharmaceutical composition comprising a compound of the present disclosure is provided. In some embodiments, the pharmaceutical composition further comprises one or more additional therapeutic agents. In some embodiments, the one or more additional therapeutic agent is selected from the group consisting of a cytotoxic chemotherapy, anticancer or anti-tumor vaccines, anti-immunocytokine therapies, immunocytokine therapies, chimeric antigen receptor (CAR) T cell receptors, gene transfer therapy, and checkpoint inhibitors. In some embodiments, the one or more additional therapeutic agent is selected from the group consisting of: drugs that block the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

C. Methods of Use

While not wishing to be bound by any particular theory, the compounds and compositions provided herein are considered to provide a therapeutic effect by inhibiting the CXCR2 receptor. Therefore, the compounds and compositions provided herein can be used in the treatment or prevention of diseases or disorders in a mammal in which the inhibition of the CXCR2 receptor would provide a therapeutic effect.

Another aspect of the invention is the use of a compound as provided herein and/or the pharmaceutically acceptable salt and/or a prodrug thereof alone or in combination with other medicaments or active ingredients as for producing a medicament for the treatment or prophylaxis of a chemokine mediated disease, wherein the chemokine binds to a CXCR2 receptor.

Accordingly, provided herein are methods directed to the use of a compound of formula I and/or a pharmaceutically acceptable salt and/or a prodrug thereof alone or in combination with other medicaments or active ingredients as for producing a medicament for the treatment or prophylaxis of rheumatoid arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium aspriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, Alzheimer's disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post-surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyper-responsiveness, bronchiolitis, bronchiolitis obliterans, bronchiolitis obliterans organizing pneumonia, bronchiectasis, chronic bronchitis, corpulmonae, dyspnea, emphysema, hypercapnea, hyperinflation, hyperoxia-induced inflammations, hypoxemia, hypoxia, lung ischemia/reperfusion injury, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovascularization, tumor angiogenesis, cancer and metastasis.

In particular, the invention further relates to the use of a compound of the formula I and/or a pharmaceutically acceptable salt and/or a prodrug thereof alone or in combination with other medicaments or active ingredients as for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, Alzheimer's disease, malaria, viral infections, traumatic brain injury, pulmonary fibrosis, and cancer.

In some embodiments, the compounds and compositions of the invention are administered to a subject having cancer. In some cases, CXCR2 inhibitors are administered to treat cancer, e.g., carcinomas, gliomas, mesotheliomas, melanomas, lymphomas, leukemias (including acute lymphocytic leukemias), adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, renal cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER: PRINCIPLES AND PRACTICE (DeVita, V.

T. et al. eds 1997) for additional cancers); as well as brain and neuronal dysfunction, such as Alzheimer's disease, multiple sclerosis and demyelinating diseases; hypertensive disorders such as pulmonary arterial hypertension; kidney dysfunction; renal dysfunction; rheumatoid arthritis; allograft rejection; atherosclerosis (and elevated cholesterol levels); asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma.

In some embodiments, a method of treating a CXCR2-mediated disease or condition in a subject in need thereof is provided, said method comprising administering an effective amount of a compound of the present disclosure, or a pharmaceutically acceptable salt thereof, or a pharmaceutical composition of the present disclosure to said subject. In some embodiments, the CXCR2-mediated disease is an acute or chronic inflammatory disorder. In some embodiments, the CXCR2-mediated acute or chronic inflammatory disorder is selected from the group consisting of psoriasis, rheumatoid arthritis, radiation induced fibrotic lung disease, autoimmune bullous dermatosis (AIBD), chronic obstructive pulmonary disease, and ozone-induced airway inflammation.

In some embodiments, a compound of the present disclosure, or a pharmaceutically acceptable salt thereof, is used to treat cancer alone or in combination with one or more other anti-cancer therapies. In some embodiments, a compound of the present disclosure or a pharmaceutically acceptable salt thereof, is used to treat cancer in combination with one or more of a cytotoxic chemotherapy, an anti-cancer vaccine, an anti-tumor vaccines, an anti-immunocytokine, an immunocytokine therapy, and a chimeric antigen receptor (CAR) T cell receptors, gene transfer therapy. In some embodiments, a compound of the present disclosure or a pharmaceutically acceptable salt thereof, is used to treat cancer in combination with one or more checkpoint inhibitor. In some embodiments, a compound of the present disclosure is used to treat cancer in combination with one or more of an anti-cancer therapy selected from the group consisting of drugs that block the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

In some embodiments, the compounds of the disclosure, or a pharmaceutically acceptable salt and/or a prodrug thereof, or compositions of the disclosure are administered to treat melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and/or fibroma.

Other disorders involving unwanted or problematic angiogenesis include rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; disease of excessive or abnormal stimulation of endothelial cells, including intestinal adhesions, Crohn's disease, skin diseases such as psoriasis, eczema, and scleroderma, diabetes, diabetic retinopathy, retinopathy of prematurity, age-related macular degeneration, atherosclerosis, scleroderma, wound granulation and hypertrophic scars, i.e., keloids, and diseases that have angiogenesis as a pathologic consequence such as cat scratch disease and ulcers (*Helicobacter pylori*), can also be treated with antibodies of the invention. Angiogenic inhibitors can be used to prevent or inhibit adhesions, especially intra-peritoneal or pelvic adhesions such as those resulting after open or laparoscopic surgery, and burn contractions. Other conditions which should be beneficially treated using the angiogenesis inhibitors include prevention of scarring following transplantation, cirrhosis of the liver, pulmonary fibrosis following acute respiratory distress syndrome or other pulmonary fibrosis of the newborn, implantation of temporary prosthetics, and adhesions after surgery between the brain and the dura. Endometriosis, polyposis, cardiac hypertrophy, as well as obesity, may also be treated by inhibition of angiogenesis. These disorders may involve increases in size or growth of other types of normal tissue, such as uterine fibroids, prostatic hypertrophy, and amyloidosis. Compounds and compositions provided herein may be used prophylactically or therapeutically for any of the disorders or diseases described herein.

In some embodiments, the compounds of the disclosure, or a pharmaceutically acceptable salt and/or a prodrug thereof, or compositions of the disclosure are administered to treat cystitis, insulin dependent diabetes, islet cell transplant rejection; kidney transplant rejection; liver transplant rejection; lung transplant rejection, COPD, or influenza.

Methods of Treating Cancer

More specifically, the present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions provided herein may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In some embodiments, selective CXCR2 inhibitors provided herein can be administered in combination with other appropriate therapeutic agents, including, e.g., chemotherapeutic agents, radiation, etc. It is understood that such administration may be prior to, subsequent to or in unison with the second therapeutic agent, such that the therapeutic effects of the second agent are enhanced when compared to administration of the second agent in the absence of the CXCR2 inhibitor. Selection of the appropriate agents for use in combination therapy may be made by one of ordinary skill in the art, according to conventional pharmaceutical principles. The combination of therapeutic agents may act synergistically to effect the treatment or prevention of the various disorders such as, e.g., cancer, wounds, kidney dysfunction, brain dysfunction or neuronal dysfunction. Using this approach, one may be able to achieve therapeutic efficacy with lower dosages of each agent, thus reducing the potential for adverse side effects.

In addition to primates, such as humans, a variety of other mammals can be treated according to the method provided herein. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions provided herein are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma*. Blood. No. 1. Vol. 96, pp. 282-87 (1 Jul. 2000); Pengnian, L., *Antiangiogenic gene therapy targeting the endothelium-specific receptor tyrosine kinase Tie2*. Proc. Natl. Acad. Sci. USA, Vol. 95, pp. 8829-34 (July 1998); and Pulaski, B. *Cooperativity of Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model*. Cancer Research, Vol. 60, pp. 2710-15 (May 15, 2000).

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions provided herein can be combined with other compounds and compositions having related utilities to prevent and treat cancer and diseases or conditions associated with CXCR2 signaling. Such other drugs may be administered, by a route and in an amount commonly used therefor, contemporaneously or sequentially with a compound or composition provided herein. When a compound or composition provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition provided herein. Examples of other therapeutic agents that may be combined with a compound or composition provided herein, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound provided herein to the second active ingredient may be varied and will depend upon the effective dose of each ingredient. Generally, an effective dose of each will be used. Thus, for example, when a compound provided herein is combined with a second anticancer agent, the weight ratio of the compound provided herein to the second agent will generally range from about 1000:1 to about 1:1000, preferably about 200:1 to about 1:200. Combinations of a compound provided herein and other active ingredients will generally also be within the aforementioned range, but in each case, an effective dose of each active ingredient should be used. In some embodiments, the compounds of the disclosure, or a pharmaceutically acceptable salt and/or a prodrug thereof, are administered either separately or in the same pharmaceutical compositions, with: an alkylation agent, a nitrosourea agent, an anticancer antibiotics, a vegetable-origin alkaloid, a topoisomerase inhibitor, an hormone drug, an hormone antagonist, an aromatase inhibitor, a P-glycoprotein inhibitor, a platinum complex derivative, an immunotherapeutic drug or another anticancer drugs, or any combination thereof.

Methods of Treating Inflammation

Still further, the compounds and compositions provided herein are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non-sedating antihistamine.

As noted, compounds and compositions provided herein may be used in combination with other drugs that are used in the treatment, prevention, suppression or amelioration of the diseases or conditions for which compounds and compositions provided herein are useful. Such other drugs may be administered, by a route and in an amount commonly used therefor, contemporaneously or sequentially with a compound or composition as provided herein. When a compound or composition as provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition as provided herein. Examples of other therapeutic agents that may be combined with a compound or composition provided herein, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and rnycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, rniroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (1) other antagonists of the chemokine receptors, especially CCR5, CXCR2, CXCR3, CCR2, CCR3, CCR4, CCR7, $CX_3CRI$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound provided herein to the second active ingredient may be varied and will depend upon the effective dose of each ingredient. Generally, an effective dose of each will be used. Thus, for example, when a compound provided herein is combined with an NSAID the weight ratio of the compound provided herein to the NSAID will generally range from about 1000:1 to about 1:1000, preferably about 200:1 to about 1:200. Combinations of a compound provided herein and other active ingredients will generally also be within the aforementioned range, but in each case, an effective dose of each active ingredient should be used.

Method of Diagnosing Diseases and Disorders Associated with CXCR2

Still further, the compounds and compositions provided herein are useful for the diagnosis of diseases and disorders associated with CXCR2. In particular, the compounds provided herein can be prepared in a labeled form (e.g., radiolabeled) and used for the diagnosis of, for example, cancer. Labeled compounds provided herein that bind to CXCR2 (e.g., antagonists or agonists) can be used to determine levels of CXCR2 in a mammalian subject. In some embodiments, the CXCR2 modulators or antagonists are administered to a subject having cancer. In some cases, labeled compounds are administered to detect developing cancers, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER: PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis (and elevated cholesterol levels); asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma.

A variety of imaging and detection methods can be used for the detection of cancers. In some embodiments, direct methods are available to evaluate CXCR2 biodistribution in the body such as magnetic resonance imaging ("MRI"), positron emission tomography ("PET"), and single photon emission computed tomography ("SPECT"). Each of these methods can detect the distribution of a suitably labeled compound (generally as bound to CXCR2) within the body if that compound contains an atom with the appropriate nuclear properties. MRI detects paramagnetic nuclei; PET and SPECT detect the emission of particles from the decay of radionuclei.

For methods involving PET, it is necessary to incorporate an appropriate positron-emitting radionuclide. There are relatively few positron-emitting isotopes that are suitable for labeling a therapeutic agent. The carbon isotope, $^{11}C$, has been used for PET, but has a short half-life of 20.5 minutes. Accordingly, the facilities for synthesis and use are typically near to a cyclotron where the precursor $^{11}C$ starting material is generated. Another useful isotope, $^{18}F$, has a half-life of 110 minutes. This allows sufficient time for incorporation into a radiolabeled tracer, for purification and for administration into a human or animal subject. Other isotopes have even shorter half-lives. $^{13}N$ has a half-life of 10 minutes and $^{15}O$ has an even shorter half-life of 2 minutes. The emissions of both are more energetic, however, than those of $^{11}C$ and PET studies have been carried out with these isotopes (see, Clinical Positron Emission Tomography, Mosby Year Book, 1992, K. F. Hubner, et al., Chapter 2).

SPECT imaging employs isotope tracers that are γ-emitters. While the range of useful isotopes is greater than for PET, imaging with SPECT provides lower three-dimensional resolution. However, in some instances, SPECT is used to obtain clinically significant information about compound binding, localization and clearance rates. One useful isotope for SPECT imaging is $^{123}I$, a γ-emitter with a 13.3 hour half-life. Compounds labeled with $^{123}I$ can be shipped up to about 1000 miles from the manufacturing site, or the isotope itself can be transported for on-site synthesis. Eighty-five percent of the isotope's emissions are 159 KeV photons, which are readily measured by SPECT instrumentation currently in use. Other halogen isotopes can serve for PET or SPECT imaging, or for conventional tracer labeling. These include $^{75}Br$, $^{76}Br$, Br and $^{82}Br$ as having usable half-lives and emission characteristics.

In view of the above, the present invention provides methods for imaging a tumor, organ, or tissue, said method comprising:
 (a) administering to a subject in need of such imaging, a radiolabeled or detectable form of a compound of Formula I; and
 (b) detecting said compound to determine where said compound is concentrated in said subject.

Additionally, the present invention provides methods for detecting elevated levels of CXCR2 in a sample, said method comprising:
 (a) contacting a sample suspected of having elevated levels of CXCR2 with a radiolabeled or detectable form of a compound of Formula I;
 (b) determining a level of compound that is bound to CXCR2 present in said sample to determine the level of CXCR2 present in said sample; and
 (c) comparing the level determined in step (b) with a control sample to determine if elevated levels of CXCR2 are present in said sample.

As with the treatment methods described herein, administration of the labeled compounds can be by any of the routes normally used for introducing a compound into ultimate contact with the tissue to be evaluated and is well known to those of skill in the art. Although more than one route can be used to administer a particular composition, a particular route can often provide a more immediate and more effective diagnosis than another route.

Combination Therapies

Inhibitors of CXCR2 can be supplied alone or in conjunction with one or more other drugs. Possible combination partners can include, e.g., additional anti-angiogenic factors and/or chemotherapeutic agents (e.g., cytotoxic agents) or radiation, a cancer vaccine, an immunomodulatory agent, a checkpoint inhibitor, an anti-vascular agent, a signal transduction inhibitor, an antiproliferative agent, or an apoptosis inducer.

Examples of other therapeutic agents that may be combined with a compound or composition of the present disclosure, either administered separately or in the same pharmaceutical composition, include, but are not limited to: modulators of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX3CRI, ChemR23, C5aR, C5a, and C5, or any combination thereof. In some embodiments, the modulator is an antagonist.

Examples of other therapeutic agents that may be combined with a compound or composition of the present disclosure, either administered separately or in the same pharmaceutical compositions, include, but are not limited to: a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, cytokines, vaccines, vaccine adjuvants, GM-CSF, M-CSF, G-CSF, interferon-a, beta, or gamma, IL-1, L-2, IL-3, IL-12, Poly (I:C), CPG, cyclophosphamide, analogs of cyclophosphamide, anti-TGF and imatinib (Gleevac), a mitosis inhibitor paclitaxel, Sunitinib (Sutent), antiangiogenic agents, an aromatase inhibitor, letrozole, an A2a adenosine receptor (A2AR) antagonist, an adenosine receptor modulator, an A3 adenosine receptor modulator, an angiogenesis inhibitor, anthracyclines, oxaliplatin, doxorubicin, TLR4 antagonists, IL-18 antagonists, a Btk tyrosine kinase inhibitor, an Erbb2 tyrosine kinase receptor inhibitor; an Erbb4 tyrosine kinase receptor inhibitor, an mTOR inhibitor, a Thymidylate synthase inhibitor, an EGFR tyrosine kinase receptor inhibitor, an Epidermal growth factor antagonist, a Fyn tyrosine kinase inhibitor, a Kit tyrosine kinase inhibitor, a Lyn tyrosine kinase inhibitor, a NK cell receptor modulator, a PDGF receptor antagonist, a PARP inhibitor, a Poly ADP ribose polymerase inhibitor, a Poly ADP ribose polymerase 1 inhibitor, a Poly ADP ribose polymerase 2 inhibitor, a Poly ADP ribose polymerase 3 inhibitor, a Galactosyltransferase modulator, a Dihydropyrimidine dehydrogenase inhibitor, an Orotate phosphoribosyltransferase inhibitor, a Telomerase modulator, a Mucin 1 inhibitor, a Mucin inhibitor, a Secretin agonist, a TNF related apoptosis inducing ligand modulator, an IL17 gene stimulator, an Interleukin 17E ligand, a Neurokinin receptor agonist, a Cyclin GI inhibitor, a checkpoint inhibitor, a PD-1 inhibitor, a PD-L1 inhibitor, a CTLA4 inhibitor, a Topoisomerase I inhibitor, an Alk-5 protein kinase inhibitor, a Connective tissue growth factor ligand inhibitor, a Notch-2 receptor antagonist, a Notch-3 receptor antagonist, a Hyaluronidase stimulator, a MEK-1 protein kinase inhibitor, a Phosphoinositide-3 kinase inhibitor, a MEK-2 protein kinase inhibitor, a GM-CSF receptor modulator; TNF alpha ligand modulator, a Mesothelin modulator, an Asparaginase stimulator, a CSF2 gene stimulator, a Caspase-3 stimulator; Caspase-9 stimulator, a PKN3 gene inhibitor, a Hedgehog protein inhibitor; Smoothened receptor antagonist, an AKT1 gene inhibitor, a DHFR inhibitor, a Thymidine kinase stimulator, a CD29 modulator, a Fibronectin modulator, an Interleukin-2 ligand, a Serine protease inhibitor, a D40LG gene stimulator; TNFSF9 gene stimulator, a 2 oxoglutarate dehydrogenase inhibitor, a TGF-beta type II receptor antagonist, an Erbb3 tyrosine kinase receptor inhibitor, a Cholecystokinin CCK2 receptor antagonist, a Wilms tumor protein modulator, a Ras GTPase modulator, an Histone deacetylase inhibitor, a Raf B protein kinase inhibitor, a Cyclin-dependent kinase 4 inhibitor A modulator, an Estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a TIGIT inhibitor, a NKG2A inhibitor, a GAL9 inhibitor, a LAG3 inhibitor, a PD-1H inhibitor, a PD96 inhibitor, a VISTA inhibitor, a KIR inhibitor, a 2B4 inhibitor, a CD160 inhibitor, a CD66e modulator, an Angiotensin II receptor antagonist, a Connective tissue growth factor ligand inhibitor, a Jak1 tyrosine kinase inhibitor, a Jak2 tyrosine kinase inhibitor, a dual Jak1/Jak2 tyrosine kinase inhibitor, an Angiotensin converting enzyme 2 stimulator, a Growth hormone receptor antagonist, a Galectin-3 inhibitor, a Checkpoint kinase 2 modulator, a Sodium glucose transporter-2 inhibitor, a Endothelin ET-A antagonist, a Mineralocorticoid receptor antagonist, an Endothelin ET-B antagonist, an Advanced glycosylation product receptor antagonist, an Adrenocorticotrophic hormone ligand, a Farnesoid X receptor agonist, a G-protein coupled bile acid receptor 1 agonist, an Aldose reductase inhibitor, a Xanthine oxidase inhibitor, a PPAR gamma agonist, a Prostanoid receptor antagonist, a FGF receptor antagonist, a PDGF receptor antagonist, a TGF beta antagonist, a P3 protein modulator, a p38 MAP kinase inhibitor, a VEGF-1 receptor antagonist, a Protein tyrosine phosphatase beta inhibitor, a Tek tyrosine kinase receptor stimulator, a PDE 5 inhibitor, a Mineralocorticoid receptor antagonist, an ACE inhibitor, a I-kappa B kinase inhibitor, a NFE2L2 gene stimulator, a Nuclear factor kappa B inhibitor, a STAT3 gene inhibitor, a NADPH oxidase 1 inhibitor, a NADPH oxidase 4 inhibitor, a PDE 4 inhibitor, a Renin inhibitor, a FURIN gene inhibitor, a MEKK-5 protein kinase inhibitor, a Membrane copper amine oxidase inhibitor, an Integrin alpha-V/beta-3 antagonist, an Insulin sensitizer, a Kallikrein 1 modulator, a Cyclooxygenase inhibitor, a Complement $C_3$ modulator, a Tubulin binding agent, a Macrophage mannose receptor 1 modulator, a Phenylalanine hydroxylase stimulator, an OX40 agonist, a GITR agonist, a CD40 agonist, Denileukin diftitox, Bexarotene, Vorinostat, Romidepsin, Pralatrexate, prednisone, prednisolone, CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, CCX168-M1, bavituximab, IMM-101, CAPI-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, nab-paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX, KY-1003, olmesartan medoxomil, candesartan, PBI-4050, baricitinib, GSK-2586881, losartan, dapagliflozin propanediol, pegvisomant, GR-MD-02, canagliflozin, irbesartan, FG-3019, atrasentan, finerenone, sparsentan, bosentan, defibrotide, fimasartan, azeliragon, pyridoxamine, corticotropin, INT-767, epalrestat, topiroxostat, SER-150-DN, pirfenidone, VEGFR-1 mAb, AKB-9778, PF-489791, SHP-627, CS-3150, imidapril, perindopril, captopril, enalapril, lisinopril, Zofenopril, Lisinopril, Quinapril, Benazepril, Trandolapril, Cilazapril, Fosinopril, Ramipril, bardoxolone methyl, irbesartan+propagermanium, GKT-831, MT-3995, TAK-648, TAK-272, GS-4997, DW-1029M, ASP-8232, VPI-2690B, DM-199, rhein, PHN-033, GLY-230, and sapropterin, sulodexide, lirilumab, IPH-4102, IPH-2101, IMP-321, BMS-986016, MGD-013, LAG-525, durvalumab, monalizumab, MCLA-134, MBG-453, CA-170, AUPM-170, AUPM-327, resminostat, ipilimumab, BGB-A317, tremelimumab, REGN-2810, AZD-5069, masitinib, binimetinib, trametinib, ruxolitinib, dabrafenib, linaclotide, ipilimumab, apatinib, nintedanib, cabozantinib, pazopanib, belinostat, panitumumab, guadecitabine, vismodegib, vemurafenib, dasatinib, tremelimumab, bevacizumab, oxaliplatin, aflibercept, vandetanib, everolimus, thalidomide, veliparib, encorafenib, napabucasin, alpelisib, axitinib, cediranib, necitumumab, ramucirumab, irofulven, trifluridine+tipiracil, donafenib, pacritinib, pexastimogene devacirepvec, tivantinib, GNR-011, talaporfin, piclidenoson, decitabine, ganitumab, panobinostat, rintatolimod, polmacoxib, levofolinate, famitinib, votumumab, tivozanib, entinostat, plitidepsin, lefitolimod, OSE-2101, vitespen, TroVax, bromocriptine, midostaurin, fosbretabulin, fruquintinib, ganetespib, brivanib, anlotinib, L19-TNF-alpha, racotumomab, Novaferon, raltitrexed, enzastaurin, GM-CT-01, arcitumomab, or any combination thereof.

Kits and Packages

The terms "kit" and "pharmaceutical kit" refer to a commercial kit or package comprising, in one or more suitable containers, one or more pharmaceutical compositions and instructions for their use. In one embodiment, kits comprising a compound of Formula (I), or a pharmaceutically acceptable salt thereof, and instructions for its administration are provided. In one embodiment, kits comprising a compound of Formula (I), or a pharmaceutically acceptable salt thereof, in combination with one or more (e.g., one, two, three, one or two, or one to three) additional therapeutic agents and instructions for their administration are provided.

In one embodiment, the compounds of this disclosure are formulated into administration units which are packaged in a single packaging. The single packaging encompasses but is not limited to a bottle, a child-resistant bottle, an ampoule, and a tube. In one embodiment, the compounds of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

General Synthetic Procedure

The embodiments are also directed to processes and intermediates useful for preparing the subject compounds or pharmaceutically acceptable salts thereof.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Representative syntheses of compounds of the present disclosure are described in the schemes below, and the particular examples that follow. Schemes 1 and 2 are provided as further embodiment of the disclosure and illustrate general methods which were used to prepare compounds of the present disclosure including compounds of Formula (I), (Ia) and (Ib), and which can be used to prepare additional compounds having the Formula (I), (Ia), and (Ib). The methodology is compatible with a wide variety of functionalities.

Scheme 1

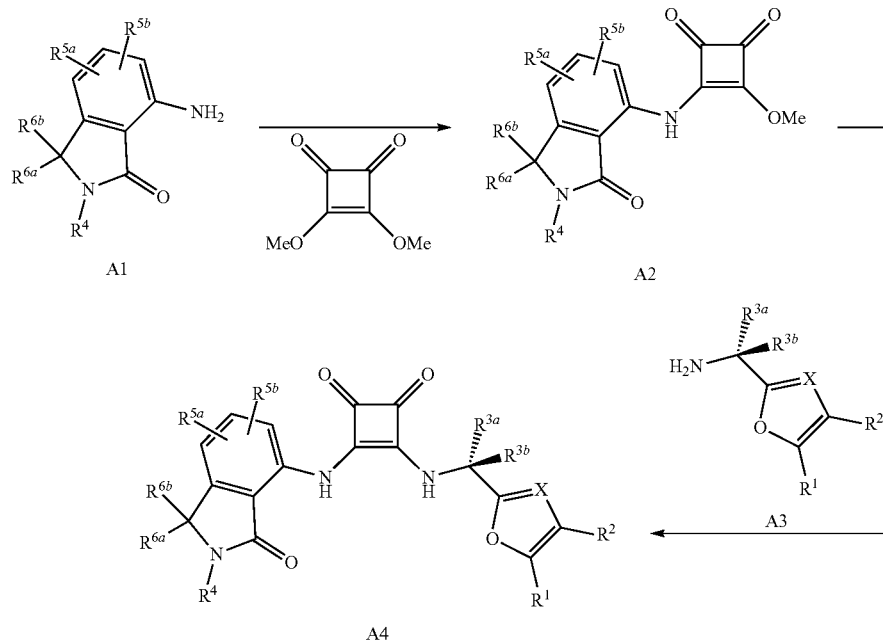

The amino group of A1 can be reacted with 3,4-dimethoxycyclobut-3-ene-1,2-dione to provide A2. A2 can then be reacted with the amino group of A3 to provide A4.

Scheme 2

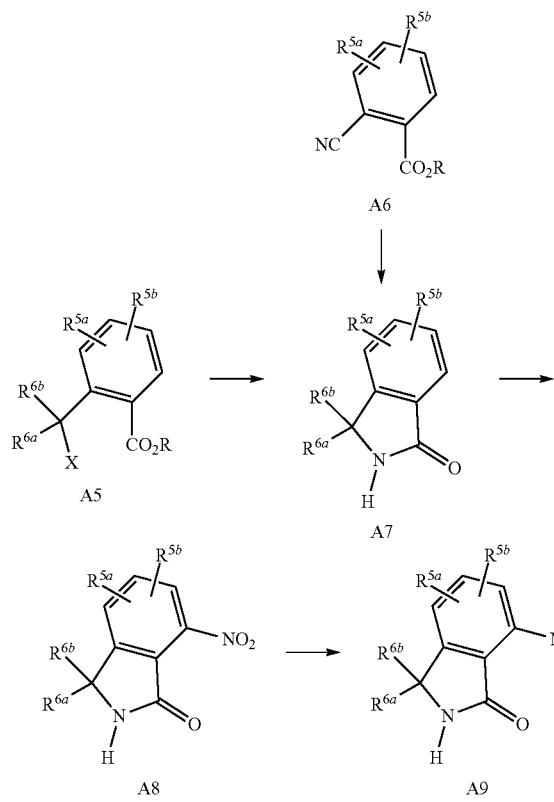

A7 can be obtained by reduction of the cyano group in A6, for example by hydrogenation, followed by cyclization. Alternatively, A5 (where X represents a leaving group such as a halogen or a tosylate and where R is an alkyl group), can be reacted with $NH_3$ to form the cyclized product A7. A7 can be reacted with $HNO_3$ to introduce the nitro group in presence of an acid such as sulfuric acid to give A8. Subsequent reduction of the nitro group in A8 by for example hydrogenation can provide A9.

EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M-H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP 1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; Pd$_2$dba$_3$, tris(dibenzylideneacetone) dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 3-[(5-fluoro-3-oxo-isoindolin-4-yl)amino]-4-[[(1R)-1-(5-methyl-2-furyl)propyl]amino]cyclobut-3-ene-1,2-dione

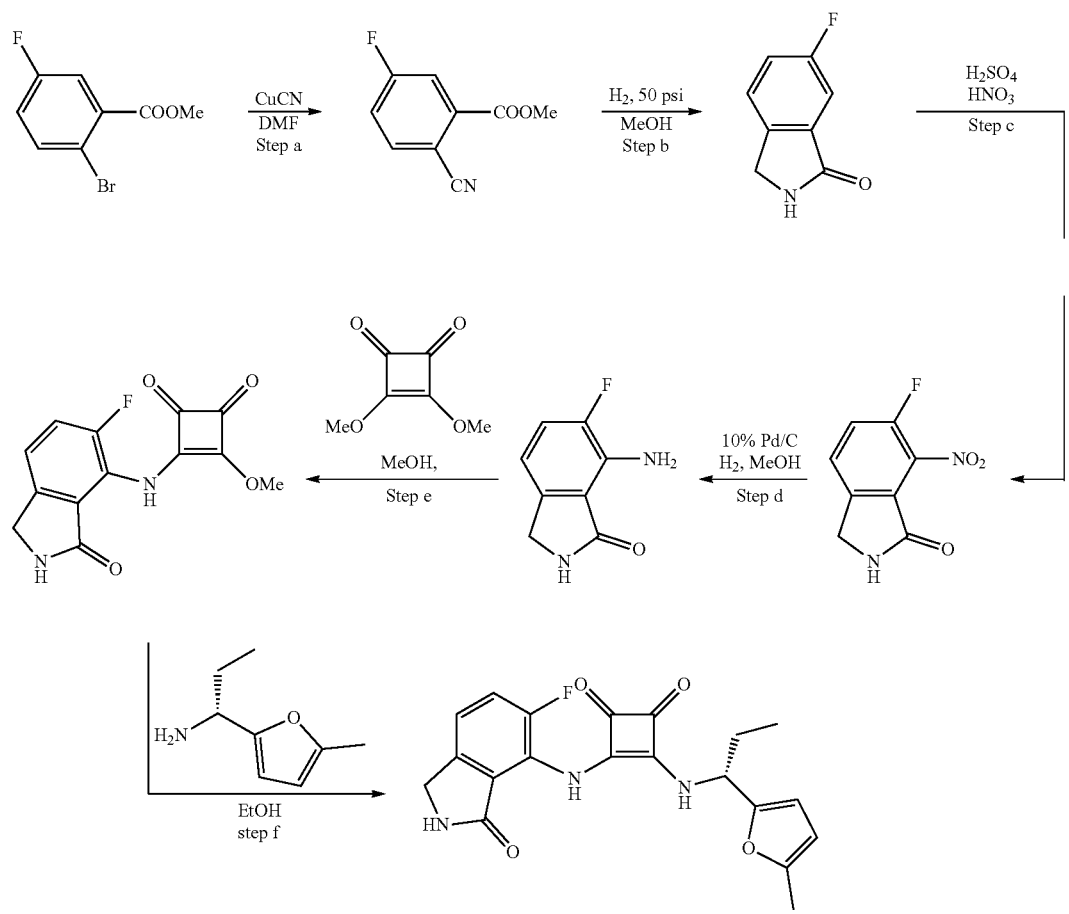

Step a: A 500 mL round-bottom flask was charged with methyl 2-bromo-5-fluorobenzoate (48 g, 206 mmol), copper cyanide (37 g, 412 mmol) and DMF (200 mL). The mixture was heated at 110° C. overnight and then cooled to room temperature. Ether (1.5 L) and Celite (100 g) were added and the mixture was stirred at room temperature for 30 minutes. The solid was filtered and the filtrate was washed with brine (3×200 mL) and then dried over MgSO$_4$. The solvent was evaporated under reduced pressure to give the desired product as a colorless solid (31 g, 84%). MS: (ES) m/z calculated for C$_9$H$_7$FNO$_2$ [M+H]$^+$ 180, found 180.

Step b: To a solution of methyl 2-cyano-5-fluorobenzoate (10 g, 56 mmol) in methanol (200 mL) was added 10% Pd—C (1.0 g) at room temperature. The resulting mixture was stirred under a hydrogen (50 psi) atmosphere overnight. The reaction mixture was filtered through Celite and the filtrate was concentrated under reduced pressure to give the desired product as a colorless solid (8.0 g, 90%). MS: (ES) m/z calculated for $C_8H_7FNO$ [M+H]$^+$ 152, found 152.

Step c: To a 0° C. suspension of 6-fluoroisoindoline-1-one (8.0 g, 5.3 mmol) in concentrated $H_2SO_4$ was added dropwise a pre-cooled mixture of concentrated $H_2SO_4$ (26 mL) and nitric acid (6 mL) while keeping the reaction mixture below 5° C. After addition, the reaction mixture was slowly warmed to room temperature during overnight. Ice (50 g) was added to the mixture and the solid was collected and dried, then washed with MTBE (50 mL) and ethyl acetate (50 mL) to give the desired product as a light yellow solid (5.1 g, 50%). MS: (ES) m/z calculated for $C_8H_6FN_2O_3$ [M+H]$^+$ 197, found 197.

Step d: A solution of 6-fluoro-7-nitroisoindolin-1-one (11.3 g, 57 mmol) and 10%/Pd/C (50% wet, 6.2 g, 2.9 mmol, 0.05 equiv) in THF (300 mL) was stirred under a hydrogen atmosphere (balloon) overnight. The solid was filtered through Celite and the filtrate was concentrated under reduced pressure to give a colorless solid, which was purified by silica gel chromatography (100% ethyl acetate) to give the desired product as a white solid (6.4 g, 67%). MS: (ES) m/z calculated for $C_8H_9FN_2O$ [M+H]$^+$ 168, found 168.

Step e: A mixture of 7-amino-6-difluoro-isoindolin-1-one (4.4 g, 26 mmol) and 3,4-dimethoxycyclobut-3-ene-1,2-dione (7.4 g, 52 mmol) in anhydrous methanol (30 mL) was stirred at 60° C. for overnight and then at 80° C. for 5 h. The reaction mixture was evaporated and the residue was stirred in ethyl acetate (200 mL) at 50° C. for 30 min, then cooled down to room temperature. The mixture was filtered and dried to give a light yellow color solid (5.0 g, 70%). MS: (ES) m/z calculated for $C_{13}H_{10}FN_2O_4$ [M+H]$^+$ 277, found 277.

Step f: A 20 mL vial was charged with 3-[(5-fluoro-3-oxo-isoindolin-4-yl)amino]-4-methoxy-cyclobut-3-ene-1,2-dione (29.8 mg, 0.108 mmol), followed by (1R)-1-(5-methyl-2-furyl)propan-1-amine (25.2 mg, 0.181 mmol) in ethanol (1 mL). The reaction mixture was stirred at ambient temperature overnight. After gently blowing nitrogen over the reaction mixture to remove most of the solvent, dichloromethane and 1N-hydrochloric acid were added to the reaction mixture. The organic layer was separated and the aqueous layer was extracted twice more with dichloromethane. The combined organic layers were dried over anhydrous sodium sulfate. After removal of the solvent under reduced pressure, the crude material was purified using silica gel column chromatography using a mixture of dichloromethane and ethyl acetate as the eluent. 3-[(5-Fluoro-3-oxo-isoindolin-4-yl)amino]-4-[[(1R)-1-(5-methyl-2-furyl)propyl]amino]cyclobut-3-ene-1,2-dione (27.8 mg, 0.0725 mmol) was obtained in 67% yield. $^1$H NMR (400 MHz, DMSO-d$_6$) δ 9.49 (s, 1H), 8.72 (s, 1H), 8.26 (d, J=9.1 Hz, 1H), 7.47 (dd, J=11.2, 8.3 Hz, 1H), 7.34 (dd, J=8.3, 3.8 Hz, 1H), 6.26 (d, J=3.1 Hz, 1H), 6.05 (dd, J=3.0, 1.3 Hz, 1H), 5.08 (dd, J=8.1, 8.1 Hz, 1H), 4.33 (s, 2H), 2.26 (s, 3H), 1.91 (ddq, J=28, 8.1, 7.3 Hz, 2H), 0.91 (t, J=7.3 Hz, 3H). MS: (ES) m/z calculated for $C_{20}H_{18}FN_3O_4$ [M+H]$^+$ 384.1, found 384.3.

Example 2

Synthesis of 3-[(5-fluoro-3-oxo-isoindolin-4-yl)amino]-4-[[(1R)-2-methyl-1-(5-methyl-2-furyl)propyl]amino]cyclobut-3-ene-1,2-dione

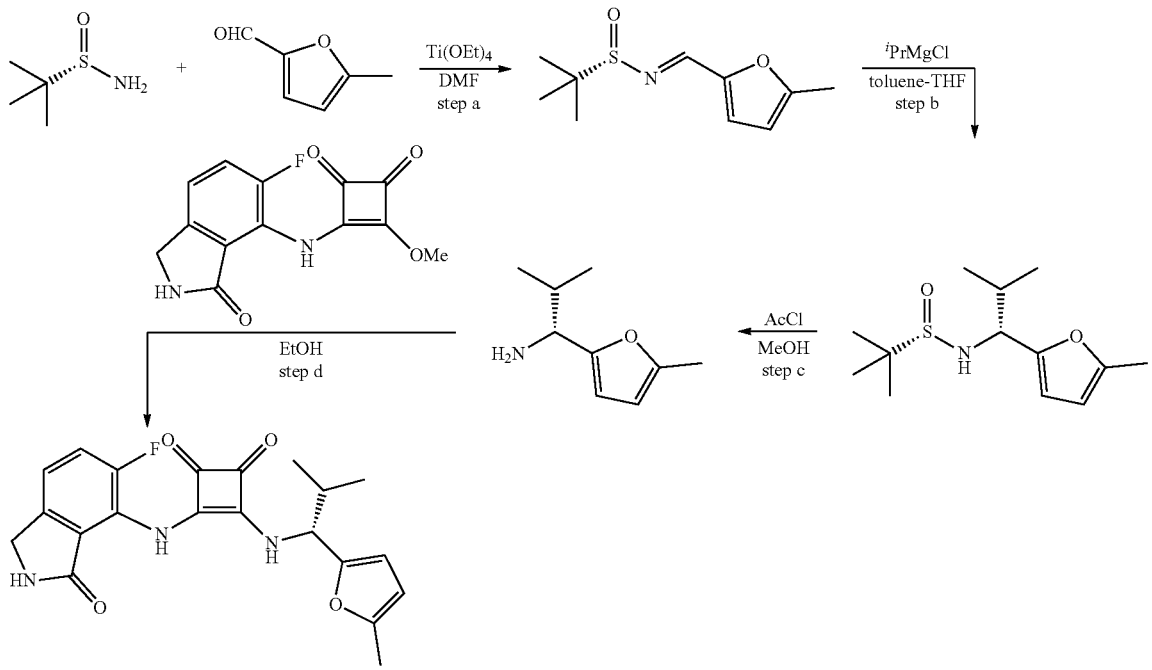

Step a: To a 500 mL round bottom flask was added (S)-2-methylpropane-2-sulfinamide (12.1 g, 100 mmol) followed by dichloromethane (100 mL) at ambient temperature. 5-Methylfuran-2-carboxaldehyde (10.9 mL, 110 mmol) in dichloromethane (13 mL) and titanium ethoxide (51 mL, 219 mmol) in dichloromethane (87 mL) were added. The reaction mixture was stirred overnight. The reaction was diluted with dichloromethane (150 mL) and quenched with sodium sulfate decahydrate (51 g). The reaction mixture was filtered through celite and rinsed with dichloromethane. Evaporation of the solvent gave the crude (S)-2-methyl-N-

[(5-methyl-2-furyl)methylene]propane-2-sulfinamide (20.89 g, 97.9 mmol) which was used directly in the next reaction.

Step b: (S)-2-methyl-N-[(5-methyl-2-furyl)methylene]propane-2-sulfinamide (1.76 g, 8.19 mmol) was dissolved in toluene (40 mL) and the reaction was cooled to −70° C. using a dry ice/isopropyl alcohol bath. Isopropyl magnesium chloride (8.2 mL, 2M solution in THF, 16.4 mmol) was added over 10 minutes. The reaction was gradually warmed to ambient temperature and stirred overnight. The reaction was quenched by the addition of saturated aqueous ammonium chloride. Organic materials were extracted using diethyl ether three times followed by a brine wash. The organic layer was dried over anhydrous sodium sulfate and after removal of the solvent under reduced pressure, the crude mixture was purified using a silica gel column using methyl tert-butyl ether/dichloromethane as eluent. (S)-2-Methyl-N-[(1R)-2-methyl-1-(5-methyl-2-furyl)propyl]propane-2-sulfinamide was obtained after removal of solvent under reduced pressure (530 mg 2.06 mmol, 90% de from NMR).

Step c: Acetyl chloride (0.366 mL, 5.15 mmol) was added dropwise to methanol (5 mL) at 0° C. to prepare a solution of anhydrous hydrogen chloride in methanol. This solution was added to (S)-2-methyl-N-[(1R)-2-methyl-1-(5-methyl-2-furyl)propyl]propane-2-sulfinamide (530 mg, 2.06 mmol) at 0° C. The reaction was slowly warmed to ambient temperature over 2 hours. Saturated sodium bicarbonate solution was added to neutralize the reaction mixture and the product was extracted with dichloromethane four times. The combined organic layer was dried over anhydrous sodium sulfate. Removal of the solvent under reduced pressure afforded the crude material (310 mg, 2.03 mmol) which was used directly in the next reaction.

Step d: To 3-[(5-fluoro-3-oxo-isoindolin-4-yl)amino]-4-methoxy-cyclobut-3-ene-1,2-dione (42.3 mg, 0.146 mmol) was added (1R)-2-methyl-1-(5-methyl-2-furyl)propan-1-amine (30.5 mg, 0.199 mmol) in ethanol (1 mL) at ambient temperature. The reaction mixture was stirred overnight at 45° C. followed by stirring at 65° C. for 5 hours. A stream of nitrogen was gently blown over the reaction mixture to remove most of the solvent. Dichloromethane and 1N-hydrochloric acid was added and the layers were separated. The aqueous layer was extracted twice more with dichloromethane. The combined organic layers were dried over anhydrous sodium sulfate. Solvent was removed under reduced pressure and the crude material was purified by silica gel column chromatography using a mixture of dichloromethane and ethyl acetate as the eluent. 3-[(5-Fluoro-3-oxo-isoindolin-4-yl)amino]-4-[[(1R)-2-methyl-1-(5-methyl-2-furyl)propyl]amino]cyclobut-3-ene-1,2-dione (52.4 mg, 0.132 mmol) was obtained in 90%/yield. $^1$H NMR (400 MHz, DMSO-$d_6$) δ 9.55 (s, 1H), 8.71 (s, 1H), 8.31 (d, J=9.7 Hz, 1H), 7.48 (dd, J=11.1, 8.3 Hz, 1H), 7.34 (dd, J=8.3, 3.8 Hz, 1H), 6.22 (d, J=3.1 Hz, 1H), 6.05 (d, J=3.0 Hz, 1H), 4.97 (t, J=8.5 Hz, 1H), 4.33 (s, 2H), 2.27 (s, 3H), 2.18 (dt, J=13.7, 6.8 Hz, 1H), 0.96 (d, J=6.7 Hz, 3H), 0.88 (d, J=6.7 Hz, 3H). MS: (ES) m/z calculated for $C_{21}H_{20}FN_3O_4$[M +H]$^+$ 398.2, found 398.4.

Example 3

Synthesis of 3-[(5,7-difluoro-3-oxo-isoindolin-4-yl)amino]-4-[[(1R)-1-(5-methyl-2-furyl)propyl]amino]cyclobut-3-ene-1,2-dione

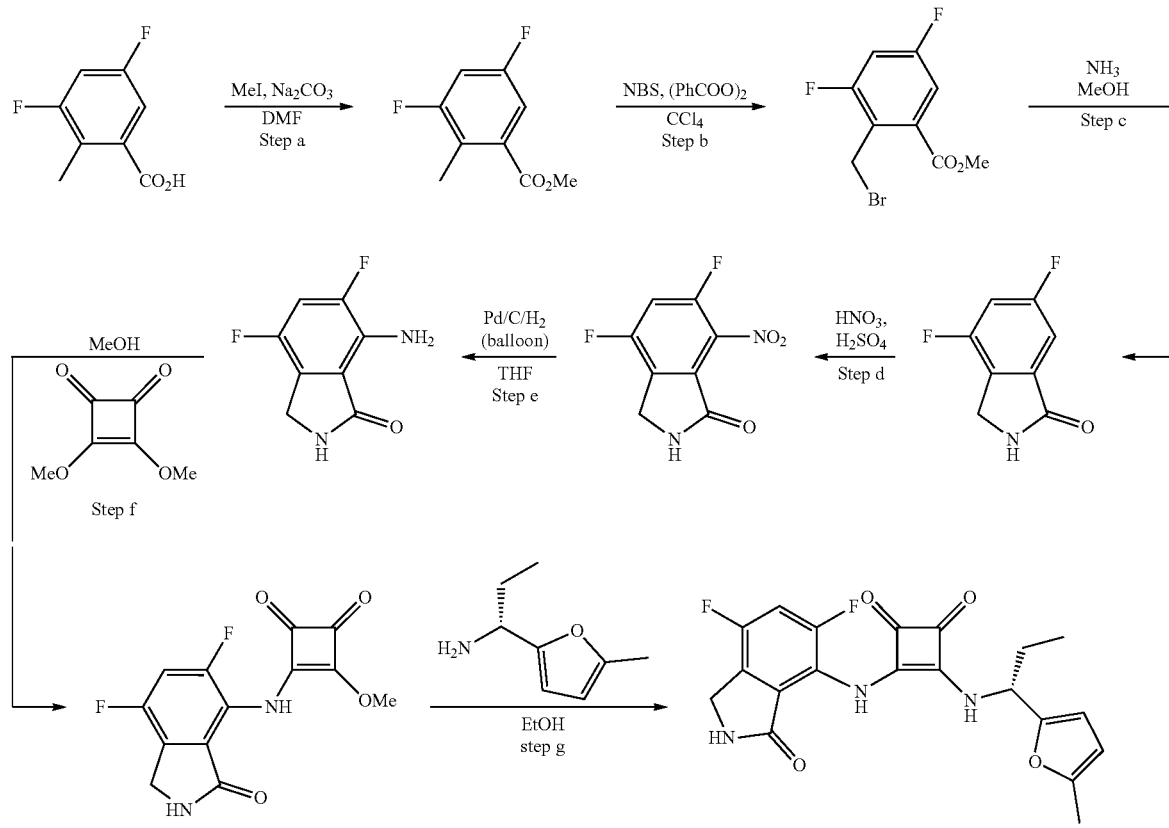

Step a: 3,5-Difluoro-2-methyl-benzoic acid (5.2 g, 30.2 mmol) was dissolved in anhydrous DMF (30 mL). Anhydrous $Na_2CO_3$ (3.5 g, 33.2 mmol, 1.1 equiv) was added and the reaction was stirred at room temperature for 30 minutes. Methyl iodide (2.1 mL, 33.2 mmol, 1.1 equiv) was added and the mixture was stirred at room temperature for 4 h, then the reaction was diluted with water (200 mL) and the product was extracted using $Et_2O$ (3×50 mL). The combined organic layers were washed with brine (4×30 mL), dried over $MgSO_4$, filtered and evaporated to give a yellow oil (5.4 g, 96%).

Step b: The product from Step a (5.4 g, 29.0 mmol) was dissolved in carbon tetrachloride (60 mL) and N-bromosuccinimide (7.7 g, 43.5 mmol, 1.5 equiv) was added followed by benzoyl peroxide (1.4 g, 5.8 mmol, 0.20 equiv). The reaction mixture was stirred at reflux overnight then cooled to room temperature and filtered. The filtrate was evaporated and the residue was purified by column chromatography (silica gel, 100% hexanes to 9:1 hexanes: ethyl acetate) to give the product as a yellow oil (7.4 g, 96%).

Step c: $NH_3$ in methanol (7 M, 45 mL, 6.4 mmol) was cooled to 0° C. and the product from Step b (6 g, 22.6 mmol) was added. The reaction mixture was stirred at 0° C. for 10 minutes and then at room temperature overnight. Excess solvent was evaporated and the residue was diluted with water (50 mL). The resulting solid was filtered and washed with water (2×20 mL), then hexanes (20 mL) to give the product (3.4 g, 89%). MS: (ES) m/z calculated for $C_8H_6F_2NO$ [M+H]$^+$ 170.04, found 170.3.

Step d: The 4,6-difluoroisoindolin-1-one from Step c (3.4 g, 20.1 mmol) was dissolved in concentrated $H_2SO_4$ (40 mL) and cooled to 0° C. 70% $HNO_3$ (1.5 mL, 24.1 mmol, 1.2 equiv) was added drop-wise and the reaction mixture was stirred at 0° C. for 10 minutes, then allowed to warm to room temperature over a period of 1 hour and stirred overnight. Ice was added and the mixture was then diluted with cold water (100 mL). The resulting yellow solid was filtered, washed with water (2×50 mL), then hexanes (50 mL) and dried under vacuum (3.4 g, 79%). MS: (ES) m/z calculated for $C_8H_5F_2N_2O_3$ [M+H]$^+$ 215.03, found 215.2.

Step e: The 4,6-difluoro-7-nitro-isoindolin-1-one from Step d (3.4 g, 15.9 mmol) was diluted with THF (50 mL) and 10% Pd/C, 50% wet, (1.7 g, 0.8 mmol, 5% mmol) was added under a nitrogen atmosphere. The reaction mixture was vigorously stirred under $H_2$ (balloon) for 1 day at room temperature, then filtered through Celite and evaporated to give the solid product (2.7 g, 92%). MS: (ES) m/z calculated for $C_8H_7F_2N_2O$ [M+H]$^+$ 185.05, found 185.3.

Step f: A mixture of 7-amino-4,6-difluoro-isoindolin-1-one from Step e (2.3 g, 12.5 mmol) and 3,4-dimethoxycyclobut-3-ene-1,2-dione (3.5 g, 25.0 mmol, 2.0 equiv) in anhydrous MeOH (15 mL) was stirred at 60° C. overnight. The reaction mixture was evaporated and the residue was diluted with MTBE:EtOAc (1:1, 200 mL) and stirred at 50° C. for 30 min, then cooled down to room temperature. The solid product was filtered, washed with MTBE, then dissolved in MeOH:DCM (1:1, 200 mL) and filtered through Celite. The filtrate was evaporated to give a gray solid (2.0 g, 54%). MS: (ES) m/z calculated for $C_{13}H_9F_2N_2O_4$ [M+H]$^+$ 295.05, found 295.3.

Step g: A 20 mL vial was charged with 3-[(5,7-difluoro-3-oxo-isoindolin-4-yl)amino]-4-methoxy-cyclobut-3-ene-1,2-dione (44.3 mg, 0.144 mmol), followed by (1R)-1-(5-methyl-2-furyl)propan-1-amine (25 mg, 0.18 mmol) in ethanol (1 mL). The reaction mixture was stirred at ambient temperature overnight, then at 80° C. for 2 hours. After gently blowing nitrogen over the reaction mixture to remove most of the solvent, dichloromethane and 1N-hydrochloric acid were added to the reaction mixture. The organic layer was separated and the aqueous layer was extracted twice more with dichloromethane. The combined organic layers were dried over anhydrous sodium sulfate. After removal of the solvent under reduced pressure, the crude material was purified by silica gel column chromatography using a mixture of dichloromethane and ethyl acetate as the eluent. The obtained product was re-suspended in ethyl acetate and filtered. The solid was filtered and dried under vacuum to give 3-[(5,7-Difluoro-3-oxo-isoindolin-4-yl)amino]-4-[[(1R)-1-(5-methyl-2-furyl)propyl]amino]cyclobut-3-ene-1,2-dione (22.6 mg, 0.0563 mmol) in 39% yield. $^1$H NMR (400 MHz, DMSO-d$_6$) δ 9.44 (s, 1H), 8.91 (s, 1H), 8.19 (d, J=9.2 Hz, 1H), 7.62 (dd, J=10.8, 8.6 Hz, 1H), 6.26 (d, J=3.0 Hz, 1H), 6.05 (d, J =3.0 Hz, 1H), 5.07 (dd, J=7.6, 7.6 Hz, 1H), 4.41 (s, 2H), 2.26 (s, 3H), 1.90 (ddq, J=27, 7.6, 7.3 Hz, 2H), 0.91 (t, J=7.3 Hz, 3H). MS: (ES) m/z calculated for $C_{20}H_{17}F_2N_3O_4$ [M+H]$^+$ 402.1, found 402.4.

Example 4

Synthesis of 3-(((S)-5-fluoro-1-methyl-3-oxoisoindolin-4-yl)amino)-4-(((R)-1-(5-methylfuran-2-yl)propyl)amino)cyclobut-3-ene-1,2-dione and 3-(((R)-5-fluoro-1-methyl-3-oxoisoindolin-4-yl)amino)-4-(((R)-1-(5-methylfuran-2-yl)propyl)amino)cyclobut-3-ene-1,2-dione

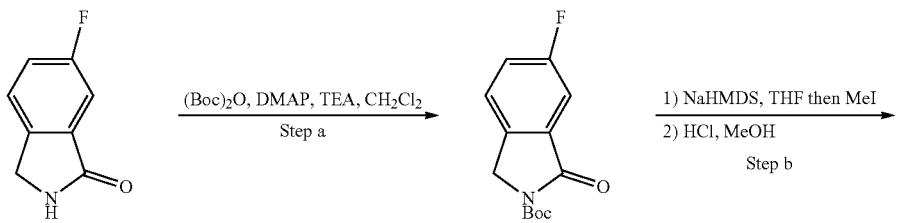

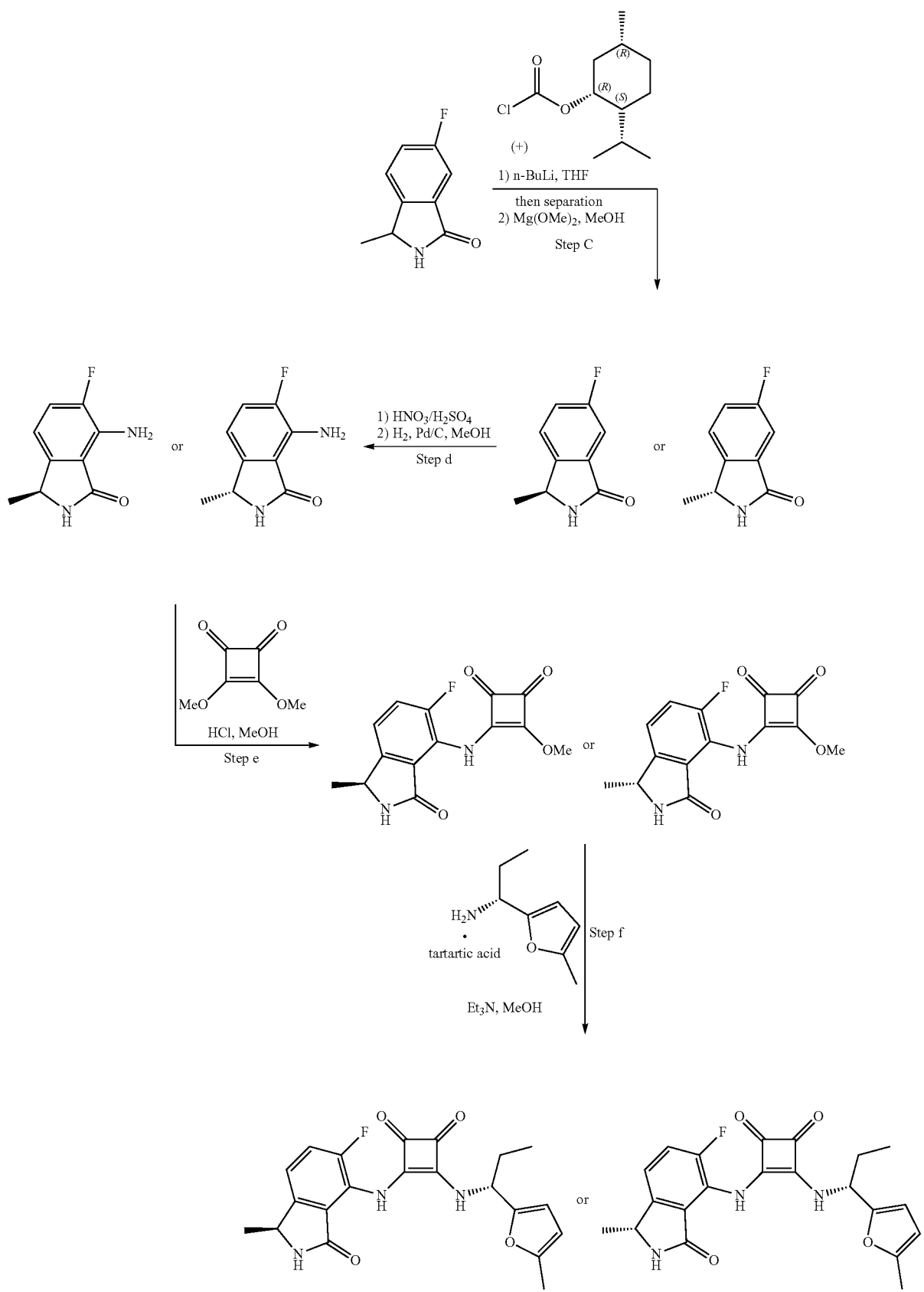

Step a: To a stirred solution of 6-fluoroisoindolin-1-one (10 g, 66.2 mmol) in anhydrous dichloromethane (100 mL) were added triethylamine (16.72, 165.5 mmol, 21.8 mL), (Boc)$_2$O (17.3 g, 79.4 mmol) and catalytic DMAP (100 mg) at room temperature. The reaction mixture was stirred at room temperature for 16 h. After completion, the reaction mixture was diluted with CH$_2$Cl$_2$, washed with H$_2$O, and then saturated aqueous NaHCO$_3$. The organic layer was dried over Na$_2$SO$_4$, filtered, and concentrated in vacuo. The crude compound was purified by silica gel chromatography (0-30% ethyl acetate in hexanes) to give the product. MS: (ES) m/z calculated for C$_{13}$H$_{14}$FNO$_3$ [M+H]$^+$ 252.3, found 252.3.

Step b: 1) To a stirred solution of tert-butyl-6-fluoro-1-oxoisoindoline-2-carboxylate (5.0 g, 19.9 mmol) in anhydrous THF (40 mL) at −78° C. under N$_2$ atmosphere was added LiHMDS (21.89 mL, 21.89 mmol) dropwise. After the solution was stirred for 30 min, a solution of methyl iodide (2.82 g, 19.92 mmol) in THF (5 mL) was added to the mixture. The reaction mixture was stirred at −78° C. for 1 h, and then the mixture was allowed to warm to room temperature and stirred for 2 h. After completion, the reaction mixture was quenched with saturated aqueous NH$_4$Cl, diluted with EtOAc (100 mL), and the organic layer was washed with H$_2$O and then brine solution. The organic layer was then dried over Na$_2$SO$_4$, filtered and concentrated in vacuo. The crude was used directly in the next step without any further purification. 2) To a stirred solution of tert-butyl-5-fluoro-1-methyl-3-oxoisoindoline-2-carboxylate (6.2 g, 66.2 mmol) in MeOH (60 mL) was added 4N HCl in dioxane (79.6 mmol, 20 mL). The mixture was stirred at room temperature for 3 h. After completion of the reaction, the solvent was removed and the reaction mixture was diluted with EtOAc (3×50 mL), the organic layer was washed with H$_2$O, and then saturated aqueous NaHCO$_3$. The organic layer was then dried over Na$_2$SO$_4$, filtered and concentrated. The crude compound was purified by silica gel, chromatography (10-80% ethyl acetate in hexanes) to give the product. MS: (ES) m/z calculated for C$_9$HaFNO [M+H]$^+$ 166.2, found 166.2.

Step c: 1) To a stirred solution of 6-fluoro-3-methylisoindolin-1-one (2.5 g, 15.1 mmol) in anhydrous THF (25 mL) at −78° C. under N$_2$ atmosphere was added n-BuLi (6.64 mL, 16.61 mmol, 2.5 M in hexane) dropwise and the reaction mixture was stirred at −78° C. for 30 min, a solution of (1R,2S,5R)-2-isopropyl-5-methylcyclohexyl chloroformate (3.96 g, 18.18 mmol) in THF (5 mL) was added to the mixture. The reaction mixture was stirred at −78° C. for 30 min, then, the reaction mixture was allowed to warm to room temperature and stirred for 3 h. After completion of the reaction, the reaction mixture was quenched with satd. NH$_4$Cl, solution, extracted with EtOAc (2×75 mL), the combined organic layer was washed with H$_2$O, and brine solution, dried over Na$_2$SO$_4$, filtered and concentrated in vacuo. The crude compound was purified by silica gel chromatography to give (1S)-(1R,2S,5R)-2-isopropyl-5-methylcyclohexyl 5-fluoro-1-methyl-3-oxoisoindoline-2-carboxylate and (1R)-(1R,2S,5R)-2-isopropyl-5-methylcyclohexyl 5-fluoro-1-methyl-3-oxoisoindoline-2-carboxylate separately. 2) To a stirred solution of one diastereomer obtained above (1.2 g, 3.45 mmol) in MeOH (10 mL) was added Mg(OMe)$_2$ (10-12% wt) in MeOH (17.2 mmol, 10 mL) at room temperature. The reaction mixture was stirred at room temperature for 2 h. After completion of the reaction, the solvent was removed and the reaction mixture was quenched with satd. NH$_4$Cl, solution, extracted with EtOAc (2×75 mL), the combined organic layer was washed with H$_2$O, and brine solution, dried over Na$_2$SO$_4$, filtered and concentrated in vacuo. The crude compound was purified by silica gel, chromatography (20-60%) ethyl acetate/ hexane to give the desired product. MS: (ES) m % z calculated for C$_9$H$_8$FNO [M+H]$^+$ 166.2, found 166.2. The other diastereomer was treated similarly to give the other desired product.

Step d: 1) One of the compounds obtained from Step c (0.45 g, 2.72 mmol) was dissolved in concentrated H$_2$SO$_4$ (5 mL) and cooled to 0° C. 700% HNO$_3$ (0.34 g, 24.1 mmol, 2.0 equiv) was added drop-wise and the reaction mixture was stirred at 0° C. for 10 minutes, then allowed to warm to room temperature stirred for overnight. Ice was added and the mixture was then diluted with cold water (10 mL), the reaction mixture was extracted with EtOAc (2×25 mL) washed with H$_2$O, and brine solution, dried over Na$_2$SO$_4$, filtered and concentrated. The crude was used directly in the next step without any further purification. MS: (ES) m/z calculated for C$_9$H$_7$F$_2$N$_2$O$_3$ [M+H]$^+$ 211.0, found 211.2. The other enantiomer was treated similarly to give the other desired product. 2) One of the compounds obtained above (0.35 g, 1.32 mmol) and 10% Pd/C (50% wet, 100 mg) in MeOH (25 mL) was stirred under a hydrogen atmosphere (par shaker) for 1 h at 40 psi. The mixture was filtered through Celite and washed with MeOH (40 mL), the filtrate was concentrated under reduced pressure to give a colorless solid, which was purified by silica gel chromatography (20-100% ethyl acetate/hexanes) to give the desired product. MS: (ES) m/z calculated for C$_9$HFN$_2$O [M+H]$^+$ 181.1, found 181.2. The other enantiomer was treated similarly to give the other desired product.

Step e: A mixture of one of the compounds obtained in Step d (170 mg, 0.939 mmol) and 3,4-dimethoxycyclobut-3-ene-1,2-dione (200 mg, 1.40 mmol) in anhydrous methanol (4 mL) was stirred at 60° C. for 3 h. The reaction mixture was evaporated and the residue was stirred in ethyl acetate (10 mL) at 50° C. for 30 min, then cooled down to room temperature. The mixture was filtered and dried to give the desired product. MS: (ES) m/z calculated for C$_{14}$H$_{11}$FN$_2$O$_4$ [M+H]$^+$ 291.1, found 291.2. The other enantiomer was treated similarly to give the other desired product.

Step f: A 20 mL vial was charged with one of the compounds obtained above (29.0 mg, 0.100 mmol), followed by (1R)-1-(5-methyl-2-furyl)propan-1-amine tartrate salt (28.9 mg, 0.100 mmol) in methanol (0.5 mL) and triethylamine (40.5 mg, 0.400 mmol). The reaction mixture was stirred at 60° C. for 3 hours. After gently blowing nitrogen over the reaction mixture to remove the solvent, the crude material was purified using reverse phase HPLC using a mixture of water and acetonitrile as the eluent to give the desired product. $^1$H NMR (400 MHz, DMSO-d) δ 9.49 (s, 1H), 8.80 (s, 1H), 8.27 (d, J=9.0 Hz, 1H), 7.48 (dd, J=11.1, 8.3 Hz, 1H), 7.37 (dd, J=8.2, 3.8 Hz, 1H), 6.27 (d, J=3.1 Hz, 1H), 6.06 (m, 1H), 5.08 (m, 1H), 4.59 (q, J=6.6 Hz, 1H), 2.27 (s, 3H), 1.92 (m, 2H), 1.36 (d, J=6.6 Hz, 3H), 0.92 (t, J=7.3 Hz, 3H). MS: (ES) m/z calculated for C$_{21}$H$_{20}$FN$_3$O$_4$ [M+Na]$^+$ 420.1, found 420.4. The other diastereomer was obtained similarly. $^1$H NMR (400 MHz, DMSO-d) δ 9.48 (s, 1H), 8.80 (s, 1H), 8.29 (d, J=8.1 Hz, 1H), 7.48 (dd, J=11.1, 8.2 Hz, 1H), 7.37 (dd, J=8.3, 3.8 Hz, 1H), 6.27 (d, J=3.1 Hz, 1H), 6.09-6.04 (m, 1H), 5.13-5.05 (m, 1H), 4.65-4.54 (m, 1H), 2.27 (s, 3H), 1.92 (m, 2H), 1.36 (d, J=6.7 Hz, 3H), 0.92 (t, J=7.3 Hz, 3H). MS: (ES) m/z calculated for C$_{21}$H$_2$OFN$_3$O$_4$ [M+Na]$^+$ 420.1, found 420.3.

Example 5

Synthesis of (R)-3-((5-fluoro-1,1-dimethyl-3-oxoisoindolin-4-yl)amino)-4-((I-(5-methylfuran-2-yl)propyl)amino)cyclobut-3-ene-1,2-dione

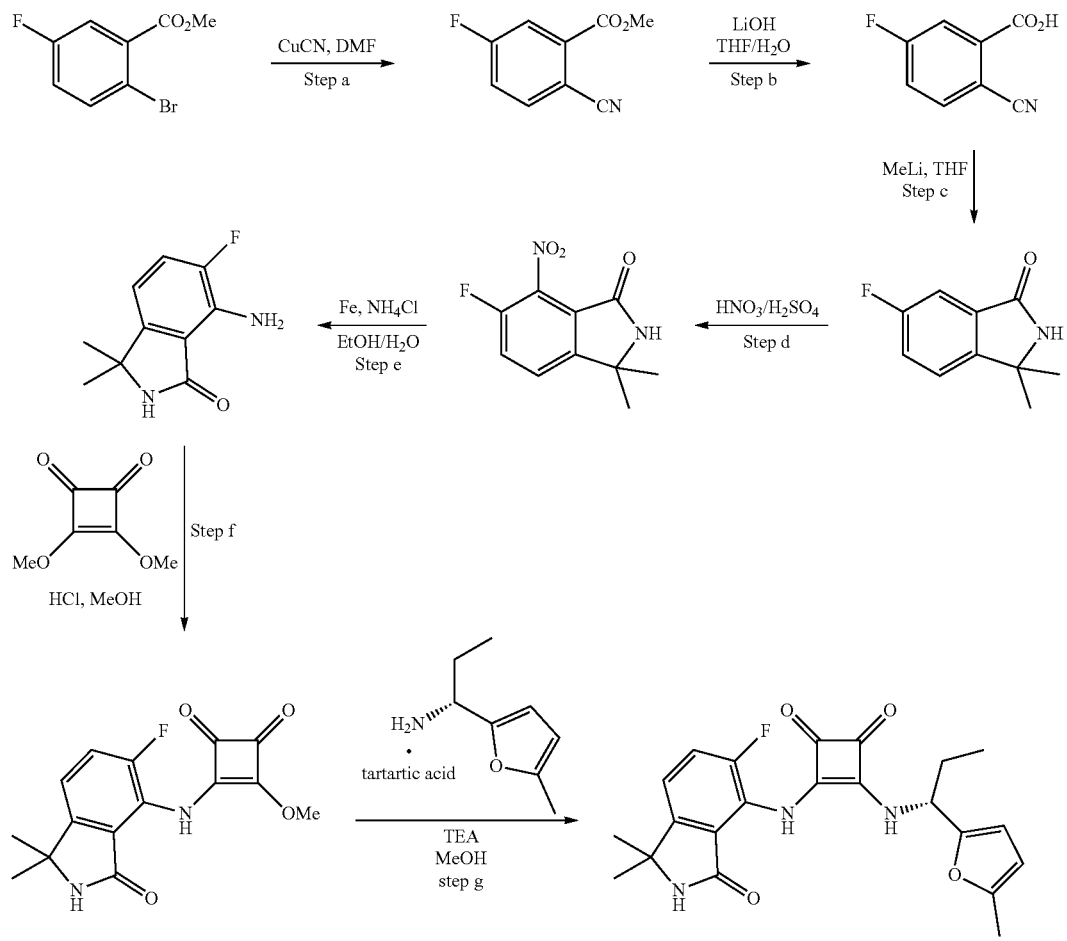

Step a: A mixture of methyl 2-bromo-5-fluorobenzoate (5.00 g, 21.5 mmol) and copper cyanide (2.12 g, 23.6 mmol) in DMF was heated at 90° C. for 1 day, then cooled down to room temperature, diluted with ethyl acetate (300 mL), and filtered. The filtrate was washed with brine (5×50 mL) and then with sat. NaHCO$_3$ (50 mL). The organic layer was dried over MgSO$_4$, filtered, concentrated in vacuo. This product was used in the next step without further purification. MS: (ES) m/z calculated for C$_9$H$_6$FNO$_2$ [M+H]$^+$ 180.0, found 180.0.

Step b: To a stirred solution of methyl 2-cyano-5-fluorobenzoate (3.85 g, 21.5 mmol) in tetrahydrofuran (30 mL) and water (3 mL) at 0° C. was added lithium hydroxide monohydrate (1.11 g, 26.5 mmol). The reaction was warmed up to rt and stirred for 1 h. Then the solvent was evaporated and the residue was diluted with water (100 mL) and 2 M HCl (20 mL). The solid was collected by filtration and dried under vacuum to give the desired product. MS: (ES) m/z calculated for C$_8$H$_4$FNO$_2$ [M+H]$^+$ 166.0, found 166.0.

Step c: To a stirred solution of 2-cyano-5-fluorobenzoic acid (1.70 g, 10.3 mmol) in anhydrous tetrahydrofuran (105 mL) at −78° C. was added 1.6 M solution of methyl lithium in ether (25.74 mL, 41.2 mmol) dropwise. The mixture was stirred at −78° C. for 1 h and was then slowly warmed up to rt, quenched with saturated ammonium chloride, and extracted with ethyl acetate. The organic layer was purified by silica gel chromatography (0-100% ethyl acetate/hexane) to give 6-fluoro-3,3-dimethylisoindolin-1-one. MS: (ES) m/z calculated for C$_{10}$H$_{10}$FNO [M+H]$^+$ 180.0, found 180.0.

Step d: A reaction vial containing 6-fluoro-3,3-dimethylisoindolin-1-one (620 mg, 3.46 mmol) in concentrated H$_2$SO$_4$ (1 mL) was cooled in an ice-bath. A mixture of concentrated H$_2$SO$_4$ (1 mL) with 70% HNO$_3$ (0.25 mL, 3.8 mmol) was added drop-wise and the reaction mixture was stirred at 0° C. for 2 h then carefully quenched with ice and diluted to 10 mL with cold water. The solid was filtered, washed with water and dried under vacuum to give the desired product 6-fluoro-3,3-dimethyl-7-nitroisoindolin-1-one. MS: (ES) m/z calculated for C$_{10}$H$_9$FN$_2$O$_3$ [M+H]$^+$ 225.0, found 225.0.

Step e: To a solution of 6-fluoro-3,3-dimethyl-7-nitroisoindolin-1-one (0.56 g, 2.50 mmol) in ethanol (10 mL) and water (1 mL) at room temperature was added iron powder (0.58 g, 10.38 mmol) and ammonium chloride (1.90 g, 34.6 mmol). The reaction mixture was warmed up to 90° C. and stirred for 1 hour. Then it was cooled to room temperature, filtered through Celite and rinsed with methanol (20 ml). The filtrate was concentrated to dryness and the residue was diluted with ethyl acetate, washed with water and brine. The combined organic layers were dried (Na$_2$SO$_4$), filtered, concentrated in vacuo, and purified by silica gel chromatography (0-100% ethyl acetate in hexanes) to provide the product 7-amino-6-fluoro-3,3-dimethylisoindolin-1-one. MS: (ES) m/z calculated for C$_{10}$H$_{11}$FN$_2$O [M+H]$^+$ 195.1, found 195.1.

Step f: A mixture of 7-amino-6-fluoro-3,3-dimethylisoindolin-1-one (25 mg, 0.129 mmol), 3,4-dimethoxycyclobut-3-ene-1,2-dione (22.0 mg, 0.155 mmol, 1.2 equiv), and HCl solution in dioxane (4 M, 32.3 µL) in anhydrous MeOH (0.65 mL) was stirred at 60° C. for 18 hours. The solvents were removed to give the product which was directly used in the next step.

Step g: A 20 mL vial was charged with 3-((5-fluoro-1,1-dimethyl-3-oxoisoindolin-4-yl)amino)-4-methoxycyclobut-3-ene-1,2-dione obtained above, followed by (1R)-1-(5-methyl-2-furyl)propan-1-amine tartrate salt (115.7 mg, 0.400 mmol) in methanol (0.5 mL) and triethylamine (101 mg, 1.00 mmol). The reaction mixture was stirred at 60° C. for 18 hours. After gently blowing nitrogen over the reaction mixture to remove the solvent, the crude material was purified using reverse phase HPLC using a mixture of water and acetonitrile as the eluent. (R)-3-((5-fluoro-1,1-dimethyl-3-oxoisoindolin-4-yl)amino)-4-((1-(5-methyl furan-2-yl)propyl)amino)cyclobut-3-ene-1,2-dione was obtained. $^1$H NMR (400 MHz, DMSO-d$_6$) δ 9.48 (s, 1H), 8.81 (s, 1H), 8.28 (d, J=9.1 Hz, 1H), 7.47 (dd, J=11.0, 8.2 Hz, 1H), 7.41 (dd, J=8.3, 3.9 Hz, 1H), 6.27 (d, J=3.1 Hz, 1H), 6.09-6.03 (m, 1H), 5.08 (m, 1H), 2.27 (s, 3H), 1.92 (m, 2H), 1.43 (s, 6H), 0.92 (t, J=7.3 Hz, 3H). MS: (ES) m/z calculated for C$_{22}$H$_{22}$FN$_3$O$_4$ [M+Na]$^+$ 434.1, found 434.4.

Example 6

Synthesis of (R)-3-((5-fluoro-1,1,7-trimethyl-3-oxoisoindolin-4-yl)amino)-4-((1-(5-methylfuran-2-yl)propyl)amino)cyclobut-3-ene-1,2-dione Step a: To a solution of 7-amino-6-fluoro-3,3-dimethylisoindolin-1-one (150 mg, 0.77 mmol) in AcOH (2 mL) in a water bath was added NIS (244 mg, 1.08 mmol) in potions at room temperature. The resulting mixture was stirred in a water bath for 30 minutes, quenched with water (1 mL) and extracted with ethyl acetate (10 mL). The organic layer was washed with brine (10 mL) and then dried over MgSO$_4$. The solvent was evaporated under reduced pressure to give a brown solid, which was purified by silica gel chromatography (0-60% ethyl acetate in hexanes) to give 7-amino-6-fluoro-4-iodo-3,3-dimethylisoindolin-1-one. MS: (ES) m/z calculated for C$_{10}$H$_{10}$FIN$_2$O [M+H]$^+$ 321.0, found 321.0.

Step b: To a solution of 7-amino-6-fluoro-4-iodo-3,3-dimethylisoindolin-1-one (370 mg, 1.16 mmol) in dioxane (12 mL) was added CsF (705 mg, 4.64 mmol), 2,4,6-trimethyl-1,3,5,2,4,6-trioxatriborinane (435 mg, 3.47 mmol), and [1,1'-bis(diphenylphosphino)ferrocene]dichloropalladium(II) (95 mg, 0.116 mmol). The resulting mixture was stirred at 80° C. overnight. The reaction was partitioned between water (20 mL) and ethyl acetate (30 mL). The organic layer was washed with brine (20 mL) and then dried over MgSO$_4$, filtered, and concentrated to give the crude, which was purified by silica gel chromatography (0-80% ethyl acetate in hexanes) to give 7-amino-6-fluoro-3,3,4-trimethylisoindolin-1-one. MS: (ES) m/z calculated for C$_{11}$H$_3$FN$_2$O [M+H]$^+$ 209.1, found 209.1.

Step c: A mixture of 7-amino-6-fluoro-3,3,4-trimethylisoindolin-1-one (40 mg, 0.192 mmol), 3,4-dimethoxycyclobut-3-ene-1,2-dione (32.8 mg, 0.231 mmol, 1.2 equiv), and HCl solution in dioxane (4 M, 48 µL) in anhydrous MeOH (1.0 mL) was stirred at 60° C. for 18 hours. The solvents were removed to give the product which was directly used in the next step.

Step d: A 20 mL vial was charged with 3-((5-fluoro-1,1,7-trimethyl-3-oxoisoindolin-4-yl)amino)-4-methoxycyclobut-3-ene-1,2-dione obtained above, followed by (1R)-(5-methyl-2-furyl)propan-1-amine tartrate salt (222.7 mg, 0.77 mmol) in methanol (1.0 mL) and triethylamine (233 mg, 2.3 mmol). The reaction mixture was stirred at 60° C. for 18 hours. After gently blowing nitrogen over the reaction

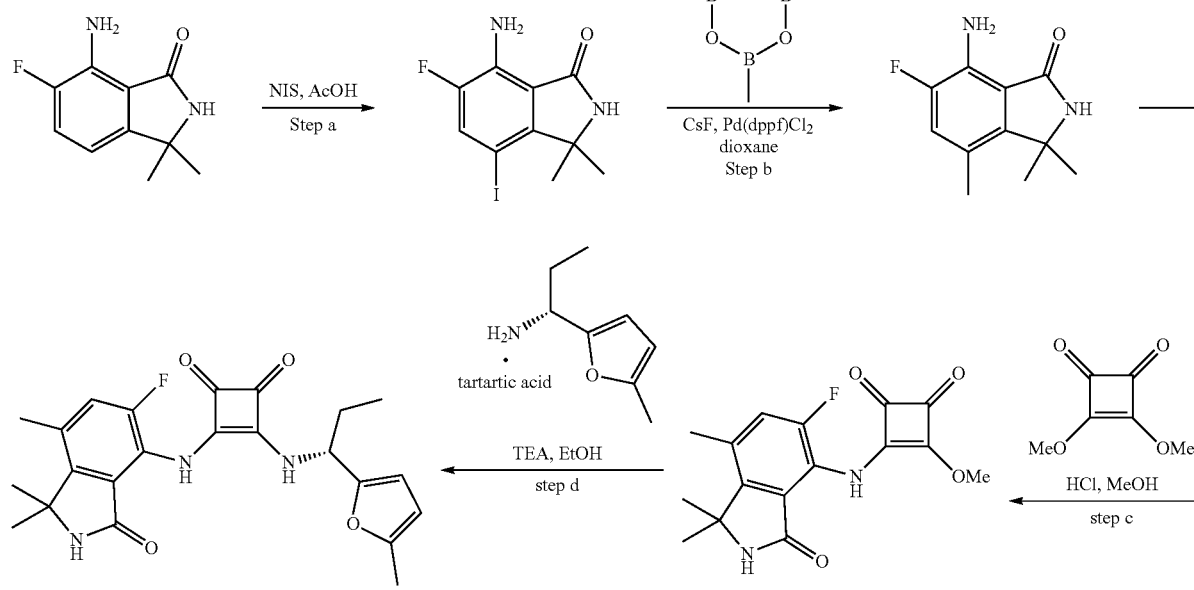

mixture to remove the solvent, the crude material was purified using reverse phase HPLC using a mixture of water and acetonitrile as the eluent. (R)-3-((5-fluoro-1,1,7-trimethyl-3-oxoisoindolin-4-yl)amino)-4-((1-(5-methylfuran-2-yl)propyl)amino)cyclobut-3-ene-1,2-dione was obtained. $^1$H NMR (400 MHz, DMSO-$d_6$) δ 9.41 (s, 1H), 8.83 (s, 1H), 8.31 (d, J=9.1 Hz, 1H), 7.29 (d, J=12.0 Hz, 1H), 6.26 (d, J=3.1 Hz, 1H), 6.12-6.02 (m, 1H), 5.08 (m, 1H), 2.41 (s, 3H), 2.27 (s, 3H), 1.90 (m, 2H), 1.49 (s, 6H), 0.92 (t, J=7.3 Hz, 3H). MS: (ES) m/z calculated for $C_{23}H_{24}FN_3O_4$ [M+Na]$^+$ 448.2, found 448.4.

Example 7

Synthesis of (R)-2-(4-chloro-7-((2-((1-(5-methylfuran-2-yl)propyl)amino)-3,4-dioxocyclobut-1-en-1-yl)amino)-1-oxoisoindolin-2-yl)-4-methoxybenzoic acid Step a: A 1 L round bottom flask containing 4-chloroisoindolin-1-one (25.0 g, 0.149 mole) in concentrated $H_2SO_4$ (50 mL) was cooled in an ice-bath. A mixture of concentrated $H_2SO_4$ (50 mL) with 70% $HNO_3$ (10 mL, 0.16 mole, 1.05 equiv.) was added drop-wise and the reaction mixture was stirred at 0° C. for 2 h then carefully quenched with ice and diluted to 1 L with cold water. The solid was filtered, washed with water and dried under high vacuum to afford 4-chloro-7-nitro-isoindolin-1-one. MS: (ES) m/z calculated for $C_8H_5ClN_2O_3$ [M−H]$^+$ 212.0, found 212.0.

Step b: To a stirred mixture of 4-chloro-7-nitro-isoindolin-1-one (23 g, 108 mmol) in ethanol at room temperature was added iron powder (18.2 g, 324 mmol), followed by 4 M HCl in dioxane (162 mL, 648 mmol). The reaction mixture was stirred at room temperature for 1 h then concentrated in vacuo. The residue was diluted with ethyl acetate and neutralized with saturated sodium bicarbonate solution and extracted with ethyl acetate (2×500 mL). The

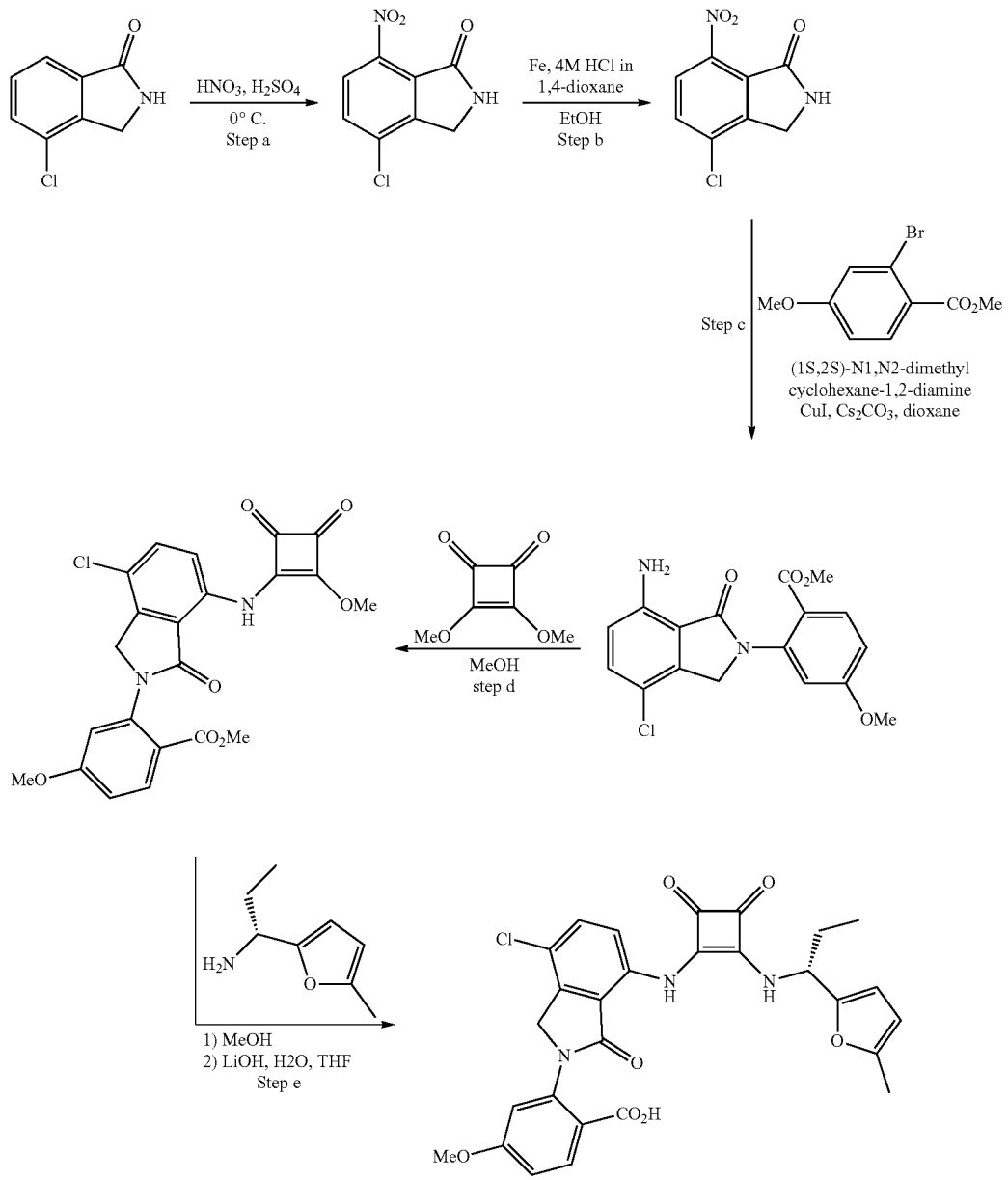

combined organic layers were dried (Na$_2$SO$_4$), filtered, and concentrated in vacuo to afford 7-amino-4-chloro-isoindolin-1-one. MS: (ES) m/z calculated for C$_8$H$_7$ClN$_2$O [M+H]$^+$ 183.2, found 183.2.

Step c: To a reaction vial containing 7-amino-4-chloro-isoindolin-1-one (250 mg, 1.37 mmol) in dioxane (10 mL) was added methyl 2-bromo-5-methoxy-benzoate (502 mg, 2.05 mmol), cesium carbonate (893 mg, 2.74 mmol), copper iodide (104 mg, 0.55 mmol) and (1S,2S)—N1,N2-dimethylcyclohexane-1,2-diamine (156 mg, 1.1 mmol). The mixture was purged with nitrogen, then warmed to 110° C. The reaction was stirred at 110° C. for 1 h and the reaction was monitored by LC-MS. Following completion, the reaction was allowed to cool and was then filtered through Celite and rinsed with ethyl acetate. The crude was purified by silica gel chromatography (0-50% ethyl acetate/hexane) to give methyl 2-(7-amino-4-chloro-1-oxo -isoindolin-2-yl)-5-methoxy-benzoate. MS: (ES) m/z calculated for C$_{17}$H$_{15}$ClN$_2$O$_4$ [M+H]$^+$ 347.1, found 347.1.

temperature for 1 h and 60° C. for 2 h. Aqueous HCl (1N) and dichloromethane were added and the combined organic layer was concentrated. THF was added and the mixture was filtered to get rid of the solid. The residue was purified by reverse phase HPLC using a mixture of water and acetonitrile as the eluent. (R)-2-(4-chloro-7-((2-((1-(5-methylfuran-2-yl)propyl)amino)-3,4-dioxocyclobut-1-en-1-yl)amino)-1-oxoisoindolin-2-yl)-4-methoxybenzoic acid was obtained. $^1$H NMR (400 MHz, Methanol-d$_4$) δ 8.12-8.03 (m, 2H), 7.59 (d, J=8.8 Hz, 1H), 7.15-7.02 (m, 2H), 6.20 (s, 1H), 5.94 (s, 1H), 5.20-4.80 (m, 3H), 3.90 (s, 3H), 2.24 (s, 3H), 2.03-1.85 (m, 2H), 0.99 (t, J=7.4 Hz, 3H). MS: (ES) m/z calculated for C$_{28}$H$_{24}$ClN$_3$O$_7$ [M+H]$^+$ 550.1, found 550.3.

Example 8

Synthesis of (R)-3-((5-fluoro-3-oxoisoindolin-4-yl)amino)-4-((l-(5-methylfuran -2-yl)propyl-1-d)amino)cyclobut-3-ene-1,2-dione

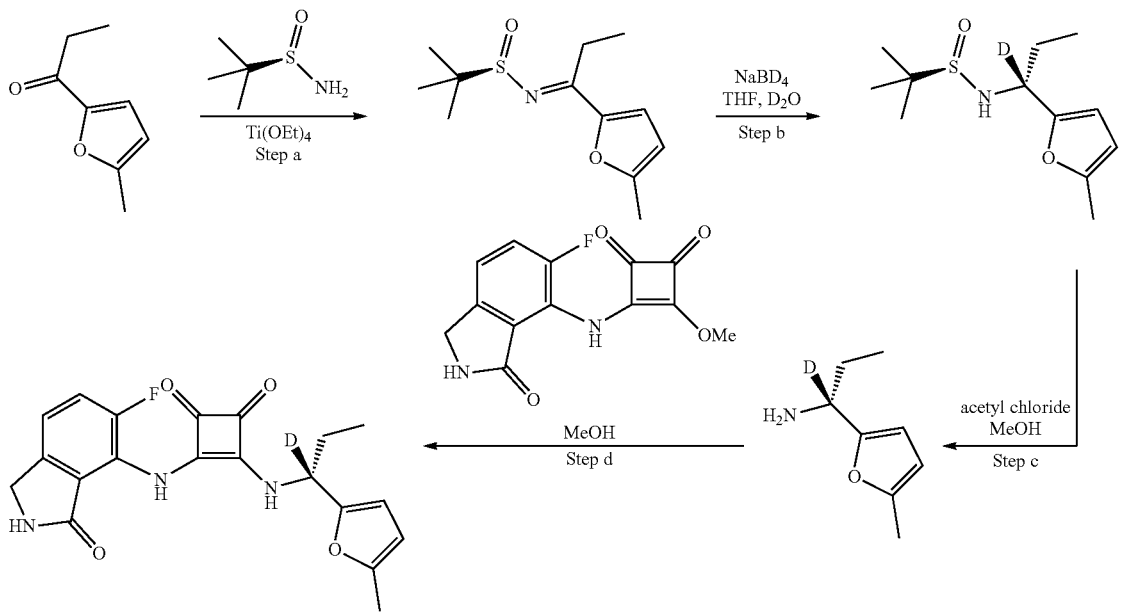

Step d: A mixture of methyl 2-(7-amino-4-chloro-1-oxo-isoindolin-2-yl)-5-methoxy-benzoate (160 mg, 0.46 mmol) and 3,4-dimethoxycyclobutane-1,2-dione (131 mg, 0.92 mmol) in anhydrous methanol (5 mL) was stirred at 60° C. overnight. The reaction mixture was evaporated and the residue was stirred in ethyl acetate (5 mL) at 50° C. for 30 min, then allowed to cool to room temperature. The mixture was filtered and dried to give the product methyl 2-[4-chloro-7-[(2-methoxy-3,4-dioxo-cyclobutyl)amino]$^+$ 1-oxo-isoindolin-2-yl]-5-methoxy-benzoate. MS: (ES) m/z calculated for C$_{22}$H$_{17}$ClN$_2$O$_7$ [M+H]$^+$ 457.1, found 457.1.

Step e: To methyl 2-(4-chloro-7-((2-methoxy-3,4-dioxo-cyclobut-1-en-1-yl)amino)-1-oxoisoindolin-2-yl)-4-methoxybenzoate (60 mg, 0.12 mmol) was added (R)-1-(5-methylfuran-2-yl)propan-1-amine (22 mg, 0.15 mmol) in methanol (5 mL) at ambient temperature. The reaction mixture was stirred overnight at 60° C. and then concentrated. The residue was diluted with dichloromethane and washed with water. The organic layer was concentrated. To the residue was added THF (5 mL), water (1 mL), and LiOH (large excess). The reaction mixture was stirred at room Step a: To a 40 mL vial was added (R)-2-methylpropane-2-sulfinamide (1.83 g, 15.1 mmol), 1-(5-methylfuran-2-yl)propan-1-one (2.0 mL, 15.1 mmol), and titanium ethoxide (7.8 mL). The reaction mixture was stirred at 60° C. overnight. The reaction was diluted with dichloromethane (100 mL) and quenched with sodium sulfate decahydrate (10.2 g). The reaction mixture was filtered through celite and rinsed with dichloromethane. Evaporation of the solvent gave the crude product which was purified by silica gel chromatography using a mixture of ethyl acetate and hexane as the eluent.

Step b: To a mixture of the product from the previous step (1122 mg, 4.65 mmol), THF (17.5 mL), and D$_2$O (0.36 mL) at −55° C. was added sodium borodeuteride (575 mg, 13.7 mmol). The reaction mixture was stirred at the same temperature for 3 h. After gently blowing nitrogen over the reaction mixture to remove the solvent, dichloromethane was added. The mixture was filtered and the filtrate was concentrated. The residue was purified by silica gel chromatography using a mixture of dichloromethane and methyl tert-butyl ether as the eluent.

Step c: The product from the previous step (422 mg, 1.73 mmol) was dissolved in MeOH (5 mL) at 0° C., and acetyl chloride (400 μL) was added. The reaction was stirred for 1 h. After gently blowing nitrogen over the reaction mixture to remove the solvent, a mixture of methyl tert-butyl ether and water was added. The aqueous layer was collected and basified with sodium carbonate solution (2 M). The mixture was extracted with $CHCl_3$ (3×). The combined organic layers were dried over $Na_2SO_4$, filtered, and concentrated to give the product.

Step d: To 3-((5-fluoro-3-oxoisoindolin-4-yl)amino)-4-methoxycyclobut-3-ene-1,2-dione (41.4 mg, 0.150 mmol) was added (R)-1-(5-methylfuran-2-yl)propan-1-d-1-amine (31.9 mg, 0.228 mmol) in methanol (1 mL) at ambient temperature. The reaction mixture was stirred overnight at 45° C. After gently blowing nitrogen over the reaction mixture to remove the solvent, a mixture of aqueous HCl (1N) and dichloromethane was added. The mixture was filtered and the residue was purified by prep TLC using ethyl acetate as the eluent. (R)-3-((5-fluoro-3-oxoisoindolin-4-yl)amino)-4-((1-(5-methylfuran-2-yl)propyl-1-d)amino)cyclobut-3-ene-1,2-dione was obtained. $^1$H NMR (400 MHz, DMSO-$d_6$) δ 9.47 (s, 1H), 8.70 (s, 1H), 8.25 (s, 1H), 7.46 (dd, J=11.2, 8.2 Hz, 1H), 7.33 (dd, J=8.2, 3.7 Hz, 1H), 6.25 (d, J=3.1 Hz, 1H), 6.06-6.03 (m, 1H), 4.32 (s, 2H), 2.26 (s, 3H), 2.00-1.80 (m, 2H), 0.90 (t, J=7.3 Hz, 3H). MS: (ES) m/z calculated for $C_{20}DH_{17}FN_3O_4$ [M+H]$^+$ 385.1, found 385.4.

Example 9 ynthesis of (R)-3-((5-fluoro-3-oxoisoindolin-4-yl)amino)-4-((l-(5-methyloxazol-2-yl)propyl)amino)cyclobut-3-ene-1,2-dione was further stirred at room temperature for 2 h. The reaction mixture was diluted with water and diethyl ether, and extracted with diethyl ether (6×). The combined organic layers were dried over $Na_2SO_4$, filtered, and concentrated. The residue was purified by silica gel chromatography using a mixture of ethyl acetate and dichloromethane as the eluent.

Step b: To a 40 mL vial were added auric chloride (128 mg, 0.424 mmol), acetonitrile (10 mL), and the product from the previous step (501 mg, 2.09 mmol). The reaction mixture was stirred at 50° C. overnight. After gently blowing nitrogen over the reaction mixture to remove the solvent, a mixture of saturated ammonium chloride solution and methyl tert-butyl ether was added. The mixture was extracted with methyl tert-butyl ether (3×). The combined organic layers were dried over $Na_2SO_4$, filtered, and concentrated. The residue was purified by silica gel chromatography using a mixture of ethyl acetate and hexane as the eluent.

Step c: To a stirred solution of the product from the previous step (301 mg, 1.25 mmol) in dichloromethane (1 mL) was added 4N HCl in dioxane (1 mL). The mixture was stirred at room temperature overnight. After gently blowing nitrogen over the reaction mixture to remove the solvent, a mixture of water and hexane was added. The aqueous layer was collected and basified with saturated sodium bicarbonate solution. The mixture was extracted with dichloromethane (3×) and chloroform/isopropanol (2/1, v/v) (2×). The combined organic layers were dried over $Na_2SO_4$, filtered, and concentrated to give the product.

Step d: To 3-((5-fluoro-3-oxoisoindolin-4-yl)amino)-4-methoxycyclobut-3-ene-1,2-dione (42.4 mg, 0.154 mmol) was added (R)-1-(5-methyloxazol-2-yl)propan-1-amine (25.9 mg, 0.185 mmol) in methanol (0.5 mL) at ambient temperature. The reaction mixture was stirred overnight at

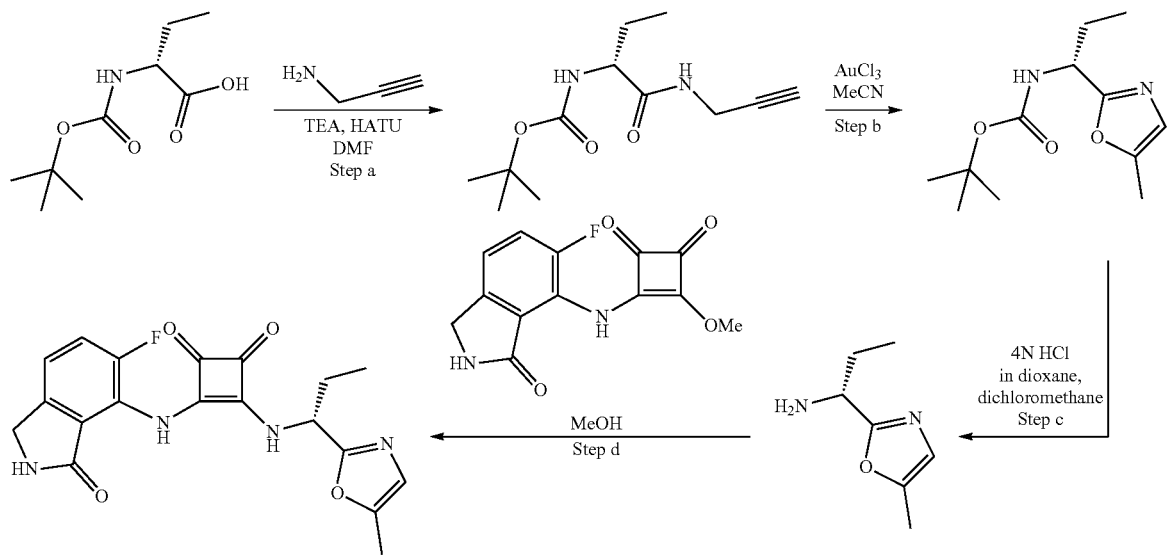

Step a: To a 40 mL vial was added (R)-2-((tert-butoxycarbonyl)amino)butanoic acid (1.00 g, 4.92 mmol), 1-[bis(dimethylamino)methylene]-1H-1,2,3-triazolo[4,5-b]pyridinium 3-oxid hexafluorophosphate (HATU, 1.96 g, 5.16 mmol), DMF (6 mL), and triethylamine (1.51 mL). The reaction mixture was stirred for 2 min and prop-2-yn-1-amine (378 μL, 5.90 mmol) was added. The reaction mixture 50° C. After gently blowing nitrogen over the reaction mixture to remove the solvent, a mixture of aqueous HCl (1N) and dichloromethane was added. The mixture was filtered and the residue was purified by prep TLC using a mixture of dichloromethane and acetonitrile (1/1, v/v) as the eluent. (R)-3-((5-fluoro-3-oxoisoindolin-4-yl)amino)-4-((1-(5-methyloxazol-2-yl)propyl)amino)cyclobut-3-ene-1,2-dione was obtained. $^1$H NMR (400 MHz, DMSO-$d_6$) δ 9.63 (s, 1H), 8.73 (s, 1H), 8.48 (d, J=7.5 Hz, 1H), 7.49 (dd, J=11.2, 8.2 Hz, 1H), 7.36 (dd, J=8.3, 3.8 Hz, 1H), 6.87 (d, J=1.4 Hz, 1H), 5.33-5.20 (m, 1H), 4.34 (s, 2H), 2.32 (d, J=1.2 Hz, 3H), 2.09-1.87 (m, 2H), 0.93 (t, J=7.4 Hz, 3H). MS: (ES) m/z calculated for $C_{19}H_{17}FN_4O_4$ [M+H]$^+$ 385.1, found 385.4.

Example 10

Synthesis of (R)-2-(4-chloro-7-((2-((I-(5-methyl-furan-2-yl)propyl)amino)-3,4-dioxocyclobut-1-en-1-yl)amino)-1-oxoisoindolin-2-yl)acetamide mmol, 1.1 equiv.) was added and stirring was continued at room temperature for 3 h. The reaction mixture was diluted with water (1.2 L) and the product was extracted using $Et_2O$ (3×250 mL). The combined organic layers were washed with brine (4×100 mL), dried over $MgSO_4$, filtered and evaporated to give product.

Step c: The mixture of isomeric esters from the previous step (49.7 g, 216.5 mmol) was dissolved in $CCl_4$ (400 mL) and N-bromosuccinimide (57.8 g, 324.7 mmol, 1.5 equiv.) was added followed by benzoyl peroxide (10.4 g, 43.2 mmol, 0.20 equiv). The reaction mixture was stirred under reflux overnight then cooled to room temperature and fil-

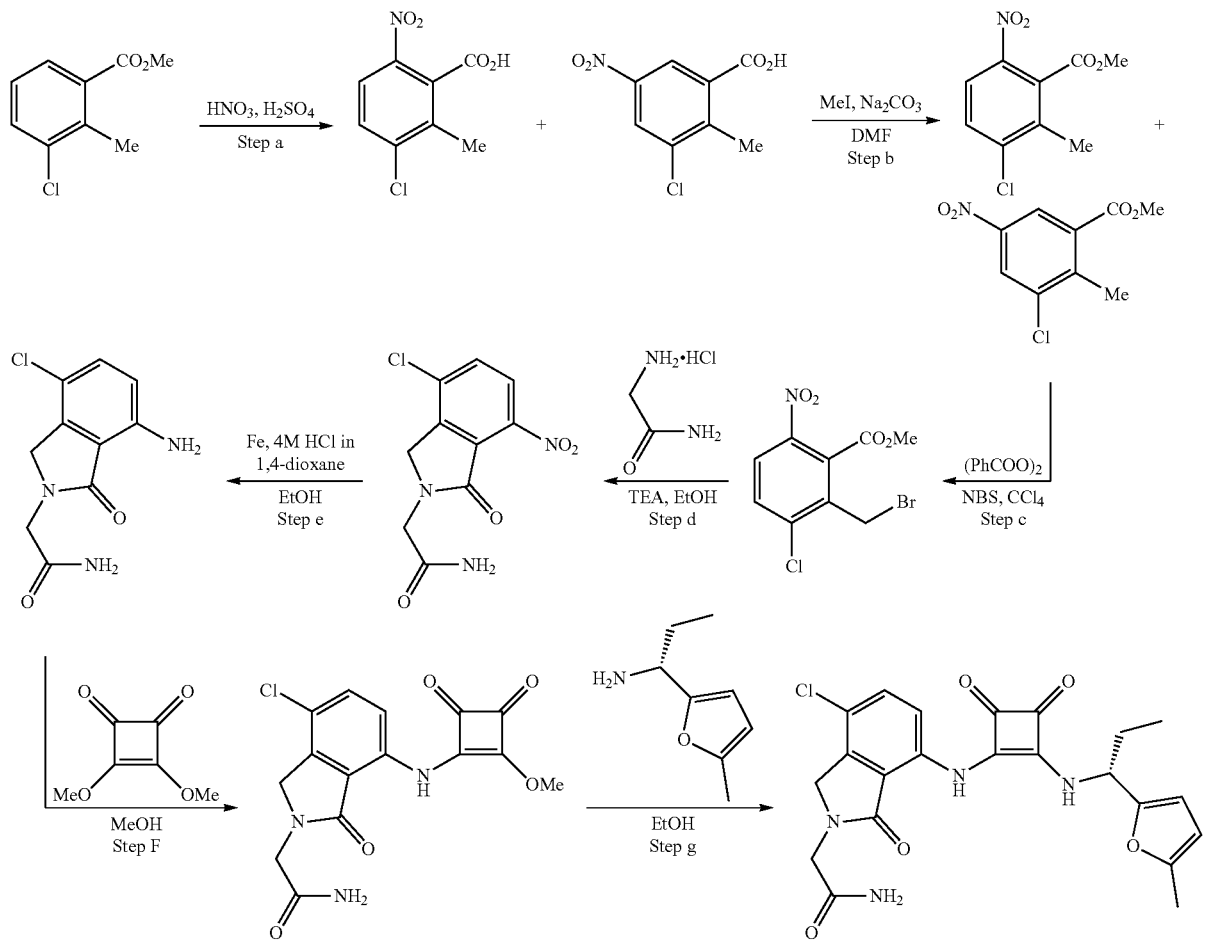

Step a: A 4 L Erlenmeyer flask containing 3-chloro-2-methyl-benzoic acid (100.0 g, 0.586 mole) in concentrated $H_2SO_4$ (500 mL) was cooled in an ice-bath. 70% $HNO_3$ (45.2 mL, 0.703 mole, 1.2 equiv.) was added drop-wise and reaction mixture was stirred at 0° C. for 2 h, then carefully quenched with ice and diluted to 4 L with cold water. A white solid was filtered, washed with water and dried under high vacuum to afford a mixture of 3-chloro-2-methyl-6-nitro-benzoic acid and 3-chloro-2-methyl-5-nitro-benzoic acid in 3:1 ratio. MS: (ES) m/z calculated for $C_8H_5ClNO_4$ [M−H]$^+$ 214.0, found 214.0.

Step b: The mixture of isomeric acids from the previous step (50 g, 232.0 mmol) was dissolved in anhydrous DMF (200 mL), anhydrous $Na_2CO_3$ (27.0 g, 255.2 mmol, 1.1 equiv.) was added, and the reaction was stirred at room temperature for 30 minutes. Methyl iodide (15.9 mL, 255.2 tered. The filtrate was evaporated and the residue was purified by silica gel chromatography (100:0 to 9:1 Hex: EtOAc) to give product as a single isomer. $^1$H NMR (400 MHz, $CDCl_3$) 8.07 (d, J=9.2 Hz, 1H), 7.65 (d, J=9.2 Hz, 1H), 4.63 (s, 2H), 4.01 (s, 3H).

Step d: A mixture of the product from the previous step (316 mg, 1.02 mmol), 2-aminoacetamide hydrochloride (171 mg, 1.55 mmol) and triethylamine (427 μL, 3.06 mmol) in ethanol (2 mL) was stirred at room temperature overnight. After gently blowing nitrogen over the reaction mixture to remove the solvent, a mixture of aqueous HCl (1N) and water was added. The mixture was filtered and the residue was rinsed with aqueous HCl (1N) and water to afford the desired product.

Step e: To a stirred mixture of the product from the previous step (249 mg, 0.925 mmol) in ethanol (1 mL) at room temperature was added iron powder (158 mg, 2.68 mmol), followed by 4 M HCl in dioxane (0.46 mL, 1.84 mmol). The reaction mixture was stirred at room temperature overnight. Saturated sodium bicarbonate aqueous solution was added and the mixture was diluted with methanol. The mixture was filtered through celite and rinsed with methanol. The filtrate was concentrated to remove methanol and subsequently extracted with dichloromethane. The combined organic layers were concentrated to afford the desired product.

Step f: A mixture of the product from the previous step (131 mg, 0.55 mmol) and 3,4-dimethoxycyclobutane-1,2-dione (118 mg, 0.83 mmol) in anhydrous methanol (2 mL) was stirred at 60° C. overnight. After gently blowing nitrogen over the reaction mixture to remove the solvent, ethyl acetate was added. The mixture was filtered, rinsed with ethyl acetate, and dried to give the product.

Step g: To 2-(4-chloro-7-((2-methoxy-3,4-dioxocyclobut-1-en-1-yl)amino)-1-oxoisoindolin-2-yl)acetamide (39.9 mg, 0.114 mmol) was added (R)-1-(5-methylfuran-2-yl)propan-1-amine (23.0 mg, 0.165 mmol) in ethanol (1 mL) at ambient temperature. The reaction mixture was stirred overnight at 65° C. After gently blowing nitrogen over the reaction mixture to remove the solvent, a mixture of aqueous HCl (1N) and dichloromethane was added. The mixture was filtered and the residue was rinsed with water, dichloromethane, and methyl tert-butyl ether. (R)-2-(4-chloro-7-((2-((1-(5-methylfuran-2-yl)propyl)amino)-3,4-dioxocyclobut-1-en-1-yl)amino)-1-oxoisoindolin-2-yl)acetamide was obtained. $^1$H NMR (400 MHz, DMSO-d$_6$) δ 9.74 (s, 1H), 9.12 (d, J=8.9 Hz, 1H), 7.67-7.52 (m, 3H), 7.27-7.18 (m, 1H), 6.25 (d, J=3.1 Hz, 1H), 6.06-6.02 (m, 1H), 5.18-5.08 (m, 1H), 4.48 (s, 2H), 4.11 (s, 2H), 2.25 (s, 3H), 2.01-1.80 (m, 2H), 0.90 (t, J=7.3 Hz, 3H). MS: (ES) m/z calculated for $C_{22}H_{21}ClN_4O_5$ [M+Na]$^+$ 479.1, found 479.0.

The following compounds were made using similar synthetic methods as described herein with the appropriate reagents and were characterized by MS (Mass spectrometry) and NMR as illustrated in Table 1.

TABLE 1

| Characterization of compounds | | |
|---|---|---|
| Structure | NMR | MS |
| (structure with Cl, methoxyphenyl, CONH$_2$, methylfuran) | 1H NMR (400 MHz, Methanol-d4) δ 8.06 (d, J = 8.6 Hz, 1H), 7.67 (d, J = 8.7 Hz, 1H), 7.56 (d, J = 8.7 Hz, 1H), 7.11 (d, J = 2.5 Hz, 1H), 7.02 (dd, J = 8.6, 2.5 Hz, 1H), 6.19 (s, 1H), 5.95-5.91 (m, 1H), 5.28-5.20 (m, 1H), 4.93-4.90 (m, 2H), 3.88 (s, 3H), 2.23 (s, 3H), 2.08-1.88 (m, 2H), 0.99 (t, J = 7.4 Hz, 3H). | MS: (ES) m/z calculated for C28H25ClN4O6 [M + H]+ 549.2, found 549.3. |
| (structure with methylpyridinone, methylfuran) | 1H NMR (400 MHz, DMSO-d6) δ 11.89 (s, 1H), 9.82 (s, 1H), 9.14 (d, J = 8.9 Hz, 1H), 7.69-7.53 (m, 3H), 7.32-7.16 (m, 2H), 6.26 (d, J = 3.1 Hz, 1H), 6.06-6.03 (m, 1H), 5.20-5.12 (m, 1H), 4.97 (s, 2H), 2.26 (s, 3H), 2.06 (s, 3H), 2.02-1.83 (m, 2H), 0.93 (t, J = 7.3 Hz, 3H). | MS: (ES) m/z calculated for C26H24N4O5 [M + Na]+ 495.2, found 495.4. |
| (structure with F, methylphenyl, CO$_2$H, methylfuran) | 1H NMR (400 MHz, Methanol-d4) δ 7.94 (d, J = 7.8 Hz, 1H), 7.50-7.31 (m, 4H), 6.19 (d, J = 3.2 Hz, 1H), 5.96-5.93 (m, 1H), 5.22-5.12 (m, 1H), 4.83 (s, 2H), 2.45 (s, 3H), 2.25 (s, 3H), 2.06-1.86 (m, 2H), 0.99 (t, J = 7.4 Hz, 3H). | MS: (ES) m/z calculated for C28H24FN3O6 [M − H]− 516.2, found 516.3. |

TABLE 1-continued

Characterization of compounds

| Structure | NMR | MS |
|---|---|---|
| 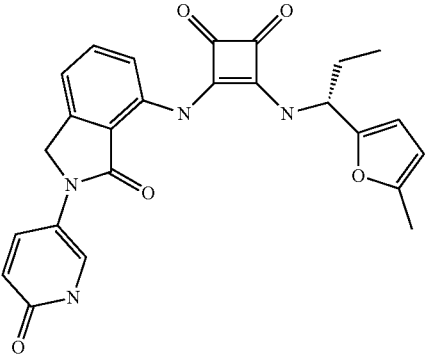 [SMILES: CC[C@@H](Nc1c(Nc2cccc3c2C(=O)N(c2ccc(=O)[nH]c2)C3)c(=O)c1=O)c1ccc(C)o1] | 1H NMR (400 MHz, DMSO-d6) δ 9.81 (s, 1H), 9.14 (d, J = 8.9 Hz, 1H), 7.88 (d, J = 9.1 Hz, 3H), 7.72-7.55 (m, 2H), 7.25 (d, J = 7.1 Hz, 1H), 6.45 (d, J = 10.1 Hz, 1H), 6.27 (d, J = 3.1 Hz, 1H), 6.07-6.04 (m, 1H), 5.20-5.12 (m, 1H), 4.89 (s, 2H), 2.27 (d, J = 1.1 Hz, 3H), 2.06-1.80 (m, 2H), 0.93 (t, J = 7.3 Hz, 3H). | MS: (ES) m/z calculated for C25H22N4O5 [M + H]+ 459.2, found 459.4. |
| 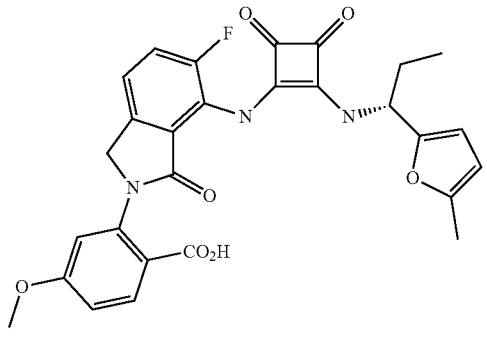 [SMILES: CC[C@@H](Nc1c(Nc2c(F)ccc3c2C(=O)N(c2cc(OC)ccc2C(=O)O)C3)c(=O)c1=O)c1ccc(C)o1] | 1H NMR (400 MHz, Methanol-d4) δ 8.10-7.99 (m, 1H), 7.55-7.37 (m, 2H), 7.14-6.99 (m, 2H), 6.19 (d, J = 3.2 Hz, 1H), 5.96-5.93 (m, 1H), 5.21-5.11 (m, 1H), 3.89 (s, 3H), 4.83 (s, 2H), 2.25 (s, 3H), 2.07-1.88 (m, 2H), 0.99 (t, J = 7.4 Hz, 3H). | MS: (ES) m/z calculated for C28H24FN3O7 [M + Na]+ 556.2, found 556.5. |
| 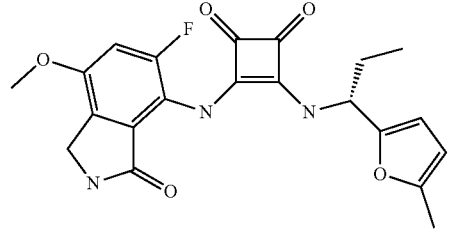 [SMILES: CC[C@@H](Nc1c(Nc2c(F)cc(OC)c3c2C(=O)NC3)c(=O)c1=O)c1ccc(C)o1] | 1H NMR (400 MHz, DMSO-d6) δ 9.27 (s, 1H), 8.75 (s, 1H), 8.11 (d, J = 7.7 Hz, 1H), 7.25 (d, J = 12.6 Hz, 1H), 6.26 (d, J = 3.1 Hz, 1H), 6.07-6.04 (m, 1H), 5.12-5.03 (m, 1H), 4.24 (s, 2H), 3.88 (s, 3H), 2.27 (s, 3H), 1.99-1.82 (m, 2H), 0.92 (t, J = 7.3 Hz, 3H). | MS: (ES) m/z calculated for C21H20FN3O5 [M + Na]+ 436.2, found 436.4. |
| 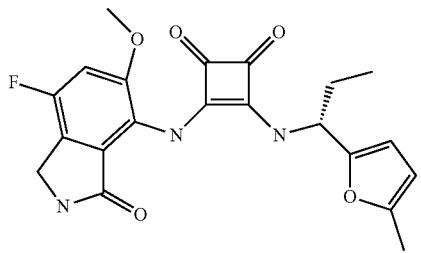 [SMILES: CC[C@@H](Nc1c(Nc2c(OC)cc(F)c3c2C(=O)NC3)c(=O)c1=O)c1ccc(C)o1] | 1H NMR (400 MHz, DMSO-d6) δ 9.17 (s, 1H), 8.64 (s, 1H), 7.98 (d, J = 9.1 Hz, 1H), 7.25 (d, J = 10.5 Hz, 1H), 6.25 (d, J = 3.1 Hz, 1H), 6.07-6.04 (m, 1H), 5.11-5.03 (m, 1H), 4.33 (s, 2H), 3.82 (s, 3H), 2.28 (s, 3H), 1.99-1.82 (m, 2H), 0.92 (t, J = 7.3 Hz, 3H). | MS: (ES) m/z calculated for C21H20FN3O5 [M + Na]+ 436.2, found 436.0. |
| 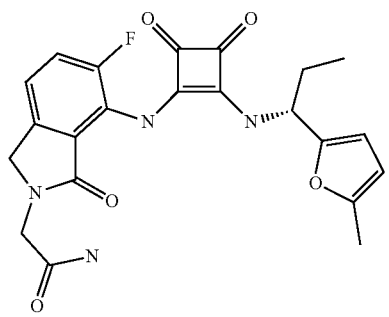 [SMILES: CC[C@@H](Nc1c(Nc2c(F)ccc3c2C(=O)N(CC(N)=O)C3)c(=O)c1=O)c1ccc(C)o1] | 1H NMR (400 MHz, Methanol-d4) δ 8.14-8.08 (m, 1H), 7.27-7.23 (, 1H), 6.25 (d, J = 3.1 Hz, 1H), 6.00-5.96 (m, 1H), 5.20-5.05 (m, 1H), 4.61 (s, 2H), 4.33 (s, 2H), 2.26 (s, 3H), 2.15-1.90 (m, 2H), 1.02 (t, J = 7.4 Hz, 3H). | MS: (ES) m/z calculated for C22H21FN4O5 [M + H]+ 441.2, found 441.4. |

TABLE 1-continued

Characterization of compounds

| Structure | NMR | MS |
|---|---|---|
| 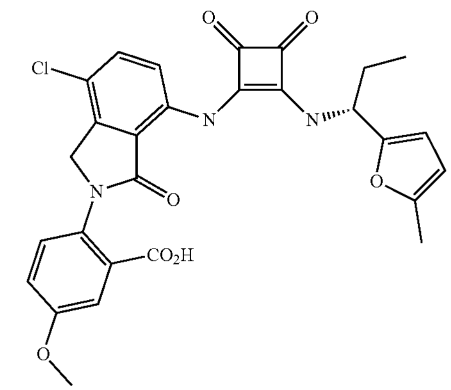 [SMILES: CC[C@@H](Nc1c(Nc2ccc(Cl)c3c2C(=O)N(c2ccc(OC)cc2C(=O)O)C3)c(=O)c1=O)c1ccc(C)o1] | 1H NMR (400 MHz, DMSO-d6) δ 9.76 (s, 1H), 9.15 (d, J = 8.8 Hz, 1H), 7.70-7.63 (m, 2H), 7.52 (d, J = 8.7 Hz, 1H), 7.39 (d, J = 3.0 Hz, 1H), 7.25 (dd, J = 8.7, 3.1 Hz, 1H), 6.23 (d, J = 3.2 Hz, 1H), 6.04-6.00 (m, 1H), 5.17-5.08 (m, 1H), 4.79 (s, 2H), 3.83 (s, 3H), 2.23 (s, 3H), 2.06-1.78 (m, 2H), 0.89 (t, J = 7.3 Hz, 3H). | MS: (ES) m/z calculated for C28H24ClN3O7 [M + H]+ 550.1, found 550.3. |
| 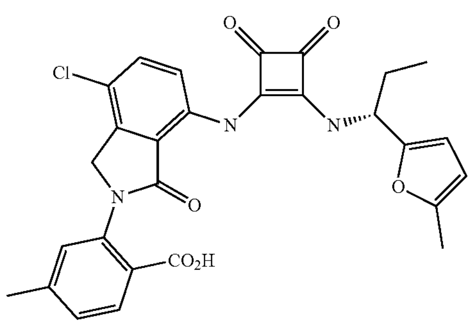 [SMILES: CC[C@@H](Nc1c(Nc2ccc(Cl)c3c2C(=O)N(c2cc(C)ccc2C(=O)O)C3)c(=O)c1=O)c1ccc(C)o1] | 1H NMR (400 MHz, Methanol-d4) δ 8.12-8.05 (m, 1H), 7.95 (d, J = 7.8 Hz, 1H), 7.58 (d, J = 8.8 Hz, 1H), 7.39-7.33 (m, 2H), 6.22-6.18 (m, 1H), 5.95-5.91 (m, 1H), 5.20-4.80 (m, 3H), 2.46 (s, 3H), 2.24 (s, 3H), 2.12-1.82 (m, 2H), 0.99 (t, J = 7.4 Hz, 3H). | MS: (ES) m/z calculated for C28H24ClN3O6 [M + H]+ 534.1, found 534.3. |
| 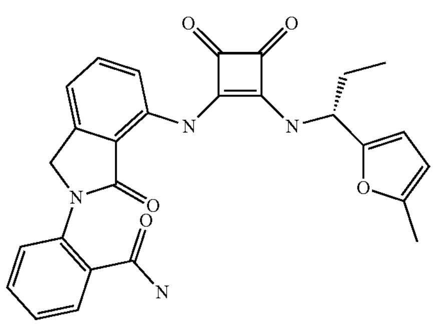 [SMILES: CC[C@@H](Nc1c(Nc2cccc3c2C(=O)N(c2ccccc2C(N)=O)C3)c(=O)c1=O)c1ccc(C)o1] | 1H NMR (400 MHz, DMSO-d6) δ 9.78 (s, 1H), 9.14 (d, J = 9.1 Hz, 1H), 7.78-7.20 (m, 9H), 6.23 (d, J = 3.1 Hz, 1H), 6.05-6.00 (m, 1H), 5.20-5.10 (m, 1H), 4.95-4.83 (m, 2H), 2.23 (s, 3H), 2.03-1.77 (m, 2H), 0.90 (t, J = 7.3 Hz, 3H). | MS: (ES) m/z calculated for C27H24N4O5 [M + Na]+ 507.2, found 507.5. |
| 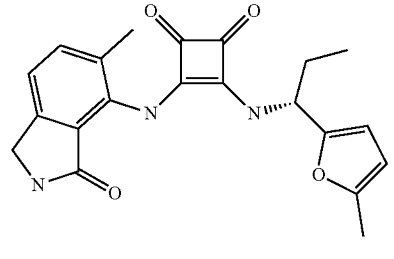 [SMILES: CC[C@@H](Nc1c(Nc2c(C)ccc3c2C(=O)NC3)c(=O)c1=O)c1ccc(C)o1] | 1H NMR (400 MHz, Methanol-d4) δ 7.48 (d, J = 7.7 Hz, 1H), 7.34 (d, J = 7.8 Hz, 1H), 6.21 (d, J = 3.1 Hz, 1H), 5.98-5.95 (m, 1H), 5.20-5.10 (m, 1H), 4.37 (s, 2H), 2.37 (s, 3H), 2.28 (d, J = 1.0 Hz, 3H), 2.08-1.88 (m, 2H), 1.01 (t, J = 7.4 Hz, 3H). | MS: (ES) m/z calculated for C21H21N3O4 [M − H]− 378.1, found 378.3. |

TABLE 1-continued

Characterization of compounds

| Structure | NMR | MS |
|---|---|---|
| 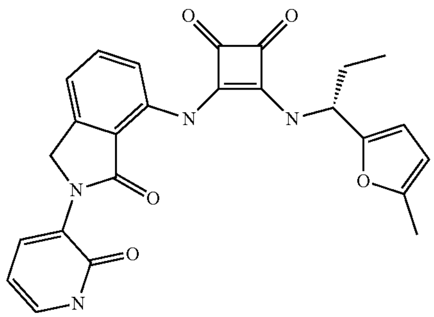 [SMILES: CC[C@@H](Nc1c(Nc2cccc3c2C(=O)N(c2ccc[nH]c2=O)C3)c(=O)c1=O)c1ccc(C)o1] | 1H NMR (400 MHz, DMSO-d6) δ 12.08 (s, 1H), 9.80 (s, 1H), 9.11 (d, J = 9.0 Hz, 1H), 7.71 (dd, J = 7.1, 2.0 Hz, 1H), 7.64-7.53 (m, 2H), 7.44-7.38 (m, 1H), 7.24 (d, J = 7.0 Hz, 1H), 6.30 (d, J = 6.8 Hz, 1H), 6.24 (d, J = 3.1 Hz, 1H), 6.04-6.01 (m, 1H), 5.20-5.10 (m, 1H), 4.93 (s, 2H), 2.24 (s, 3H), 2.00-1.77 (m, 2H), 0.91 (t, J = 7.4 Hz 3H). | MS: (ES) m/z calculated for C25H22N4O5 [M + Na]+ 481.2, found 481.4. |
| 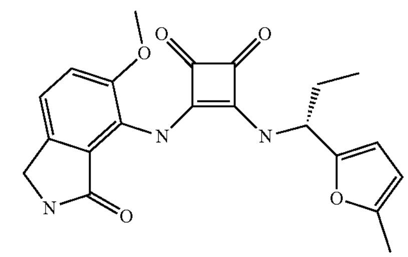 [SMILES: CC[C@@H](Nc1c(Nc2c(OC)ccc3c2C(=O)NC3)c(=O)c1=O)c1ccc(C)o1] | 1H NMR (400 MHz, Chloroform-d) δ 7.10-6.90 (m, 2H), 6.15 (d, J = 3.1 Hz, 1H), 5.89-5.85 (m, 1H), 5.25-5.15 (m, 1H), 4.19 (s, 2H), 3.71 (s, 3H), 2.22 (s, 3H), 1.85-1.60 (m, 2H), 0.97-0.85 (m, 3H). | MS: (ES) m/z calculated for C21H21N3O5 [M − H]− 394.1, found 394.3. |
| 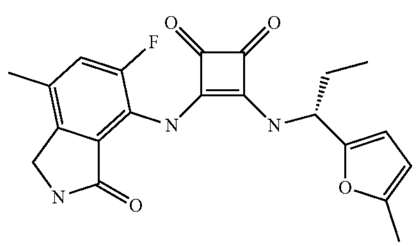 [SMILES: CC[C@@H](Nc1c(Nc2c(F)cc(C)c3c2C(=O)NC3)c(=O)c1=O)c1ccc(C)o1] | 1H NMR (400 MHz, DMSO-d6) δ 9.38 (s, 1H), 8.70 (s, 1H), 8.18 (d, J = 8.9 Hz, 1H), 7.31 (d, J = 11.8 Hz, 1H), 6.25 (d, J = 3.1 Hz, 1H), 6.06-6.02 (m, 1H), 5.12-5.00 (m, 1H), 4.26 (s, 2H), 2.25 (s, 6H), 1.98-1.80 (m, 2H), 0.90 (t, J = 7.3 Hz, 3H). | MS: (ES) m/z calculated for C21H20FN3O4 [M + H]+ 398.1, found 398.4. |
| 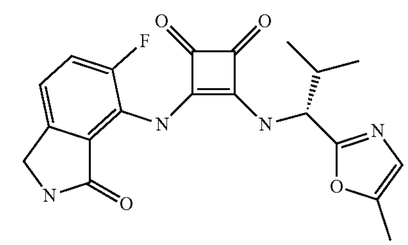 [SMILES: Cc1cnc([C@H](Nc2c(Nc3c(F)ccc4c3C(=O)NC4)c(=O)c2=O)C(C)C)o1] | 1H NMR (400 MHz, DMSO-d6) δ 9.70 (s, 1H), 8.73 (s, 1H), 8.52 (d, J = 9.7 Hz, 1H), 7.49 (dd, J = 11.2, 8.2 Hz, 1H), 7.36 (dd, J = 8.3, 3.9 Hz, 1H), 6.88 (d, J = 1.5 Hz, 1H), 5.23-5.15 (m, 1H), 4.34 (s, 2H), 2.32 (d, J = 1.2 Hz, 3H), 2.29-2.21 (m, 1H), 0.95 (d, J = 6.8 Hz, 3H), 0.92 (d, J = 6.7 Hz, 3H). | MS: (ES) m/z calculated for C20H19FN4O4 [M + H]+ 399.1, found 399.4. |
| 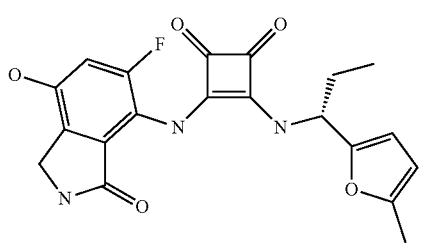 [SMILES: CC[C@@H](Nc1c(Nc2c(F)cc(O)c3c2C(=O)NC3)c(=O)c1=O)c1ccc(C)o1] | 1H NMR (400 MHz, DMSO-d6) δ 10.62 (s, 1H), 9.04 (s, 1H), 8.55 (s, 1H), 7.94-7.84 (m, 1H), 6.88 (d, J = 9.9 Hz, 1H), 6.25 (d, J = 3.1 Hz, 1H), 6.07-6.04 (m, 1H), 5.13-5.01 (m, 1H), 4.28 (s, 2H), 2.27 (d, J = 1.0 Hz, 3H), 1.99-1.81 (m, 2H), 0.92 (t, J = 7.3 Hz, 3H). | MS: (ES) m/z calculated for C20H18FN3O5 [M + H]+ 400.1, found 400.4. |
| 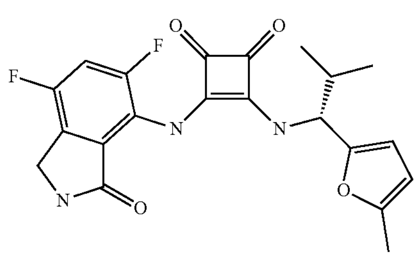 [SMILES: Cc1ccc([C@H](Nc2c(Nc3c(F)cc(F)c4c3C(=O)NC4)c(=O)c2=O)C(C)C)o1] | 1H NMR (400 MHz, DMSO-d6) δ 9.49 (s, 1H), 8.91 (s, 1H), 8.24 (d, J = 9.7 Hz, 1H), 7.61 (dd, J = 10.9, 8.6 Hz, 1H), 6.21 (d, J = 3.1 Hz, 1H), 6.05-6.02 (m, 1H), 5.00-4.91 (m, 1H), 4.41 (s, 2H), 2.26 (s, 3H), 2.21-2.11 (m, 1H), 0.95 (d, J = 6.7 Hz, 3H), 0.87 (d, J = 6.7 Hz, 3H). | MS: (ES) m/z calculated for C21H19F2N3O4 [M + H]+ 416.1, found 416.4. |

TABLE 1-continued

Characterization of compounds

| Structure | NMR | MS |
|---|---|---|
| 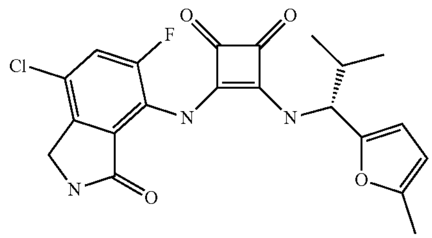 [SMILES: Cc1ccc([C@H](Nc2c(Nc3c(F)cc(Cl)c4c3C(=O)NC4)c(=O)c2=O)C(C)C)o1] | 1H NMR (400 MHz, DMSO-d6) δ 9.59 (s, 1H), 8.93 (s, 1H), 8.30 (d, J = 9.8 Hz, 1H), 7.77 (d, J = 10.6 Hz, 1H), 6.21 (d, J = 3.1 Hz, 1H), 6.04 (d, J = 3.0 Hz, 1H), 5.01-4.93 (m, 1H), 4.32 (s, 2H), 2.26 (d, J = 1.2 Hz, 3H), 2.23-2.13 (m, 1H), 0.95 (d, J = 6.7 Hz, 3H), 0.87 (d, J = 6.7 Hz, 3H). | MS: (ES) m/z calculated for C21H19ClFN3O4 [M + H]+ 432.1, found 432.4. |
| 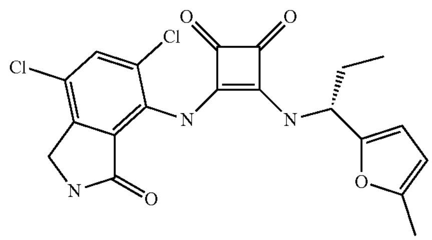 [SMILES: CC[C@@H](Nc1c(Nc2c(Cl)cc(Cl)c3c2C(=O)NC3)c(=O)c1=O)c1ccc(C)o1] | 1H NMR (400 MHz, DMSO-d6) δ 9.50 (s, 1H), 8.82 (s, 1H), 8.08-8.00 (m, 2H), 7.93 (s, 1H), 6.27 (d, J = 3.1 Hz, 1H), 6.08-6.05 (m, 1H), 5.13-5.02 (m, 1H), 4.33 (s, 2H), 2.28 (s, 3H), 2.00-1.80 (m, 2H), 0.92 (t, J = 7.3 Hz, 3H). | MS: (ES) m/z calculated for C20H17Cl2N3O4 [M + H]+ 434.1, found 434.3. |
| 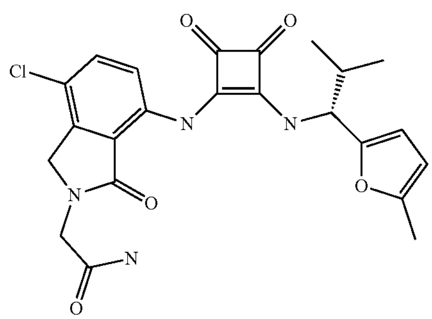 [SMILES: Cc1ccc([C@H](Nc2c(Nc3ccc(Cl)c4c3C(=O)N(CC(N)=O)C4)c(=O)c2=O)C(C)C)o1] | 1H NMR (400 MHz, DMSO-d6) δ 9.83 (s, 1H), 9.15 (d, J = 9.5 Hz, 1H), 7.66-7.55 (m, 3H), 7.29-7.20 (m, 1H), 6.23 (d, J = 3.1 Hz, 1H), 6.07-6.03 (m, 1H), 5.08-5.00 (m, 1H), 4.50 (s, 2H), 4.14 (s, 2H), 2.27 (s, 3H), 2.25-2.13 (m, 1H), 0.97 (d, J = 6.7 Hz, 3H), 0.88 (d, J = 6.7 Hz, 3H). | MS: (ES) m/z calculated for C23H23ClN4O5 [M + Na]+ 493.1, found 493.4. |
| 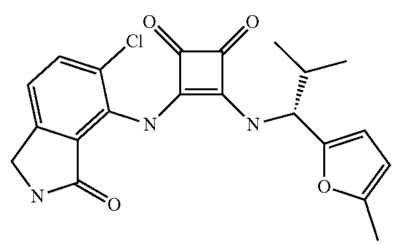 [SMILES: Cc1ccc([C@H](Nc2c(Nc3c(Cl)ccc4c3C(=O)NC4)c(=O)c2=O)C(C)C)o1] | 1H NMR (400 MHz, DMSO-d6) δ 9.49 (s, 1H), 8.56 (s, 1H), 8.08 (d, J = 9.8 Hz, 1H), 7.68 (d, J = 8.0 Hz, 1H), 7.38 (d, J = 8.1 Hz, 1H), 6.22 (d, J = 3.1 Hz, 1H), 6.06-6.02 (m, 1H), 5.00-4.92 (m, 1H), 4.32 (s, 2H), 2.27 (s, 3H), 2.24-2.09 (m, 1H), 0.96 (d, J = 6.7 Hz, 3H), 0.87 (d, J = 6.7 Hz, 3H). | MS: (ES) m/z calculated for C21H20ClN3O4 [M + H]+ 414.1, found 414.4. |
| 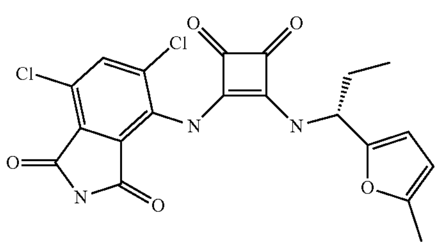 [SMILES: CC[C@@H](Nc1c(Nc2c(Cl)cc(Cl)c3c2C(=O)NC3=O)c(=O)c1=O)c1ccc(C)o1] | 1H NMR (400 MHz, DMSO-d6) δ 11.55 (s, 1H), 9.82 (s, 1H), 8.16-8.00 (m, 2H), 6.30-6.22 (m, 1H), 6.07-6.02 (m, 1H), 5.14-5.02 (m, 1H), 2.25 (s, 3H), 2.04-1.75 (m, 2H), 0.91 (t, J = 6.5 Hz, 3H). | MS: (ES) m/z calculated for C20H15Cl2N3O5 [M + Na]+ 470.0, found 470.2. |
| 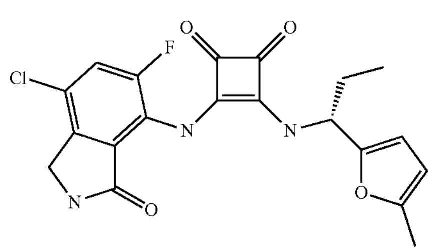 | 1H NMR (400 MHz, DMSO-d6) δ 9.53 (s, 1H), 8.93 (s, 1H), 8.23 (d, J = 8.7 Hz, 1H), 7.76 (d, J = 10.6 Hz, 1H), 6.25 (d, J = 3.1 Hz, 1H), 6.06-6.02 (m, 1H), 5.12-5.00 (m, 1H), 4.32 (s, 2H), 2.25 (s, 3H), 1.99-1.80 (m, 2H), 0.90 (t, J = 7.3 Hz, 3H). | MS: (ES) m/z calculated for C20H17ClFN3O4 [M + H]+ 418.1, found 418.4. |

TABLE 1-continued

Characterization of compounds

| Structure | NMR | MS |
|---|---|---|
| 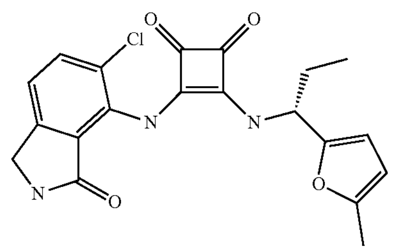 [SMILES: CC[C@@H](Nc1c(Nc2c(Cl)ccc3c2C(=O)NC3)c(=O)c1=O)c1ccc(C)o1] | 1H NMR (400 MHz, DMSO-d6) δ 9.43 (s, 1H), 8.57 (s, 1H), 8.08-7.98 (m, 1H), 7.68 (d, J = 8.0 Hz, 1H), 7.38 (d, J = 8.1 Hz, 1H), 6.26 (d, J = 3.1 Hz, 1H), 6.06-6.03 (m, 1H), 5.12-5.00 (m, 1H), 4.31 (s, 2H), 2.26 (s, 3H), 1.99-1.80 (m, 2H), 0.91 (t, J = 7.3 Hz, 3H). | MS: (ES) m/z calculated for C20H18ClN3O4 [M + Na]+ 422.1, found 422.0. |
| 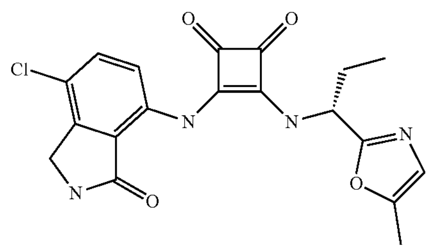 [SMILES: CC[C@@H](Nc1c(Nc2ccc(Cl)c3c2C(=O)NC3)c(=O)c1=O)c1ncc(C)o1] | 1H NMR (400 MHz, DMSO-d6) δ 9.85 (s, 1H), 9.35 (d, J = 8.9 Hz, 1H), 8.93 (s, 1H), 7.63-7.55 (m, 2H), 6.84 (s, 1H), 5.35-5.25 (m, 1H), 4.36 (s, 2H), 2.29 (s, 3H), 2.07-1.85 (m, 2H), 0.92 (t, J = 7.3 Hz, 3H). | MS: (ES) m/z calculated for C19H17ClN4O4 [M + H]+ 401.1, found 401.0. |
| 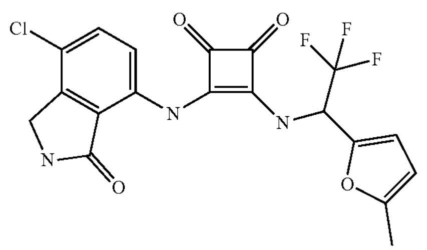 [SMILES: Cc1ccc(C(Nc2c(Nc3ccc(Cl)c4c3C(=O)NC4)c(=O)c2=O)C(F)(F)F)o1] | 1H NMR (400 MHz, DMSO-d6) δ 10.01 (s, 1H), 9.80 (d, J = 9.4 Hz, 1H), 8.96 (s, 1H), 7.61 (d, J = 8.7 Hz, 1H), 7.52 (d, J = 8.7 Hz, 1H), 6.65 (d, J = 3.2 Hz, 1H), 6.19 (d, J = 3.2 Hz, 1H), 6.17-6.05 (m, 1H), 4.37 (s, 2H), 2.31 (s, 3H). | MS: (ES) m/z calculated for C19H13ClF3N3O4 [M + H]+ 440.1, found 440.0. |
| 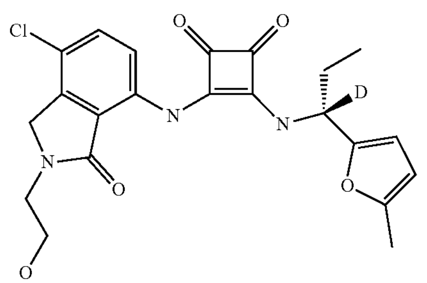 [SMILES: [2H][C@](CC)(Nc1c(Nc2ccc(Cl)c3c2C(=O)N(CCO)C3)c(=O)c1=O)c1ccc(C)o1] | 1H NMR (400 MHz, DMSO-d6) δ 9.78 (s, 1H), 9.15 (s, 1H), 7.64-7.57 (m, 2H), 6.25 (d, J = 3.1 Hz, 1H), 6.05-6.02 (m, 1H), 4.85 (t, J = 5.4 Hz, 1H), 4.53 (s, 2H), 3.65-3.52 (m, 4H), 2.25 (s, 3H), 2.03-1.78 (m, 2H), 0.90 (t, J = 7.4 Hz, 3H). | MS: (ES) m/z calculated for C22DH21ClN3O5 [M + Na]+ 467.1, found 467.1. |
| 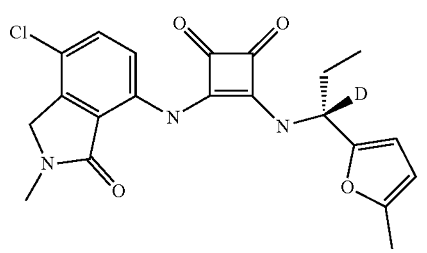 [SMILES: [2H][C@](CC)(Nc1c(Nc2ccc(Cl)c3c2C(=O)N(C)C3)c(=O)c1=O)c1ccc(C)o1] | 1H NMR (400 MHz, DMSO-d6) δ 9.75 (s, 1H), 9.15 (s, 1H), 7.63-7.55 (m, 2H), 6.25 (d, J = 3.1 Hz, 1H), 6.06-6.02 (m, 1H), 4.46 (s, 2H), 3.06 (s, 3H), 2.25 (s, 3H), 2.00-1.80 (m, 2H), 0.90 (t, J = 7.3 Hz, 3H). | MS: (ES) m/z calculated for C21DH19ClN3O4 [M + H]+ 415.1, found 415.1. |
| 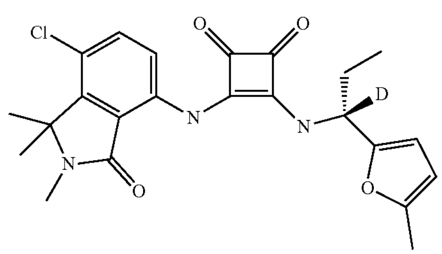 [SMILES: [2H][C@](CC)(Nc1c(Nc2ccc(Cl)c3c2C(=O)N(C)C3(C)C)c(=O)c1=O)c1ccc(C)o1] | 1H NMR (400 MHz, DMSO-d6) δ 9.86 (s, 1H), 9.21 (s, 1H), 7.65-7.55 (m, 2H), 6.25 (d, J = 3.1 Hz, 1H), 6.04 (d, J = 3.1 Hz, 1H), 2.92 (s, 3H), 2.24 (s, 3H), 2.00-1.80 (m, 2H), 1.55 (s, 6H), 0.90 (t, J = 7.3 Hz, 3H). | MS: (ES) m/z calculated for C23DH23ClN3O4 [M + H]+ 443.1, found 443.1. |

TABLE 1-continued

Characterization of compounds

| Structure | NMR | MS |
|---|---|---|
| 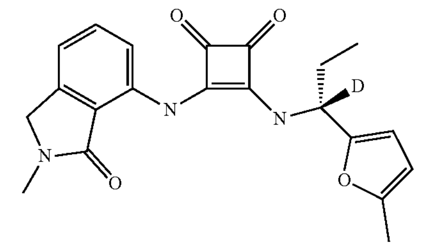 [SMILES: [2H][C@](CC)(Nc1c(Nc2cccc3c2C(=O)N(C)C3)c(=O)c1=O)c1ccc(C)o1] | 1H NMR (400 MHz, DMSO-d6) δ 9.77 (s, 1H), 9.13 (s, 1H), 7.60-7.47 (m, 2H), 7.18 (d, J = 7.3 Hz, 1H), 6.25 (d, J = 3.1 Hz, 1H), 6.06-6.02 (m, 1H), 4.45 (s, 2H), 3.04 (s, 3H), 2.25 (s, 3H), 2.00-1.80 (m, 2H), 0.91 (t, J = 7.3 Hz, 3H). | MS: (ES) m/z calculated for C21DH20N3O4 [M + H]+ 381.2, found 381.2. |
| 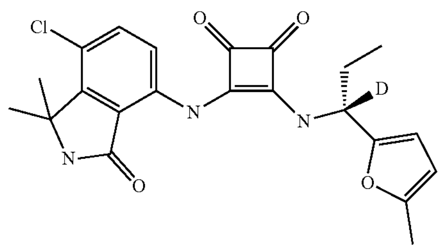 [SMILES: [2H][C@](CC)(Nc1c(Nc2ccc(Cl)c3c2C(=O)NC3(C)C)c(=O)c1=O)c1ccc(C)o1] | 1H NMR (400 MHz, DMSO-d6) δ 9.86 (s, 1H), 9.28-8.96 (m, 2H), 7.64-7.48 (m, 2H), 6.30-6.16 (m, 1H), 6.07-5.95 (m, 1H), 2.23 (s, 3H), 1.98-1.78 (m, 2H), 1.55 (s, 6H), 0.93-0.83 (m, 3H). | MS: (ES) m/z calculated for C22DH21ClN3O4 [M + H]+ 429.1, found 429.1. |
| 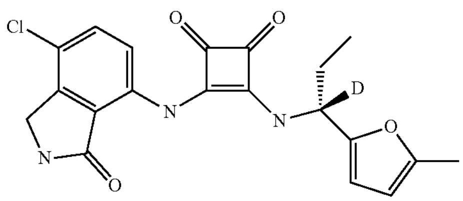 [SMILES: [2H][C@](CC)(Nc1c(Nc2ccc(Cl)c3c2C(=O)NC3)c(=O)c1=O)c1ccc(C)o1] | 1H NMR (400 MHz, DMSO-d6) δ 9.76 (s, 1H), 9.16 (s, 1H), 8.93 (s, 1H), 7.59 (s, 2H), 6.25 (d, J = 3.1 Hz, 1H), 6.05-6.02 (m, 1H), 4.36 (s, 2H), 2.25 (s, 3H), 2.00-1.80 (m, 2H), 0.90 (t, J = 7.3 Hz, 3H). | MS: (ES) m/z calculated for C20DH17ClN3O4 [M + H]+ 401.1, found 401.1. |
| 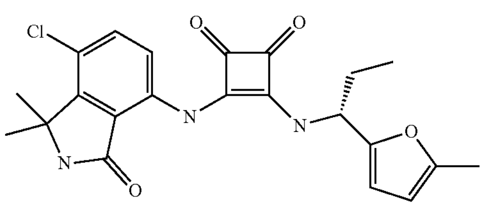 | 1H NMR (400 MHz, DMSO-d6) δ 9.82 (s, 1H), 9.19 (d, J = 8.9 Hz, 1H), 9.05 (s, 1H), 7.61-7.53 (m, 2H), 6.25 (d, J = 3.1 Hz, 1H), 6.05-6.02 (m, 1H), 5.20-5.10 (m, 1H), 2.24 (s, 3H), 2.01-1.80 (m, 2H), 1.55 (s, 6H), 0.91 (t, J = 7.3 Hz, 3H). | MS: (ES) m/z calculated for C22H22ClN3O4 [M + H]+ 428.1, found 428.1. |
| 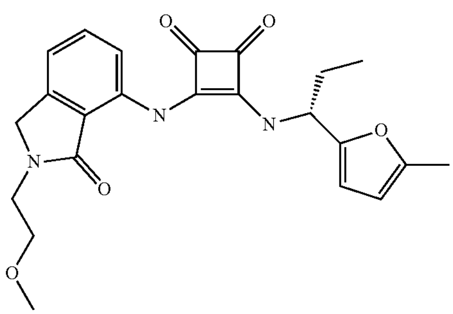 [SMILES: CC[C@@H](Nc1c(Nc2cccc3c2C(=O)N(CCOC)C3)c(=O)c1=O)c1ccc(C)o1] | 1H NMR (400 MHz, DMSO-d6) δ 9.77 (s, 1H), 9.13 (d, J = 9.0 Hz, 1H), 7.59-7.48 (m, 2H), 7.19 (d, J = 7.2 Hz, 1H), 6.25 (d, J = 3.1 Hz, 1H), 6.05-6.02 (m, 1H), 5.20-5.09 (m, 1H), 4.51 (s, 2H), 3.65 (t, J = 5.3 Hz, 2H), 3.54 (t, J = 5.4 Hz, 2H), 3.24 (s, 3H), 2.25 (s, 3H), 2.00-1.81 (m, 2H), 0.91 (t, J = 7.3 Hz, 3H). | MS: (ES) m/z calculated for C23H25N3O5 [M + H]+ 424.2, found 424.1. |
| 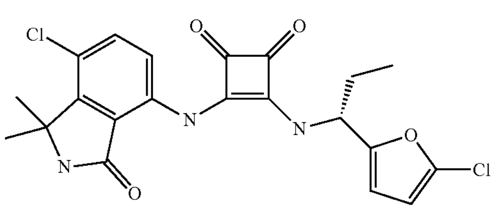 [SMILES: CC[C@@H](Nc1c(Nc2ccc(Cl)c3c2C(=O)NC3(C)C)c(=O)c1=O)c1ccc(Cl)o1] | 1H NMR (400 MHz, DMSO-d6) δ 9.84 (s, 1H), 9.21 (d, J = 8.8 Hz, 1H), 9.06 (s, 1H), 7.63-7.54 (m, 2H), 6.53-6.44 (m, 2H), 5.22-5.12 (m, 1H), 2.01-1.83 (m, 2H), 1.56 (s, 6H), 0.91 (t, J = 7.3 Hz, 3H). | MS: (ES) m/z calculated for C21H19Cl2N3O4 [M + H]+ 448.1, found 448.0. |

TABLE 1-continued

Characterization of compounds

| Structure | NMR | MS |
|---|---|---|
| 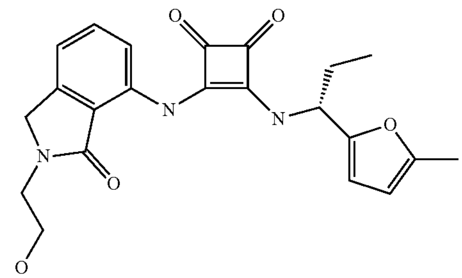 [SMILES: CC[C@@H](Nc1c(Nc2cccc3c2C(=O)N(CCO)C3)c(=O)c1=O)c1ccc(C)o1] | 1H NMR (400 MHz, DMSO-d6) δ 9.79 (s, 1H), 9.13 (d, J = 8.9 Hz, 1H), 7.59-7.48 (m, 2H), 7.19 (d, J = 7.3 Hz, 1H), 6.25 (d, J = 3.1 Hz, 1H), 6.05-6.02 (m, 1H), 5.19-5.09 (m, 1H), 4.86-4.82 (m, 1H), 4.54 (s, 2H), 3.63-3.51 (m, 4H), 2.25 (s, 3H), 2.01-1.80 (m, 2H), 0.91 (t, J = 7.3 Hz, 3H). | MS: (ES) m/z calculated for $C_{22}H_{23}N_3O_5$ [M + Na]+ 432.2, found 432.1. |
| 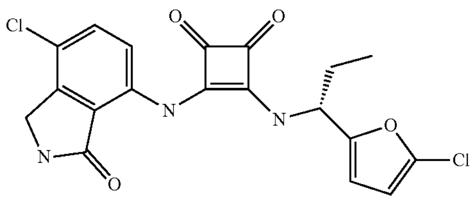 [SMILES: CC[C@@H](Nc1c(Nc2ccc(Cl)c3c2C(=O)NC3)c(=O)c1=O)c1ccc(Cl)o1] | 1H NMR (400 MHz, DMSO-d6) δ 9.79 (s, 1H), 9.20 (d, J = 8.8 Hz, 1H), 8.95 (s, 1H), 7.65-7.58 (m, 2H), 6.53 (d, J = 3.3 Hz, 1H), 6.48 (d, J = 3.3 Hz, 1H), 5.23-5.13 (m, 1H), 4.38 (s, 2H), 2.04-1.82 (m, 2H), 0.93 (t, J = 7.3 Hz, 3H). | MS: (ES) m/z calculated for $C_{19}H_{15}Cl_2N_3O_4$ [M + H]+ 420.0, found 420.0. |
| 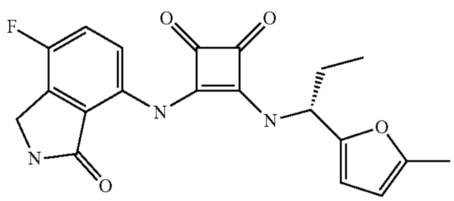 [SMILES: CC[C@@H](Nc1c(Nc2ccc(F)c3c2C(=O)NC3)c(=O)c1=O)c1ccc(C)o1] | 1H NMR (400 MHz, DMSO-d6) δ 9.70 (s, 1H), 9.08 (d, J = 9.3 Hz, 1H), 8.90 (s, 1H), 7.59-7.52 (m, 1H), 7.41 (t, J = 8.8 Hz, 1H), 6.25 (d, J = 3.1 Hz, 1H), 6.06-6.02 (m, 1H), 5.19-5.09 (m, 1H), 4.45 (s, 2H), 2.25 (s, 3H), 2.01-1.80 (m, 2H), 0.91 (t, J = 7.3 Hz, 3H). | MS: (ES) m/z calculated for $C_{20}H_{18}FN_3O_4$ [M + H]+ 384.1, found 384.1. |
| 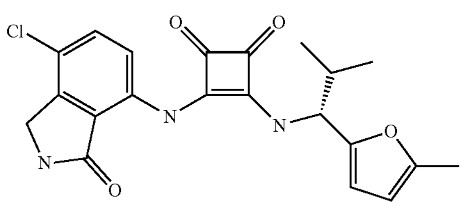 [SMILES: Cc1ccc([C@H](Nc2c(Nc3ccc(Cl)c4c3C(=O)NC4)c(=O)c2=O)C(C)C)o1] | 1H NMR (400 MHz, DMSO-d6) δ 9.83 (s, 1H), 9.16 (d, J = 9.5 Hz, 1H), 8.92 (s, 1H), 7.59 (d, J = 8.7 Hz, 1H), 7.53 (d, J = 8.7 Hz, 1H), 6.22 (d, J = 3.1 Hz, 1H), 6.05-6.02 (m, 1H), 5.06-4.98 (m, 1H), 4.36 (s, 2H), 2.26 (s, 3H), 2.24-2.13 (m, 1H), 0.96 (d, J = 6.7 Hz, 3H), 0.86 (d, J = 6.7 Hz, 3H). | MS: (ES) m/z calculated for $C_{21}H_{20}ClN_3O_4$ [M + H]+ 414.1, found 414.1. |
| 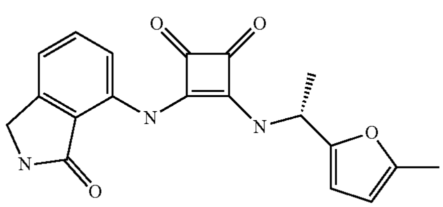 [SMILES: Cc1ccc([C@@H](C)Nc2c(Nc3cccc4c3C(=O)NC4)c(=O)c2=O)o1] | 1H NMR (400 MHz, DMSO-d6) δ 9.74 (s, 1H), 9.18 (d, J = 8.6 Hz, 1H), 8.69 (s, 1H), 7.62-7.47 (m, 2H), 7.17 (d, J = 7.3 Hz, 1H), 6.26 (d, J = 3.1 Hz, 1H), 6.06-6.02 (m, 1H), 5.42-5.28 (m, 1H), 4.36 (s, 2H), 2.24 (s, 3H), 1.55 (d, J = 6.9 Hz, 3H). | MS: (ES) m/z calculated for $C_{19}H_{17}N_3O_4$ [M + Na]+ 374.1, found 374.1. |
| 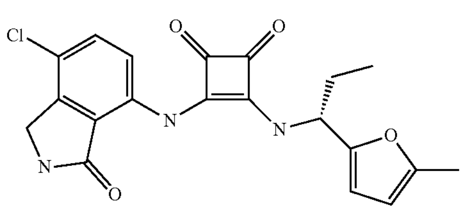 [SMILES: CC[C@@H](Nc1c(Nc2ccc(Cl)c3c2C(=O)NC3)c(=O)c1=O)c1ccc(C)o1] | 1H NMR (400 MHz, DMSO-d6) δ 9.76 (s, 1H), 9.16 (d, J = 9.0 Hz, 1H), 8.92 (s, 1H), 7.59 (s, 2H), 6.25 (d, J = 3.1 Hz, 1H), 6.05-6.02 (m, 1H), 5.19-5.09 (m, 1H), 4.36 (s, 2H), 2.25 (s, 3H), 2.01-1.80 (m, 2H), 0.91 (t, J = 7.3 Hz, 3H). | MS: (ES) m/z calculated for $C_{20}H_{18}ClN_3O_4$ [M + H]+ 400.1, found 400.0. |
| 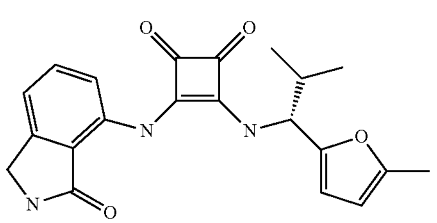 [SMILES: Cc1ccc([C@H](Nc2c(Nc3cccc4c3C(=O)NC4)c(=O)c2=O)C(C)C)o1] | 1H NMR (400 MHz, DMSO-d6) δ 9.84 (s, 1H), 9.15 (d, J = 9.5 Hz, 1H), 8.69 (s, 1H), 7.54-7.46 (m, 2H), 7.18 (d, J = 6.7 Hz, 1H), 6.22 (d, J = 3.1 Hz, 1H), 6.05-6.02 (m, 1H), 5.07-4.99 (m, 1H), 4.37 (s, 2H), 2.26 (s, 3H), 2.23-2.13 (m, 1H), 0.96 (d, J = 6.7 Hz, 3H), 0.86 (d, J = 6.7 Hz, 3H). | MS: (ES) m/z calculated for $C_{21}H_{21}N_3O_4$ [M + H]+ 380.1, found 380.1. |

TABLE 1-continued

Characterization of compounds

| Structure | NMR | MS |
|---|---|---|
| 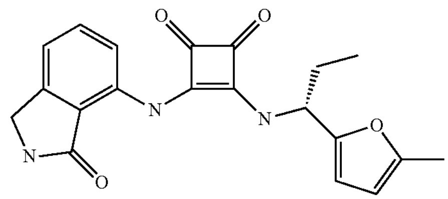 [SMILES: CC[C@@H](Nc1c(Nc2cccc3c2C(=O)NC3)c(=O)c1=O)c1ccc(C)o1] | 1H NMR (400 MHz, DMSO-d6) δ 9.77 (s, 1H), 9.13 (d, J = 8.9 Hz, 1H), 8.69 (s, 1H), 7.58-7.48 (m, 2H), 7.17 (d, J = 7.1 Hz, 1H), 6.25 (d, J = 3.1 Hz, 1H), 6.05-6.02 (m, 1H), 5.20-5.09 (m, 1H), 4.36 (s, 2H), 2.25 (s, 3H), 2.02-1.80 (m, 2H), 0.91 (t, J = 7.3 Hz, 3H). | MS: (ES) m/z calculated for C20H19N3O4 [M + H]+ 366.1, found 366.1. |

Biological Example 1

Ligand Binding Assay for CXCR2 Activity

Figure 1D:
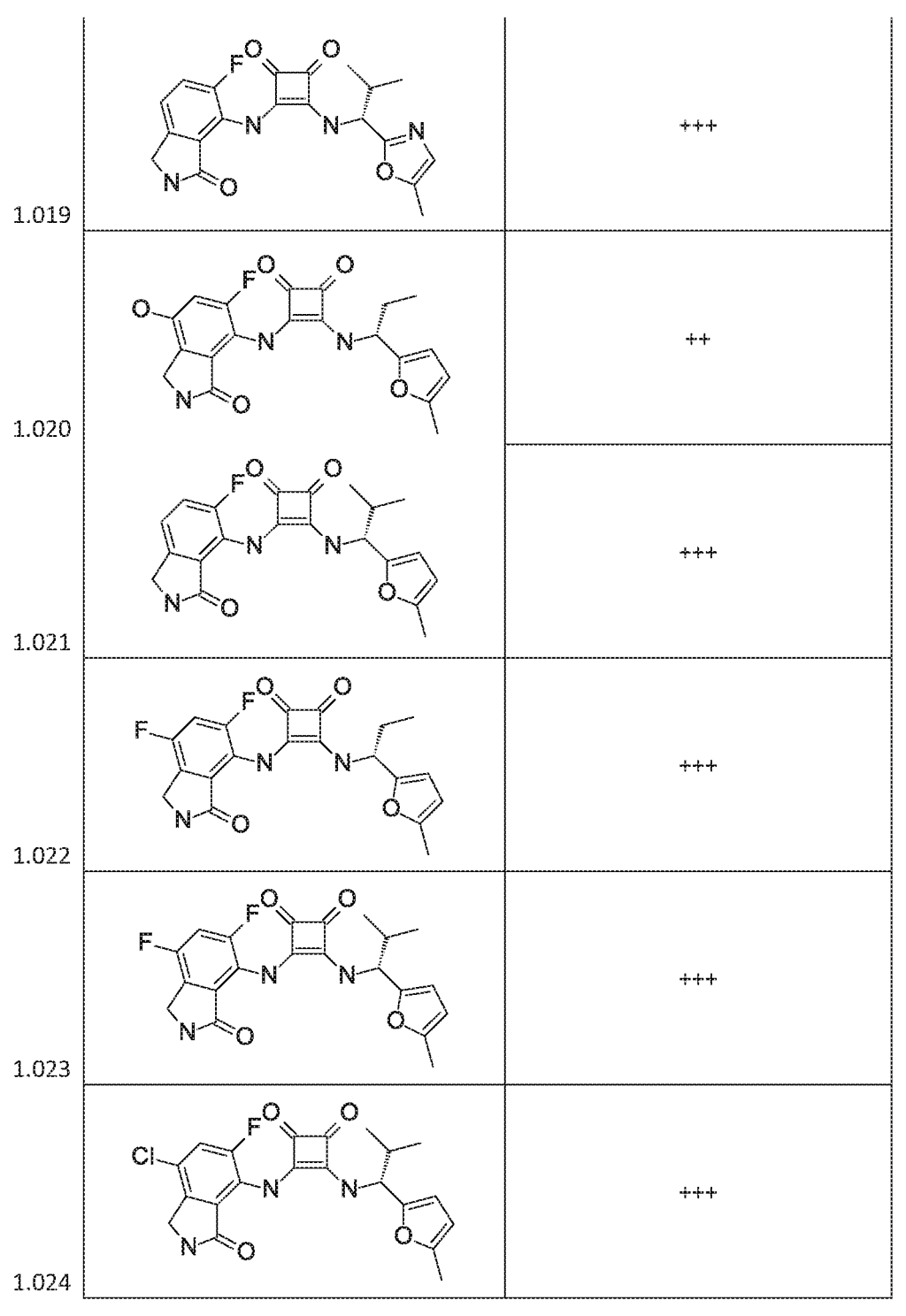

A ligand binding assay can be used to determine the ability of potential CXCR2 antagonists to block the interaction between CXCR2 and any of its ligands. HEK-293 cells stably expressing CXCR2 or human neutrophils expressing CXCR2, are centrifuged and resuspended in assay buffer (20 mM HEPES pH 7.1, 140 mM NaCl, 1 mM $CaCl_2$, 5 mM $MgCl_2$, 0.1% sodium azide and with 0.1% bovine serum albumin) to a concentration of $5 \times 10^5$ cells/mL. Binding assays are set up as follows: Compounds for screening are serially diluted from a maximum of 20 µM, and 0.1 mL of cells containing $5 \times 10^4$ cells (for the HEK-293 cells) or $3 \times 10^4$ cells (for the human neutrophils) is added to each well containing compound. Then 0.1 mL of $^{125}I$ labeled CXCL8 (obtained from PerkinElmer; Waltham, Mass.) diluted in assay buffer to a final concentration of ~50 µM, yielding ~1 µCi per well is added, and the plates are sealed and incubated for approximately 3 hours at 25° C. on a shaker platform. Reactions are aspirated onto GF/B glass filters pre-soaked in 0.3% polyethyleneimine (PEI) solution, on a vacuum cell harvester (Packard Instruments; Meriden, Conn.). Scintillation fluid (50 uL; Microscint 20, Packard Instruments) is added to each well, the plates are sealed and radioactivity measured in a Top Count scintillation counter (Packard Instruments). Control wells containing either diluent only (for total counts) or 20 µM compound are used to calculate the percent of total inhibition for compound. The computer program Prism from GraphPad, Inc. (San Diego, Ca) can be used to calculate $IC_{50}$ values. $IC_{50}$ values are those concentrations required to reduce the binding of labeled CXCR8 to the receptor by 50%. Compounds in FIG. 1 having an $IC_{50}$ value in the binding assay of less than 100 nM are labeled (+++); from 100-1000 nM are labeled (++); and less than or equal to 20 µM but above 1000 nM are labeled (+).

Biological Example 2

Migration/Chemotaxis Assay

A serum chemotaxis assay can be used to determine the efficacy of potential receptor antagonists at blocking the migration mediated through chemokine receptors, such as CXCR2. This assay is routinely performed using the ChemoTX® microchamber system with a 5-µm pore-sized polycarbonate membrane. To begin such an assay, chemokine-receptor expressing cells (in this case neutrophils isolated from human whole blood) are collected by centrifugation at 400×g at room temperature, then suspended at 4 million/ml in human serum. The compound being tested is serially diluted from a maximum final concentration of 10 µM (or an equivalent volume of its solvent (DMSO)) and is then added to the cell/serum mixture. Separately, recombinant human CXCL5 (ENA-78) at its $EC_5$ concentration (10 nM) is placed in the lower wells of the ChemoTX® plate. The 5-µm (pore size) polycarbonate membrane is placed onto the plate, and 20 µL of the cell/compound mixture is transferred onto each well of the membrane. The plates are incubated at 37° C. for 45 minutes, after which the polycarbonate membranes are removed and 5 µl of the DNA-intercalating agent CyQUANT (Invitrogen, Carlsbad, Calif.) is added to the lower wells. The amount of fluorescence, corresponding to the number of migrated cells, is measured using a Spectrafluor Plus plate reader (TECAN, San Jose, Calif.).

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having formula

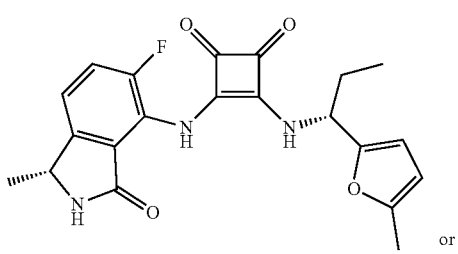

or

-continued

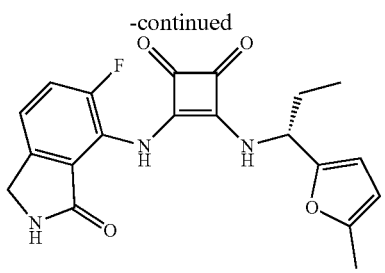

or a pharmaceutically acceptable salt thereof.

2. A pharmaceutical composition comprising a compound of claim 1.

3. The pharmaceutical composition of claim 2, further comprising one or more additional therapeutic agents.

4. The pharmaceutical composition of claim 3 wherein the one or more additional therapeutic agents are selected from the group consisting of a cytotoxic chemotherapeutic agent, an anti-cancer or anti-tumor vaccine, chimeric antigen receptor (CAR) T cell immunotherapeutic agent, and checkpoint inhibitors.

5. The pharmaceutical composition of claim 3 wherein the one or more additional therapeutic agents are selected from the group consisting of:
   drugs that block the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

6. A method of treating a disease or disorder selected from the group consisting of psoriasis, rheumatoid arthritis, radiation induced fibrotic lung disease, autoimmune bullous dermatosis (AIBD), chronic obstructive pulmonary disease, and ozone-induced airway inflammation in a subject in need thereof, said method comprising administering an effective amount of a compound or a pharmaceutically acceptable salt of claim 1 to said subject.

7. A method of treating a cancer selected from the group consisting of rhabdomyocarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, head and neck squamous cell carcinoma, pancreatic cancer, thyroid papillary cancer, intrahepatic cholangiocellular carcinoma, hepatocellular carcinoma, bone cancer, and nasopharyngeal carcinoma in a subject in need thereof, said method comprising administering an effective amount of a compound or a pharmaceutically acceptable salt of claim 1 to said subject.

8. A method of claim 7, wherein the compound or a pharmaceutically acceptable salt thereof, is used to treat cancer alone or in combination with one or more other anti-cancer therapies.

9. A method of claim 8, wherein the compound or a pharmaceutically acceptable salt thereof, is used to treat cancer in combination with one or more of a cytotoxic chemotherapeutic agent, an anti-cancer vaccine, an anti-tumor vaccine, and a chimeric antigen receptor (CAR) T cell immunotherapeutic agent, and gene transfer therapy.

10. A method of claim 8, wherein the compound or a pharmaceutically acceptable salt thereof, is used to treat cancer in combination with one or more checkpoint inhibitors.

11. The method of claim 8 wherein the one or more other anti-cancer therapy is selected from the group consisting of: drugs that block the activity of CTLA-4(CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

12. The compound of claim 1 having the formula

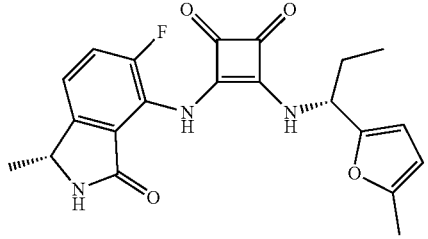

13. The compound of claim 1 having the formula

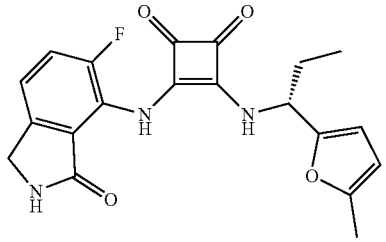

* * * * *